(12) United States Patent
Chakravarty et al.

(10) Patent No.: US 10,294,476 B2
(45) Date of Patent: May 21, 2019

(54) NEAT1 AS A PROGNOSTIC MARKER AND THERAPEUTIC TARGET FOR PROSTATE CANCER

(71) Applicant: CORNELL UNIVERSITY, Ithaca, NY (US)

(72) Inventors: Dimple Chakravarty, New York, NY (US); Mark A. Rubin, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/304,086

(22) PCT Filed: Apr. 17, 2015

(86) PCT No.: PCT/US2015/026359
§ 371 (c)(1),
(2) Date: Oct. 14, 2016

(87) PCT Pub. No.: WO2015/161189
PCT Pub. Date: Oct. 22, 2015

(65) Prior Publication Data
US 2017/0037408 A1 Feb. 9, 2017

Related U.S. Application Data

(60) Provisional application No. 61/980,825, filed on Apr. 17, 2014.

(51) Int. Cl.
| C12Q 1/68 | (2018.01) |
| C12N 15/113 | (2010.01) |
| C12Q 1/6886 | (2018.01) |
| A61K 31/713 | (2006.01) |
| A61K 45/06 | (2006.01) |

(52) U.S. Cl.
CPC ........ *C12N 15/1135* (2013.01); *A61K 31/713* (2013.01); *A61K 45/06* (2013.01); *C12N 15/113* (2013.01); *C12Q 1/6886* (2013.01); *C12N 2310/113* (2013.01); *C12N 2310/14* (2013.01); *C12N 2310/351* (2013.01); *C12N 2320/30* (2013.01); *C12N 2320/31* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 2012/0058130 A1 | 3/2012 | Donald |
| 2013/0225659 A1 | 8/2013 | Bennett |
| 2013/0303400 A1 | 11/2013 | Zeillinger et al. |

OTHER PUBLICATIONS

Du et al., Nature Structural & Molecular Biology vol. 20(7):908-915, Jul. 2013.*
Gibb et al., PLoS ONE vol. 6(10), 2011, 10 pages.*
Blute M.L. et al., "Use of Gleason score, prostate specific antigen, seminal vesicle and margin status to predict biochemical failure after radical prostatectomy" J Urol, (2001), 165:119-125.
Karnes R.J. et al., "Validation of a Genomic Classifier that Predicts Metastasis Following Radical Prostatectomy in an At Risk Patient Population" J Urol, (2013), 190(6): 2047-2053.
Amaral P.P. et al., "lncRNAdb: a reference database for long noncoding RNAs" Nucleic Acids Res, (2011) 39: D146-151.
Arredouani M.S. et al., "Identification of the transcription factor single-minded homologue 2 as a potential biomarker and immunotherapy target in prostate cancer" Clin Cancer Res, (2009), 15: 5794-5802.
Barbieri C.E. et al., "Exome sequencing identifies recurrent SPOP, FOXA1 and MED12 mutations in prostate cancer" Nature genetics, (2012), 44: 685-689.
Barwick B.G. et al., "Prostate cancer genes associated with TMPRSS2-ERG gene fusion and prognostic of biochemical recurrence in multiple cohorts" Br J Cancer, (2010), 102: 570-576.
Benjamini Y. et al., "Controlling the False Discovery Rate: A Practical and Powerful Approach to Multiple Testing" Journal of the Royal Statistical Society. Series B (Methodological), (1995), 57: 289-300.
Best C.J.M. et al., "Molecular alterations in primary prostate cancer after androgen ablation therapy" Clin Cancer Res, (2005), 11: 6823-6834.
Bond C.S. et al., "Paraspeckles: nuclear bodies built on long noncoding RNA" J Cell Biol, (2009), 186: 637-644.
Burger M.J. et al., "Expression analysis of delta-catenin and prostate-specific membrane antigen: their potential as diagnostic markers for prostate cancer" Int J Cancer, (2002), 100: 228-237.
Cerami E. et al., "The cBio cancer genomics portal: an open platform for exploring multidimensional cancer genomics data" Cancer Discov, (2012), 2: 401-404.
Chu C. et al., "Chromatin isolation by RNA purification (ChIRP)" Journal of visualized experiments: JoVE, (2012), 61: E3912, 1-6.
Clemson C.M. et al., "An architectural role for a nuclear noncoding RNA: NEAT1 RNA is essential for the structure of paraspeckles" Mol Cell, (2009), 33: 717-726.
De Bono J.S. et al., "Abiraterone and increased survival in metastatic prostate cancer" N Engl J Med, (2011), 364: 1995-2005.
Erho N. et al., "Discovery and Validation of a Prostate Cancer Genomic Classifier that Predicts Early Metastasis Following Radical Prostatectomy" PLoS One, (2013), 8: e66855.

(Continued)

*Primary Examiner* — Sean McGarry
(74) *Attorney, Agent, or Firm* — Scully Scott Murphy & Presser

(57) ABSTRACT

This invention relates to diagnosis and prognosis of prostate cancer, as well as therapeutic treatment of prostate cancer. More specifically, the invention provides diagnostic and prognostic methods based on detecting nuclear enriched abundant transcript 1 (NEAT1) levels in a sample. Further provided are methods for treating prostate cancer based on targeting NEAT1 via interfering RNA.

24 Claims, 23 Drawing Sheets
(18 of 23 Drawing Sheet(s) Filed in Color)
Specification includes a Sequence Listing.

(56) References Cited

OTHER PUBLICATIONS

Gao J. et al., "Integrative analysis of complex cancer genomics and clinical profiles using the cBioPortal" Sci Signal, (2013), 6: pl1.
Giannopoulou E.G. et al., "An integrated ChIP-seq analysis platform with customizable workflows" BMC bioinformatics, (2011), 12: 277.
Glinsky G.V. et al., "Gene expression profiling predicts clinical outcome of prostate cancer" J Clin Invest, (2004), 113: 913-923.
Grasso C.S. et al., "The mutational landscape of lethal castration-resistant prostate cancer" Nature, (2012), 487: 239-243.
Gumulec J. et al., "Evaluation of alpha-methylacyl-CoA racemase, metallothionein and prostate specific antigen as prostate cancer prognostic markers" Neoplasma, (2012), 59: 191-201.
Guttman M. et al., "Chromatin signature reveals over a thousand highly conserved large non-coding RNAs in mammals" Nature, (2009), 458: 223-227.
Heinlein C.A. et al., "Androgen receptor in prostate cancer" Endocr Rev, (2004), 25: 276-308.
Holzbeierlein J. et al., "Gene expression analysis of human prostate carcinoma during hormonal therapy identifies androgen-responsive genes and mechanisms of therapy resistance" Am J Pathol, (2004), 164: 217-227.
Jiangn. et al., "A-Methylacyl-CoA Racemase (AMACR) and Prostate-Cancer Risk: A Meta-Analysis of 4,385 Participants" PLoS One, (2013), 8: e74386.
Lapointe J. et al., "Gene expression profiling identifies clinically relevant subtypes of prostate cancer" Proc Natl Acad Sci USA, (2004), 101: 811-816.
Latulippe E. et al., "Comprehensive gene expression analysis of prostate cancer reveals distinct transcriptional programs associated with metastatic disease" Cancer Res, (2002), 62: 4499-4506.
Liu P. et al., "Sex-determining region Y box 4 is a transforming oncogene in human prostate cancer cells" Cancer Res, (2006), 66: 4011-4019.
Luo J. et al., "Human prostate cancer and benign prostatic hyperplasia: molecular dissection by gene expression profiling" Cancer Res, (2001), 61: 4683-4688.
Magee J.A. et al., "Expression profiling reveals hepsin overexpression in prostate cancer" Cancer Res, (2001), 61: 5692-5696.
Nakagawa S. et al., "Paraspeckles are subpopulation-specific nuclear bodies that are not essential in mice" J Cell Biol, (2011), 193: 31-39.
Rhodes D.R. et al., "Oncomine 3.0: genes, pathways, and networks in a collection of 18,000 cancer gene expression profiles" Neoplasia, (2007), 9: 166-180.
Rhodes D.R. et al., "ONCOMINE: a cancer microarray database and integrated data-mining platform" Neoplasia, (2004), 6: 1-6.
Ricke W.A. et al., "Prostatic hormonal carcinogenesis is mediated by in situ estrogen production and estrogen receptor alpha signaling" FASEB J, (2008), 22: 1512-1520.
Ross J.S. et al., "Correlation of primary tumor prostate-specific membrane antigen expression with disease recurrence in prostate cancer" Clin Cancer Res, (2003), 9: 6357-6362.
Scher H.I. et al., "Increased survival with enzalutamide in prostate cancer after chemotherapy" N Engl J Med, (2012), 367: 1187-1197.
Singh D. et al., "Gene expression correlates of clinical prostate cancer behavior" Cancer Cell, (2002), 1: 203-209.
Tamura K. et al., "Molecular features of hormone-refractory prostate cancer cells by genome-wide gene expression profiles" Cancer Res, (2007), 67: 5117-5125.
Taylor B.S. et al., "Integrative genomic profiling of human prostate cancer" Cancer Cell, (2010), 18: 11-22.
Tomlins S.A. et al., "Integrative molecular concept modeling of prostate cancer progression" Nat Genet, (2007), 39: 41-51.
Vanaja D. et al., "Transcriptional silencing of zinc finger protein 185 identified by expression profiling is associated with prostate cancer progression" Cancer Res, (2003), 63: 3877-3882.
Varambally S. et al., "Integrative genomic and proteomic analysis of prostate cancer reveals signatures of metastatic progression" Cancer Cell, (2005), 8: 393-406.
Wallace T.A. et al., "Tumor immunobiological differences in prostate cancer between African-American and European-American men" Cancer Res, (2008), 68: 927-936.
Welsh J.B. et al., "Analysis of gene expression identifies candidate markers and pharmacological targets in prostate cancer" Cancer Res, (2001), 61: 5974-5978.
Xiao Z. et al., "Quantitation of serum prostate-specific membrane antigen by a novel protein biochip immunoassay discriminates benign from malignant prostate disease" Cancer Res, (2001), 61: 6029-6033.
Yu J. et al., "An integrated network of androgen receptor, polycomb, and TMPRSS2-ERG gene fusions in prostate cancer progression" Cancer cell, (2010), 17: 443-454.
Yu Y.P. et al., "Gene expression alterations in prostate cancer predicting tumor aggression and preceding development of malignancy" J Clin Oncol, (2004), 22: 2790-2799.
International Search Report and Written Opinion dated Aug. 21, 2015 issued in PCT/US15/26359.
Gibb E.A. et al., "Human Cancer Long Non-Coding RNA Transcriptomes" PLoS One, (2011), 6(10): e25915, 1-10.
Souquere S. et al., "Highly Ordered Spatial Organization of the Structural Long Noncoding NEAT1 RNAs within Paraspeckle Nuclear Bodies" Mol Biol Cell, (2010), 21(22): 4020-4027.
Marin-Aguilera M. et al., "Identification of Docetaxel Resistance Genes in Castration-Resistant Prostate Cancer" Mol Cancer Ther, (2012), 11(2): 329-339.
NCBI_283131, NEAR1 nuclear paraspeckle assembly transcript 1 (non-protein coding) [*Homo sapiens* (human)] Gene ID: 283131, updated: May 31, 2015, [online]. Retrieved from the Internet: <URL: http://ncbi.nlm.nih.gov/gene/283131>.
Chakravarty D. et al., "The oestrogen receptor alpha-regulated lncRNA NEAT1 is a critical modulator of prostate cancer" Nat Commun, (2014), 55383, 1-16.

\* cited by examiner

SEQUENCE LISTING

<160> NUMBER OF SEQ ID NOS: 50

<210> SEQ ID NO 1
<211> LENGTH: 3729
<212> TYPE: DNA
<213> ORGANISM: Homo sapiens

<400> SEQUENCE: 1

```
ggagttagcg acagggaggg atgcgcgcct gggtgtagtt gtggggagg aagtggctag        60 ctcagggctt caggggacag acaggagag atgactgagt tagatgagac gaggggcgg        120 gctggggtg cgagaaggaa gcttggcaag gagactaggt ctaggggac cacagtgggg        180 caggctgcat ggaaaatatc cgcagggtcc cccaggcaga acagccacgc tccaggccag       240
gctgtcccta ctgcctggtg gaggggaac ttgacctctg ggagggcgcc gctcttgcat        300
agctgagcga gcccgggtgc gctggtctgt gtggaaggag gaaggcaggg agaggtagaa       360
ggggtggagg agtcaggagg aataggccgc agcagccctg gaaatgatca ggaaggcagg       420
cagtgggtgc agggctgcag gagggccggg agggctaatc ttcaacttgt ccatgccagc      480 agccccttt tttccagacc aagggctgtg aacccgcctg gggatgaggc ctggtcttgt       540
ggaactgaac ttagctcgac ggggctgacc gctctggccc agggtggtat gtaattttcg      600
ctcggcctgg gacggggccc aggccgggcc cagcctggtg gagcgtccag gtctgggtgc     660
gaagccaggc ccctgggcgg aggtgagggg tggtctgagg agtgatgtgg agttaaggcg     720
ccatcctcac cggtgactgg tgcggcacct agcatgtttg acaggcgggg actgcgaggc   780
acgctgctcg ggtgttgggg acaacattga ccaacgcttt attttccagg tggcagtgct    840
ccttttggac ttttctctag gtttggcgct aaactcttct tgtgagctca ctccacccct    900
tcttcctccc tttaacttat ccattcactt aaaacattac ctggtcatct ggtaagcccg    960
ggacagtaag ccgagtggct gttggagtcg gtattgttgg taatggtgga ggaagagagg   1020
ccttcccgct gaggctgggg tggggcggat cggtgttgct tgcctgcaga gagggtgggg    1080
agtgaatgtg caccctgggg tgggcctgca gccatccagc tgaaagttac aaaaatgctt   1140
catggaccgt ggtttgttac tatagtgttc ctcatggcga gcagatggaa ccgggagaca  1200
tggagtccct ggccagtgtg agtcctagca ttgcaggagg ggagaccctg gaggagagag   1260
cccgcctcaa ttgatgcctg cagattgaat ttccagaggc ttaggaggag gaagttctcc   1320
aatgttctgt ttccaggcct tgctcaggaa gccctgtatt caggaggcta ccatttaaag   1380
tttgcagatg agcttatggg gggcaatctt aaaaagtcca cagcagatgc atccggctcg   1440
aggggccatc agctttgaat aaatgctttg tccagagccc atgaatgcca gcaggcaccc  1500
ctcctttcct ggggtaaagg ttttcagatg ctgcatcttc taaattgagc ctccggtcat   1560
actagttttg tgcttggaac cttgcttcaa gaagatccct aagctgtaga acattttaac   1620
```

```
gttgatgcca caacgcagat tgatgccttg tagatggagc ttgcagatgg agccccgtga    1680
cctctcacct acccacctgt ttgcctgcct tcttgtgcgt ttctcggaga agttcttagc    1740
ctgatgaaat aacttggggc gttgaagagc tgtttaattt taaatgcctt agactgggga    1800
tatattagag gaagcagatt gtcaaattaa gggtgtcatt tgttgtgct aaacgctggg    1860 agggtacaag ttggtcattc ctaaatctgt gtgtgagaaa tggcaggtct agtttgggca    1920
ttgtgattgc attgcagatt actaggagaaa gggaatggtg ggtacaccgg tagtgctctt    1980
ttgttcttgc ttcgtttttt taaacttgaa ctttacttcg ttagatttca taatactttc    2040
ttggcattct agtaagagga ccctgaggtg ggagttgtgg gggacgggga aaggggaca    2100 gcttggcacc ggtcccgtgg gcgttgcagt gtggggatg ggggtatgca gcttggcact    2160
ggtactggga gggatgaggg tgaagaaggg gagagggttg gttagagata cagtgtgggt    2220
ggtgggggtg gtaggaaatg caggttgaag ggaattctct ggggctttgg ggaatttagt    2280
gcgtgggtga gccaagaaaa tactaattaa taatagtaag ttgttagtgt tggttaagtt    2340
gttgcttgga agtgagaagt tgcttagaaa cttttccaaag tgcttagaac tttaagtgca    2400
aacagacaaa ctaacaaaca aaaattgttt tgctttgcta caaggtgggg aagactgaag    2460
aagtgttaac tgaaaacagg tgacacagag tcaccagttt tccgagaacc aaagggaggg    2520
gtgtgtgatg ccatctcaca ggcagggaa atgtctttac cagcttcctc ctggtggcca    2580
agacagcctg tttcagaggg ttgttttgtt tggggtgtgg gtgttatcaa gtgaattagt    2640
cacttgaaag atgggcgtca gacttgcata cgcagcagat cagcatcctt cgctgcccct    2700
tagcaactta ggtggttgat ttgaaactgt gaaggtgtga ttttttcagg agctggaagt    2760
cttagaaaag ccttgtaaat gcctatattg tgggcttta acgtatttaa gggaccactt    2820
aagacgagat tagatgggct cttctggatt tgttcctcat ttgtcacagg tgtcttgtga    2880
ttgaaaatca tgagcgaagt gaaattgcat tgaatttcaa gggaattag tatgtaaatc    2940 gtgccttaga aacacatctg ttgtcttttc tgtgtttggt cgatattaat aatggcaaaa    3000
ttttgtccta tctagtatct tcaaattgta gtctttgtaa caaccaaata acctttgtg    3060 gtcactgtaa aattaatatt tggtagacag aatccatgta cctttgctaa ggttagaatg    3120
aataatttat tgtatttta atttgaatgt ttgtgctttt taaatgagcc aagactagag    3180
gggaaactat cacctaaaat cagtttggaa aacaagacct aaaaagggaa ggggatgggg    3240
attgtgggga gagagtgggc gaggtgcctt tactacatgt gtgatctgaa aaccctgctt    3300
ggttctgagc tgcgtctatt gaattggtaa agtaatacca atggcttttt atcatttcct    3360
tcttcccttt aagtttcact tgaaatttta aaaatcatgg ttatttttat cgttgggatc    3420
tttctgtctt ctgggttcca tttttaaat gtttaaaaat atgttgacat ggtagttcag    3480
ttcttaacca atgacttggg gatgatgcaa acaattactg tcgttgggat ttagagtgta    3540
ttagtcacgc atgtatgggg aagtagtctc gggtatgctg ttgtgaaatt gaaactgtaa    3600
aagtagatgg ttgaaagtac tggtatgttg ctctgtatgg taagaactaa ttctgttacg    3660
tcatgtacat aattactaat cacttttctt ccccttaca gcacaaataa agtttgagtt    3720
ctaaactca                                                              3729
```

<210> SEQ ID NO 2
<211> LENGTH: 22743
<212> TYPE: DNA
<213> ORGANISM: Homo sapiens

<400> SEQUENCE: 2

```
ggagttagcg acagggaggg atgcgcgcct gggtgtagtt gtggggagg aagtggctag      60
ctcagggctt caggggacag acagggagag atgactgagt tagatgagac gaggggggcgg   120
gctgggggtg cgagaaggaa gcttggcaag gagactaggc ctaggggac cacagtgggg    180
caggctgcat ggaaaatatc cgcagggtcc cccaggcaga acagccacgc tccaggccag    240
gctgtcccta ctgcctggtg gagggggaac ttgacctctg ggaggggcgcc gctcttgcat   300
agctgagcga gcccgggtgc gctggtctgt gtggaaggag gaaggcaggg agaggtagaa    360
gggtgggagg agtcaggagg aataggccgc agcagccctg gaaatgatca ggaaggcagg    420
cagtgggtgc agggctgcag gagggccggg agggctaatc ttcaacttgt ccatgccagc    480
agccccttt tttccagacc aagggctgtg aacccgcctg gggatgaggc ctggtcttgt     540
ggaactgaac ttagctcgac ggggctgacc gctctggccc agggtggtat gtaattttcg    600
ctcggcctgg gacggggccc aggccgggcc cagcctggtg gagcgtccag gtctgggtgc    660
gaagccaggc ccctgggcgg aggtgagggg tggtctgagg agtgatgtgg agttaaggcg    720
ccatcctcac cggtgactgg tgcggcacct agcatgttg acaggcgggg actgcgaggc    780
acgctgctcg ggtgttgggg acaacattga ccaacgcttt attttccagg tggcagtgct    840
ccttttggac ttttctctag gtttggcgct aaactcttct tgtgagctca ctccacccct    900
tcttcctccc tttaacttat ccattcactt aaaacattac ctggtcatct ggtaagcccg    960
ggacagtaag ccgagtggct gttggagtcg gtattgttgg taatggtgga ggaagagagg   1020
ccttcccgct gaggctgggg tggggcggat cggtgttgct tgcctgcaga gagggtgggg   1080
agtgaatgtg cacccttggg tgggcctgca gccatccagc tgaaagttac aaaaatgctt   1140
catgaccgt ggtttgttac tatagtgttc ctcatggcga gcagatggaa ccgggagaca    1200
tggagtccct ggccagtgtg agtcctagca ttgcaggagg ggagaccctg gaggagagag   1260
cccgcctcaa ttgatgcctg cagattgaat ttccagaggc ttaggaggag gaagttctcc   1320
aatgttctgt ttccaggcct tgctcaggaa gccctgtatt caggaggcta ccatttaaag   1380
tttgcagatg agcttatggg gggcaatctt aaaaagtcca cagcagatgc atccggctcg   1440
aggggccatc agctttgaat aaatgcttgt tccagagccc atgaatgcca gcaggcaccc   1500
ctccttcct ggggtaaagg ttttcagatg ctgcatcttc taaattgagc ctccggtcat    1560
actagttttg tgcttggaac cttgcttcaa gaagatccct aagctgtaga acattttaac   1620
gttgatgcca caacgcagat tgatgccttg tagatggagc ttgcagatgg agccccgtga   1680
cctctcacct acccacctgt ttgcctgcct tcttgtgcgt ttctcggaga agttcttagc   1740
ctgatgaaat aacttgggc gttgaagagc tgtttaattt taaatgcctt agactgggga   1800
tatattagag gaagcagatt gtcaaattaa gggtgtcatt gtgttgtgct aaacgctggg   1860
agggtacaag ttggtcattc ctaaatctgt gtgtgagaaa tggcaggtct agtttgggca   1920
ttgtgattgc attgcagatt actaggagaa gggaatggtg ggtacaccgg tagtgctctt   1980
ttgttcttgc ttcgtttttt taaacttgaa ctttacttcg ttagatttca taatactttc   2040
ttggcattct agtaagagga ccctgaggtg ggagttgtgg gggacgggga aaggggaca    2100
gcttggcacc ggtcccgtgg gcgttgcagt gtggggatg ggggtatgca gcttggcact   2160
ggtactggga gggatgaggg tgaagaaggg gagagggttg gttagagata cagtgtgggt   2220
ggtggggtg gtaggaaatg caggttgaag ggaattctct ggggctttgg ggaatttagt   2280
gcgtgggtga gccaagaaaa tactaattaa taatagtaag ttgttagtgt tggttaagtt   2340
```

```
gttgcttgga agtgagaagt tgcttagaaa cttccaaag tgcttagaac tttaagtgca    2400
aacagacaaa ctaacaaaca aaaattgttt tgctttgcta caaggtgggg aagactgaag    2460
aagtgttaac tgaaaacagg tgacacagag tcaccagttt tccgagaacc aaagggaggg    2520
gtgtgtgatg ccatctcaca ggcagggaa atgtctttac cagcttcctc ctggtggcca    2580
agacagcctg tttcagaggg ttgttttgtt tggggtgtgg gtgttatcaa gtgaattagt    2640
cacttgaaag atgggcgtca gacttgcata cgcagcagat cagcatcctt cgctgcccct    2700
tagcaactta ggtggttgat ttgaaactgt gaaggtgtga ttttttcagg agctggaagt    2760
cttagaaaag ccttgtaaat gcctatattg tgggctttta acgtatttaa gggaccactt    2820
aagacgagat tagatgggct cttctggatt tgttcctcat ttgtcacagg tgtcttgtga    2880
ttgaaaatca tgagcgaagt gaaattgcat tgaatttcaa gggaatttag tatgtaaatc    2940
gtgccttaga aacacatctg ttgtcttttc tgtgtttggt cgatattaat aatggcaaaa    3000
tttttgccta tctagtatct tcaaattgta gtctttgtaa caaccaaata accttttgtg    3060
gtcactgtaa aattaatatt tggtagacag aatccatgta cctttgctaa ggttagaatg    3120
aataatttat tgtattttta atttgaatgt ttgtgctttt taaatgagcc aagactagag    3180
gggaaactat cacctaaaat cagtttggaa acaagacct aaaagggaa ggggatgggg    3240 attgtgggga gagagtgggc gaggtgcctt tactacatgt gtgatctgaa aaccctgctt    3300
ggttctgagc tgcgtctatt gaattggtaa agtaatacca atggcttttt atcatttcct    3360
tcttcccttt aagtttcact tgaaatttta aaaatcatgg ttatttttat cgttgggatc    3420
tttctgtctt ctgggttcca ttttttaaat gtttaaaaat atgttgacat ggtagttcag    3480
ttcttaacca atgacttggg gatgatgcaa acaattactg tcgttgggat ttagagtgta    3540
ttagtcacgc atgtatgggg aagtagtctc gggtatgctg ttgtgaaatt gaaactgtaa    3600
aagtagatgg ttgaaagtac tggtatgttg ctctgtatgg taagaactaa ttctgttacg    3660
tcatgtacat aattactaat cacttttctt cccctttaca gcacaaataa agtttgagtt    3720
ctaaactcat tagaattgtt gtattgctat gttacatttc tcgaccccta tcacattgcc    3780
ttcataacga ctttggatgt atcttcatat tgtagattta ggtctagatt tgctagctcc    3840
aagtaattaa ggccatgtag gagagcatgg taaccacaga tagaactggt attatcccaa    3900
gtggtctgca gactgctgag tggggatggg atctgctctc tgttgagagt tggtaatcat    3960
tggtttgaaa tgtgatgaaa ccactcaagc caatgaaggt gggtgtgtag gtggggagta    4020
ctttgccata atattttaaa acattcctg gttagagttc taagtggtac ttattttgt    4080 ttggttaggg gaaagcctga ataaaaacag aaatggacac ataatatgca tattccatag    4140
tctttgggag gctggaatgt gcctgggatt tgggtctaag tgtatgcgta attcttacct    4200
cactaaagaa tttgccttgt ttttttcctt ttggtgagtg actaaaacgt ctgggcttcc    4260
ctgtgtgcgt gctacagtaa gcaagcagag gctgtgcaaa ggtgtgagca ggatcacgtg    4320
gaatctggag gatacatctt ggcttgcaaa ctgcctctgt ctcctgggtg ggactgttct    4380
gtccttgcac tgctgttctg tgttacctct tggggtgtaa ggttttgctt acaggagaca    4440
aactttgggc gtagaatgga agccactgcc agcctctgtg ctgagaagga aggtgcttgt    4500
ttcaaaggga gcagcaaggg aggcttgttc tactcacctg ggcctgtttg cctgagaagg    4560
ggagataagg gctgaactgg gactagccag ggggaccaac acaaatggtg ggggatcatg    4620
acctgaagga ttctttcctt cccatgagct gcagggctgg ttgccgtcct tgcaactgtg    4680
```

```
tcttatttgc ctgtgccgtt atatcttggt gacccctcca cgtgtacact actgacaaac    4740
gggtggagtg ctggggagaa gtcactgtgc cgcccaccta gtaaaccttc tgtctgtgct    4800
catggcatct ccaagatggg gcactgctgt gtgcagaatc cagggtcctc tttctgcttg    4860
caactccttt ccctggatgc cccagaaaca atccaggcct cctttcctat cttacccctt    4920
tgctttgctt tttaccccag cacctctata accgccttct cttcttttca gaactccttg    4980
tttctcgtcc tgttttttat gattacaaaa ctcttgcttc caccctggaa gataactgct    5040
atagatgcct gtatgtaaat ggtgctgtct ccagcaactg gcatgctgaa gaagaattga    5100
ttcacggggt ataaatgttg gggattggaa gtggggatga atggcacttg gttgatacag    5160
gagcagagag gtgaggccga ctgctgaaga cagctcgcca ccctccttgc ctccactcca    5220
atccaggggc tggggccaca ttctttgcct tcatttatcc tcagatcagg tgagatcgac    5280
aggaggtgtt gatggcagtg ccagcaatta ttgctaatcc gtttgcatcc ttatgcatag    5340
atctgaattc agactttgtg aatttccaga ggtgtgggta atataataga attcagtgag    5400
tgggcatggc tgatcttgtg caaattaaaa gttatggggc ataagaatag caaaagttga    5460
acttctttta aaaaggaaag taccctgaga gccagtattg gttgaggctc ttcagtatgc    5520
ccaggttggc agcactgaga accgcaggaa cggcctgttg ttacaaaaag gagattgact    5580
cagctgccct tggtgcatct gactgactat gactgctgag agattccaag gacccttaat    5640
gccagggcta acctctccat gtgcagtgag acctctggag gaagtgtcat cctctggctt    5700
tgtgtggtac tcattatggt gcagtgcggg catgaaatga agacacccaa ataggcttac    5760
agatacgata tgttttaaat gttcgtattt aacaaaaaca tactgacact gtttggaaat    5820
ggcaacagga agatagcaaa atgaatacta acattacgaa aagatgaaca ggtacatgtt    5880
ccaaggcagg tggctgtgaa cttcctctga gtgaaggcat cccctccagc acctttcagc    5940
ctgctagtta ggacgacccg ccgccaccct ccaggacctc cagccctgca ctgccttttcc    6000 tctctttttaa ataattcttc attgagttct aatatgtaaa aaaaaaaagt ttactgtaaa    6060
gtttgcaaat aaggaaattt tttttaaaag tcctcagtaa tcttaccagt aacaattgtt    6120
atgggcacat ttgcttttgg aagatttctt ttgtatgcat gggataagta cattttttaaa    6180 caaaaatggg attatgccat aaattctatt ttgtgacttt aatatatagt gaacacctttt    6240 tttaatgatg acaggatgtt cccttgcatg gctgtatcaa tttaaacaat cttgtttcaa    6300
tgggcataca gggtattttc tagtttttttt ttcctcttag aaaataatac ttgcgatgac    6360
tttccttgta gctcagactt tttcacgtct gttgttatct ctttgggaat gctgaataca    6420
tacatttcga gaaggaaatg actgttaaac tcttaagact tcaggttcat attgctaaac    6480
tgcccagcag ggagggattt tttcaattag tgttctcact ggtgaggcaa acctgatgcc    6540
ttcccctctt cctcagaacc ggctttatca cattgaaaac ctttgctcct ccgacggatc    6600
gagtctgctt tccctctgga tgtgagcatt gctttgtctg ctggtgactg aacatctcta    6660
ccttgtgtca attggccatt tgtggtgtgt gtgtgtgtgc gtgtgtgtgt gtgtgtgtgt    6720
gtatgatttt ctaattccta gtcatttttc tattgattgt tttgcaaaag ccatttacat    6780
cttaaggata ttgataatct tttgttatat ttgatgcaaa tatttttttc cagtttatag    6840
gttgcctttt aattttgtgt ttcaggtaga taaaagttaa acgattttct taggttagtt    6900
tatcactgtg gtttctgaac ttgttatgtg tagatctttt ccaccccaag agtcataaa    6960 tattaatcca tactttctta tggaacttgt atggtttcgt ttttacatt taaaccttct    7020 tccccgtggt gtgtgttgtg gaatctgtgt ttgtgtgagg aggggcatgg tgctctcaga    7080
```

```
acccacctcc tgtggccaga gagccctgtc ctgtgagggt ggttgtcaca gtggcagggt    7140
tcaattcaga agaccttgag ggcaggctga tgtttcctga atgggcccct ggttgttgct    7200
tgtccctgac tctccatttc cccatctgag tggatttgga cctaataggg cactggagct    7260
ggttcgaatc ctgactggac tacttggcaa ctttatgtct gggagcaagt tacttaacct    7320
ccccaagcct gtgtctgtga atgcgggta aatgaatgta gatgtttggc agcagctact    7380
ccttgttgag ctctcacagt gaactctcct gcctctgccc tccttcccg cctccctgg     7440 tgcctagcgt caggtctagc cacttcctcc tgggcccctc tccctttct gtggctggct    7500 gcctgcccgc ctggcgctgg acctttcatg taacgggaat cagcatgtat attctggtct    7560
ggtctgtttc tacacttaat tttgtttcca gtagtatttc cctgtaccgg cagagttcac    7620
aaacacattt gaagaggctt tttctcagga ttcttaacct tcccaaagga agtcccatgg    7680
atgggtttct agaagtctat aaatgctctg aaattgtatt tttctgtgga aagcataact    7740
ttcatctgct tgttcgtgct caaaaaagat catgaatgaa tgattgcatg attttatgcc    7800
attgtgctta tactaaagga tatgtagccc atctcttgag ctgttaaact gttttgacta    7860
cttaaaatcg tgcagctgtg agcatctctg taaatttagt gtacacatgt atcccctgga    7920
gtggcattgc ctcggcagtg agcacttatg gtttataac tctcttcaca gactcaaatg     7980
actccagaaa gctacacttc ctgttgtgag tatatgatat ccattcccct acatagccac    8040
taacatcagg ttttttacaat tttatttatt tcttgctact ttaagaaatt tttgtggtga   8100
aatacatata atagaagttg actatctgaa tcatttttaa gtatacattc agtagtgtta    8160
agtatgtcgc cattgttgta caaccaatct ccagaacttt ttcatcttgc aaaacaaact    8220
ctgtacccat taaataacat taaacattcc attccctcca gcctcagcaa ccccattcta    8280
cttctgtttt ctgtgagttt gactattcca agcacttcat atcagttaaa tcatgaagta    8340
tttgtctgtc tgtgactggc ttatttctct gagcacagtg tcctcgagat gcgtctatgt    8400
tgtagcatat gtcagaattt ccttcctttt taaaagatcc aaataatatt cttatttat    8460 atcttttttt tatccattca tccattagtg gacacttggg ttgcttttgg ctattgtaaa    8520
taatggtgct atgtacaaat atctatatta ttgtatttac aagtataatg ctgtaatgta    8580
cacacatctt tttgagatcc taccttcagt tcttttgagt atatagccag aagtggtatt    8640
actaaatctt acgatatttc tatttttaat ttattgagga accactgtag ttttttcatag   8700 caactgcacc attttacgtt ctcaccaaga gtgcacaagg gttccgaggt tcccacatcc    8760
tccccaacac ttgttatttt ctgctttttt tagattgcag ccatcatagt gggtgtgagg    8820
tgacatttca ttgtggtttt gatttgcatt tccctaatga ggagtgatgc tgagcatctt    8880
ttcatatgct tactggtcat ttgtatgttg tctttggaaa aatgtctatt caagtccttt    8940
gactatttta aaaattgggt tattagagtt atcgttgttg ttgacttgta ggagtttctt    9000
tctatattct ggatattaat cccctatcag atatatgatt tgcaaatatc ttctcttatt    9060
ccataaggtt actttttcac tttgttgatt gtgttctttg atgtatagaa gttttttagtt   9120 ttgaaatagt ctaatttatc tgtttttact tttgtggtct gtgcttttgg tgtcatatcc    9180
aagaaatcct tgccaaatcc aacgttataa ggtacttttta aggtatttta gttgtcttag   9240
tctatatttc tgtactcacc tttctttatc cactcatcag ttgatgggca tgtaggttgg    9300
ttccatatct ttgcaattct gaattgtgct atgatcaggt gtcttttag tataatgatt     9360 tactctcctt tgggtagata cccagtagtg ggattgctgg atcgaatggt ttttataatt    9420
```

```
ttctattta ccacagtttc tctctgcatt tttcctctctt gaccactaac catgtgaaat   9480
tctcatattg acctttataa tgatcatgaa ctcttagtat cattgggaag gccacatttg   9540
ccacttatga ttgtaaacct tatcctccat ttttcctgtt attgttggtg caaaaagcac   9600
ctattatacc aggactttaa aaatcagtct gataagtctt tgataagtct aataataata   9660
actgataagt ccattgaatt tgcttctgat tacttttct ttagtagcta aacatgtatg   9720
tactcctatg attacaatga acactcctct ccatttaaat taattattta cattgatgaa   9780
atagcaaaat gttaatgact aaatactgtc ttggtttttt cgttccaggt cagtcaatat   9840
taacttctta taattttctt ttttttcttt atgtgtgtgt gtgtgtgtat tttttttttt   9900
ttaatttcaa tggcttttgg ggtacaaatg cttttggtc atatagatga attctacagt    9960
agtgaagtct gagattttac tgcaccggtc acctgagtag tgtacattgt acccaatatg  10020 tggttttta taccttgccc ccctcttacc ctccccactt tgagtctcta gtgtccatta   10080
tgtcactctg tataccttt tgtacccata agttagctct cacttataag tgagaacaca   10140
cagtatttgg ttttccattc ctgagttgct tcacttagaa aatatcctc cagctccatc   10200 caaaattgct gcaaaaaaa aaaaaccac aacattatt ttgttctttt ttattgctaa    10260
gtcatattcc atggtgtaga gataccacat tttatttatc cactcactgg ttgatgggtt   10320
ggttccacat ctttgcaatt gtgacttgta ctgccatcaa gtgtctttct ggtataatga   10380 cttctttttcc tttgggtaga tacccaggag tgggattgct agatcaaatg gttcttaaca   10440
ttttctctct ggatctattt ctggaaattt taggctccag tttttgttgt tgttgttaat   10500
aaaatgcaat ggaatgtaat gatcatcact tttcattatg cttaaaaatc tggtaaatgg   10560
aggctagaac actcctgtaa ggcaagaata ttctctctgt tggaactcaa atacacagaa   10620
ctgggtaaat ctcaatctta atctttgatt caggacacaa catggctctc ttttacttgc   10680 tttcttaat tgttttttaa taatgtggta agcatttctg aatctcctat ccaatacaaa    10740
aactaggaca atacagacag taactcctat ggttacaatg aacactcctc tccacttaaa   10800
ttaattattt acactgatga aattgaaata gcaaaatttt aatgactaaa tactgtcttt   10860 gatttttgt tccaggtctg tcaatattaa cttcttataa ttttcttttt ttttctttat   10920
gtgtgtgtgt gtgtgtgtat atatatatat ttaatttcaa tggcttttgg ggtacaaatg   10980
gcttttggtc atatatatga gttctacagt agtgaagtct gagattttac tacaccttcc   11040
acttatgtgg tcccacacca cccgcctccc ctgccgcctc ctgccacccc ctaggccaag   11100
gtaataatca tcctgaatcc tgggtttatc tctcacttgc tttctttttca tataattttg   11160 caaaagaatc tgatctaaat gtgttttca gagtatatat ttatattta gctgttctta   11220 gagaaaattt attattttgc atgtaatctt atggaacatt ctcatttaat accatggtaa   11280
gattcagccc ttgcccaggg gatagttcat ttagtttgtt tactggatag agctcatcat   11340
gtgactatac ctcagttagt ttatcagttc tcccatccat ggtgactagg ttgcctctca   11400
gcctctcaac aacactgttt ctcagtgtcc ttgtagaagt gatatgtggg tgttttctcc   11460
ttacacagag ttgaaaggtg acgacaacaa cgttggcact accaatcccc caccctccag   11520
aggggtaacc agtgttacca gtttgctgtg tttcctgcta cacctcgcct tattcacttc   11580
catttgtatc tgaaaaacgt gttgcatggt ttctttctcta tagaagtggt aaaatgctat   11640
tgtgtcctgt acattattga ttactttttt tcatttaaca gtagggagat gcctgggagt   11700
acacagagaa ctgccctcat tgttttcaac ttctgcactg tatgtctgtg agtttagcca   11760
ttctgctgtt aatggaaatt tacagtattc taatctttg atattacaaa cagttctgtg   11820
```

```
cgatcatcgt catacacaac cccttgtgca caatgcatga gtgtttctca gggtaggtac    11880
caagaagtga aattcctggg tcatagggcg tgagtccgac attttctcc attctgccct     11940 gttgccctcc agagtgggtg tccagctttg catacctaag tatgagagta tctgttgttc    12000
atatcctcta cgacgctcca tatatgaaac ttaagtttct gctagttgcc atctttgatc    12060
tatcatgtat gcagtgacct actaagactg taattggtac agtagattct tgtcatctgt    12120
gtgtgaattt agcattcatg ggcttaatgc tgacaaggcc cccagggtcc aagcacatata   12180 atcatgtata attttgtcaa ggtataattt tttaaattgc ttttgtcatg tgtctgctgg    12240
tgatgcccaa cccagtgctc tgcacccagg tcacactgtg gctttgtcct ctgcttatgc    12300
ctgcattgca gcaactgtcc tgaagagacc aaaattatgc agatttaggt aagtccatgg    12360
ctaatgttat tatattatgt gctattgtaa tggatgggc tgtggagtgt atgaatttat     12420
aaatcactgg tcttgtaatt aaaattcaaa cactatagaa aaaggccatg tagaagataa    12480
aagttcctct ataatcccgg acccctaaga taactactaa tgacaacttc atttatattc    12540
cttcagacat tttctggctg tggatgtact aaaatgtatc ctattattct ctgccctaaa    12600
atggaatcat acaaggtgta ctgttatttt tatggctcta taacatgtca tattgtacgt    12660
gttggtatgg tcattttaac cattttctc gtgatggctt tgaggttatt tgcagtttcc     12720
tagccatctc aaagtgtgct gcggggatct cttttgcatc cctctgggtg cagagctgag    12780
gcacccagag gcagtgtcca gaggaggcag catctgtagg tgtcttcacc tgctctggct    12840
cttggcacat ctggttggtg acactgtttt gtgagatggg ttgaaagcac gtgctgccaa    12900
aatagaataa tgttggtcct ctcctcatgt gccgtggaac tggggtaaaa ctgcgtagtg    12960
gctgcagctg cctgtccata ccggaatcga gtataacacg tgcctggct agcacaaaa     13020 cagtagtggg tcctgcaggc cccagagtct aattcctggt attcttccc ctacacagat     13080 taaataaacc aaaacaaac tattctagga aagcgtctgt gacatttgta aaaagtggta     13140
tttaatgatc tttattcac ttgtctgttt agtttgttga aatcttaagt ggcatcctgg     13200
tctgggaagg agtgctgtct gcgcctgccc tccgctgggc acagcgtggc tgcttcaggg    13260
gctaagcaca cactttctgt cttctaaagg gccgccacat gccaggagct caggtgtgag    13320
cccggctctg gctcttacct catagggtca ctcatagggg cacagggagc agaacattgt    13380
acacagcgag gcaccacccg gcttggcatc tgcctcggtg gacttactac ctctagaagg    13440 aaataccctga gttcctctgg cctcagctcc tagagtgact ggtgtgctgt ccctgttact   13500
cttctgtcaa ggtgacaact gtgtgaccca tcatctgtgt gtcaaagcaa ggccctgcct    13560
gggcctctgc tcctgtgctg accccaaagg caaatgcttt gctagtttcc ttccagttaa    13620
tttcacctat gaatagatgt gtgaaaactg ttcaaagcca tacctgcaca tgtttgaact    13680
tcaaaccctg tgggtgattc agtggcatct ttctctaacc cccagcctcc cttcccacag    13740
aggccaccgt catggccagt tgctgcagtt tcttccaga gaacctgtgt atgtgtaaag     13800
ctgtacaggc gtgggtacac cacacagcct gtcttgcact gtggactgtt gagttactag    13860
tacatctagg taagcaccgc atatctgtat tcatgtctgc cttggtcttt tcaacatctg    13920
tgtggtagcc gtgtttgaat tacccattcc ctttttgggg aaccattaag ttgtttcagc    13980 aattttact gtagataagg ctataccgca tatctgtgta catgggtttt tatgtacatg     14040
ggcaagtata tctgtgagag aaaagttttcc tcaggaggaa ttctgggcac agcatgtgta   14100
aatttctaaa tatgatggac accccagct tccacctcaa ggaggttggt cccattgaca    14160
```

```
tttccccaca ccttcaccca ggctgtgccc ttaaacttgg ttatttgtca atgtgagaag    14220
tggaaaatag tatttaattg tagtttggat ttgtatttct attgggttgt atacttactg    14280
attaataata agagctcttt acatattaag gaaattaacc cttttcaaat acattcctat    14340
ttctcactaa tctttaagtt ttattgtaat attttgctct ttagtttata tatatatgta    14400
tatatatata tatgtatata tatatatata catatatata tacatatata tatactaatt    14460
ttcttttatg gttcctggat tttgtgagta gtttgaaaag gctaatccag ctgaagattt    14520
tgttgttgtt gttaaacccc atgttttctc ctaactcttt ttatttttat tttggaggac    14580
tctatctaga cttaatttta gcataacaag tgacagggtt agttagcctg ttgtccttac    14640
accatttcct ggctaataca gctattaact attgatctgt ctattcacgt gccagttcct    14700
aatggtttta catagtgtaa tctgcacttc aaaatagcga agggaagccc tacctcatta    14760
ttctactttt ccagaattct cctggctatt ccaggctgca tgtttacctt aaccttccct    14820
gtgatgtctt catgccgttg tcttcttatg caagaataag gtacgtcttt ccatccactc    14880
acgtctattt aatttgactt tgcattacac agaaagctgg tcttggtctg tctacctcgg    14940
catctagttg tcctcactgc cccctagccg accccacccc atctgactga ctaccccatc    15000
acagagtact tttatttacg ttttgctctg cctaatggtt acttgatact gtcacgccga    15060
cagtgtccag ttcagtggtc tttgcagttg aaatgctccc gtacacactg tcttgttaaa    15120
aatgccagta agttcataca aacccagctt gcacccaagg tcacattcag agagcgtagg    15180
gctgggatgg gttgttttcc aagcttctgc cactgtgtgg ctagctcttc ccactgggaa    15240
gttctgtgta cccggaatgt cggagtggag tcctgttcta gtgtccagca cctgaccctg    15300
tgcccaaccc ctcaacagcc tattcctgct gtccacagcc tgctggaact ttttacaaaa    15360
tatgttgcca tgctggaccc tgggcactgg acataagccc cctggcagcc ttttcatgt     15420 cacccaaagg ggtaattgtc ctactggtgg tctgtaagat gagttagggt gacttgctaa    15480
tagacattgt aaatcttaat atttatgtat gtatttatt attaccggtt ttccatttat     15540
gatggtaata ttgtttcttc taagaatatt tattttcct tctaaatatt gagataaaat      15600
tcatgctttt gaaatgttct attcagtggc ttttagtata tttgctatgt tgtgcaacca    15660
tcgacactat ccatttctag aacttttcg tcatcccaaa cagacgctct gtattcataa     15720
aaaaataact tcctacctgt ctctcccct agtctttggt aacctttgtt atactggtaa     15780
actttgttgt gctctctgtc tgtgtgaatt tgcctattct aggggcctca tataagtgta    15840
atcatacagt atttgtcttt ttgggtctgt ctgatttcac ttagcgggtt ttcagggttc    15900
attcatgttg cagcatataa cagtactgcg ttcctttttc tggctgaata atattccact    15960
gtatggatag accccatttt gtttattcac acatcatttg gacatttgga ttatttctgg    16020
tttttggcta ttatgaacaa tggtgctatg aacagttgcg tacaagtttt tgtgtgaaca    16080
tatgttttca attctctcat tatataccta ggagtagaat tactgggtca tatggtaact    16140
gtatattttt gaggaactgc caaactattt tcccacgtcc atgcaccatt tcacattccc    16200
accagtaagt aagagggttc caatttctgc gcattcttgc caacactagt tattatctga    16260
ctttctggtt ataatcattc taatgagtgt gaagtagcct ctggtgtcat ttggatttgc    16320
atttctctga tgagtgatgc tatcaagcac ctttgctggt gctgttggcc atatgtgtat    16380
gttccctgga gaagtgtctg tgctgagcct tggcccactt tttaattagg cgtttgtctt    16440
tttattactg agttgtaaga gttctttata tattctggat tctagaccct tatcagatac    16500
atggtttgca aatatttct cccattctgt gggttgtgtt ttcactttat cgataatgtc     16560
```

```
cttagacata taataaattt gtattttaaa agtgacttga tttggctgtg caaggtggct    16620
cacgcttgta atcccagcac tttgggagac tgaggtgggt ggatcatatg aggaggctag    16680
gagttcgagg tcagcctggc cagcatagcg aaaacttgtc tctactaaaa atacaaaaat    16740
tagtcaggca tggtggtgca cgtctgtaat accagcttct caggaggctg aggcacgagg    16800
atcacttgaa cccaggagga ggaggttgca gtgagctgag atcatgccag gcaacagaa     16860 tgagactttg tttaaaaaaa aaaaaaagtg acttgattta agggaaaaaa tgactggcta    16920
tattcagtca gatatggcaa aaagtctcaa ggtgttaatg tgaatgatta aggtcttggg    16980
gggggtgtcc cctatcagac tacaggtgtt tagaggcaca gaaaaaggtg cagttgggtt    17040
cttaatgtga aatgatgaga agcacaactc cagtgtgtct ctttgtgtag aatgtcagca    17100
gacaccccct gctagatgtg ctggatcatg ggaaagcatt tccatttgtt actagattgt    17160
tcagaagttt taatttatga tgggtgtggt ggctcatgcc tgtagtccca gcactgtggg    17220
aggctgaggc aggaggatca tctgaggcca agagttcaag atcagcctgg gcaacatagt    17280 gatacccat ctcttaaaaa agaagaagtt tttaaatttg aataataat aggtactgga      17340 tttatgcaaa tgtcttttct gcgtcttttg agatgagtat caggtttttt tttttccttt    17400
tatcatctga tgatgaactt aatgtttcca tttgtattaa tggaatacta agtccctctg    17460
tgatttctga accaagctat tcctaggcct gagttttatt ttgttgacac agaaataaat    17520
tagaaggcca agcgtggtgg catgtgcctg tagtcctagt tgctgaggta agaggattgc    17580
ttgagcccag gagttcaagg ctgcagcaag ctttgattgc gccactgcac tccagccttg    17640
gcgacagact aagacgctgt ctcaaaaaaa aacaaaaacg acaaaaaaaa aacaaaacag    17700
aaaaaataaa ctaaggcaat gacagtccct ggcaaatgct gggagggagg cagcagtggt    17760
cagggaaggt aaccctgaag caggacttgt aaagcaaata agattgggag gccaaggtgg    17820
gtggatcacg aggtcaggag ttcgagacca gcctggccaa catagtgaaa cccgtctt      17880 actaaaaata caaaaaaatt agccaggtgt ggtggtgggt gcctgtagtc ccagctactt    17940
gggaggctga ggcaggagaa tctcgaaccc aggaggcgga ggttacagtc agctgagacc    18000
gcaccattgc actccagcct gggtgacaga gcaagattcc gtctcaaaaa aaaaaaaaaa    18060
aaaaaaacca agaagaaaag gaatgaatta gaacttcttc tgcttggact taagggcatc    18120
atcaggcagg ttttgggtag gatagcaggg gaggcagaga catagtcggg gtcagtggtc    18180
atgagtgtgg ctttgagccc aaaaacttgg tttctgttcc ctactttgcc actcagtagt    18240
gcatgacttt ggccaaattt cttaaattca tgaagcaagt ttccgggtga atgaaatggg    18300
gataaaaata gtgttcaaac ctatccgttg gtttgtgtga aactgaaatg aatagtatcg    18360
tgcaggtact tgtgagcaag gggagctgct gtttcctgtc cctttatgat gggaaatatc    18420
tagacaagtt cccaaccctc tgcactgcag gctgcatggc acggagggtc ttgtaacacc    18480
agctggggct ggccttcttt taggagcttc agtggtctg aaaactttta tttgtttgtt     18540
tgttttagta gatgtggggt ctttctgtgt tgcccggact ggtctcaaac ttctggactc    18600
aagtgatcct cccccgctca acctcccaaa gtgttgggat tacaggtgtg agccactgtg    18660
cccagccttg aaaactttt caggttcttc cagggttact gggctattaa atatttctat     18720
ttcattataa gtcagttttt caaagttata ttatcttaat taccttttt atatgtatta     18780 gtgtagagta gcattttata ttttgatatc ctccttatgc atagttttc acttttatt      18840 cctagttttt cgttttaat aagactttca agaaatttat tttattggcc ttttgaaaaa     18900
```

```
agcagcttta gataaagtaa gcagttctgc tttcatttta taatttattt ctactttgt    18960 ttcattaatc ttttcctccg gcatgccttg gattttgttg tgttactctt tttctagagg    19020
ctcgcattgt gtgtctggtt cacttatgat cacgcttgcc tacttttaag aatggaagag    19080
gggaggtgga gggtggctgc acagtcgagg gtgtgaggca gtcttgctct agccccacca    19140
tgccctcagc ccgctgtggc cacgctggtt cctcaattgc tggggcgtgc agtgtctgta    19200
agggaggcta ctgatgccat ccgaggaaga tgtaaggttt cgtgtgggca gcgagagcct    19260
agcaggcatg tggggtgccc agcaaagggt aacagtggac agttgttgcc tcattccaca    19320
gagttttgat tttttttttt ttttttaatgg tcactccatc aacatccccc atggccagag    19380
cctgagctgg tccccagaga cacaggcatt cagctgacag cctcgccttc acgctgctgc    19440
tgttctcatg ggggacaggc ctcaggtggc aatgcacaaa tcattagtta agggcagttg    19500
tgacagttac caaggagtgt agtcccccgc ccccgccca gtgaaaacag ccctaaccag    19560
gggtggggac ctttgggctc tgacccgaag ggtaggagaa gctggaagga cagcattcct    19620
gtctgcgaag gcaggagcaa agctgccagg ctatgaagga aatggctgga gcctgaagtc    19680
atgcaagctg gggctggcag ggacagggcc aacttccagg cctgggggcc accatgagga    19740
ttcaggacgt gaccccccagg gcacatgaag gccttccatc tgtatttaag aaaagacttt    19800
atcagacgag tatggtggct cacgcctgaa tcttagcact ttgggaggct gaggcaggtg    19860
gatcacgagg tcaggagttc aataccagcc tggccaatat ggtaaaaccc catctctact    19920
aaaactacaa aaattagcca ggcatggtgg cgcacgcctg tagtcccagc tactcgggag    19980
gctgaggcag aagaatcact tgaacccggg aggtggaggt tacagtgagc caagatcgcg    20040
ccactacact ccagcctggg tgacagagtg agactccgtc tcaaaaaaac caaaagactt    20100 tatcttatttt cctatatgtt tgtggtttca gtcctgatgt ataatttgac cctagttaga    20160
atggttatct gaggaagtgg cctgtacgat ttctgctttt taaatgtgt ggctcccttt    20220 cttcattgat taacgtatga ttattttat aaatgttcca tggcagtggg aagggattct    20280
ctgtcacatt ccacatctgg atcagttcct ccccattttg ttggtcaaat ccgatctgcc    20340
atatcctgtg taatgacaag tgagttgcat tctcaccgtc actcctgggg tctctccgct    20400 tccctgagc tggctcagca gtctgctcca tgtgttttga tgcagggtga cccattggta    20460 ttccgacac taacgccccc gtctgtggac tgcttgctgc ttgggcttca ctgtgtctgg    20520
tgttgacagt gcagacctaa aggtgtgcac acatgtgcac acacactccg ctgtcttctt    20580
gtttgcactg gacttaaata tctatgaggg ttatttttcaa ctgctgaatt tggaatgatt    20640 tttatatcctt ttctgctttc tgcccatgta catgtgttta ttttacactg ttgtgattgg    20700
tagttactat gtggggacac aattacttgg gctgaaataa tccacctgtt gtggttgggg    20760
tcctctgggg cattccaggg tgagaggttg tcactgccac ctgggccatg tgggccggca    20820
ccagcatttt gtggttacga attctacagt cacaaatatc tttgggcaaa tcccccttcta    20880 tacctcaagg cagcttttgg tttgcaaccc cactggccag agggaagggc cagtcacttg    20940
gctctctcac tgccctgcgc cccagatggt tctagggctg ctgttttccc ttggccctgc    21000
caacaccact gttttactt ctgctcattg gctgagtgca gtggttcctg gaagccagtg    21060 gcacgttcc ccgcgtagct cgcttatccc acagcacaca cccaagggtt ctgttgctaa    21120
cacgctgaat taattctttg ctcatcttac agagtgtgtt ttgactgccc ccatttctga    21180
ggccttgtaa ggccagagct tgttgcttc atcggcaggt tgggacttag atggccgtga    21240
atgtttcctc tctgctgctg cagtaagtaa gtgcccgcac catagtgtgt ttggaggctg    21300
```

```
aagttgaagc gaggctgtga ggggagatgg acgtgtgagg agggatgatg gggcttgagc   21360
aaagtggggg aggggggcaaa ggcagttggc ccaacacatt ccccacccct ttgagaggtc   21420
tgaggcctgc agacctggct cggagcccac ctggtagtcc tcagactgtg tgtgtgtgtg   21480
tgtgtgtgtg tgtgtgtgtg tgtgtgtgtg tgtgtgtgtg tgtgtaaaag agagaagttg   21540
tggagaaatg gggggctgat tctgctcaga ttcatcagga tgagtagaag gcacccagct   21600
ctcaccctgg cctgacatgt gtgtccctga gcaggttaca gtcctctctg agcctctgct   21660
tcccatctgg accctgctgg gcagggcttc tgagctcctt agcactagca ggaggggctc   21720
caggggccct ccctccatgg cagccaggac aggactctca aatgaggaca gcagagctcg   21780 tgggggctc ccacggaccc gccgtgggcc caggggaggc agagcctgag ccaacagcag   21840
tggtgctgtg gaccgtggat cctgagggtg gcctggggca agtaccggct gagggtccag   21900
gtgggctttg tgtacctttg ggtcctgggg ccctggtgac ttggactcca ggttagagtc   21960
aagtgacagg agaaaggctg gtggggccct gtgcttccga cttcatttcg agtgatggca   22020
gttcccagga aggaatccac agctgacggt ggctgacaga tcagagaatg aaggcgagg   22080 caggcgggcg tctgcgtgac ctcaggtgct tggggcccag cagacccaga gaaccatttc   22140
cactaggcca gggtgccgga agtgtccaca ggtcttagat tccctgttca gatgaaaaga   22200 tttgtgccc taatgataaa agtgatctgc atagagtcaa aaattcaagc catgggtata   22260
aaatgcaagt aaaatccctg ccctcaccta tcccacccta ctacacagag atgtcctctc   22320
gagtttccta gactcactct ggaaatttct gtatacacac agaagcttgt gcctctgctc   22380
gtgaaggcag agggagggag agctgaaggg ccagcacctt ctcacctgtg ggccccctca   22440
gtgctcggtc ccagagcatg caggactgtg cctcgtgttc agtttgctgg tctgacttca   22500
tgctccttgg gcaggatatg catgtgccat gctaggagac atgtggatgt gaagctgggg   22560
gacaatgtcc cctggctatg cctttacaag ggaagtaagg aaggtaggag gtgagcctgg   22620
gagggaggga gggaggcgcg gagccgccgc aggtgtttct tttactgagt gcagcccatg   22680
gccgcactca ggttttgctt ttcaccttcc catctgtgaa agagtgagca ggaaaaagca   22740
aaa                                                                 22743

<210> SEQ ID NO 3
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 3
ugguaauggu ggaggaagau u                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 4
gugagaaguu gcuuagaaau u                                              21

<210> SEQ ID NO 5
<211> LENGTH: 21
<212> TYPE: RNA
```

```
<213> ORGANISM: Artificial Sequence
<220> FEATURE:
<223> OTHER INFORMATION: Synthetic Oligonucleotide

<400> SEQUENCE: 5
ggaggaguca ggaggaauau u                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 6
ccaaauaggc uuacagauau u                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 7
agagagaagu uguggagaau u                                              21

<210> SEQ ID NO 8
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 8
tcatggaccg tggtttgtta ctatagtgt                                      29

<210> SEQ ID NO 9
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 9
gttcttagcc tgatgaaata acttggggc                                      29

<210> SEQ ID NO 10
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 10
gtgagaagtt gcttagaaac tttcc                                          25

<210> SEQ ID NO 11
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 11
ctggtatgtt gctctgtatg gtaag                                          25
```

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
caacccgctc caaggaatcg                                           20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
tttgtgcttg gaaccttgct                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
tcaacgcccc aagttatttc                                           20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
tctccatttc cccatctgag                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
cagccacaga aagggagag                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
ggcagtgacc ctgacaagtt                                           20

<210> SEQ ID NO 18
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 18
tctgaaggag cctttctgc                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
ccatctgacc ttggcacttt                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
caacccacct tggtctgact                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
gggaactccc ttcctcagtc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
cagcctcctg accacaactc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
aattttccag atgtcctgcc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
aacagtgctt tttgggatcg                                              20

```
<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
tcattggtca tggcttagca                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
agccattttg tctcctgcac                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
actatttcaa ccgccacgag                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
tgcctgaggg ctctagtcat                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
gagaacatcg aattagcgtc                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
gactatcaga cgcctaagat                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 31
ggtacgtaac gaggaagcga                                                   20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
tgcggatatt ttccatgcag                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
agcccttggt ctggaaaaaa                                                   20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
aagcgttggt caatgttgtc                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
tcgccatgag gaacactata                                                   20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tgcagcatct gaaaaccttt                                                   20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
cacaacacaa tgacaccctt                                                   20

<210> SEQ ID NO 38
<211> LENGTH: 20

<212> TYPE: DNA
<213> ORGANISM: Artificial Sequence
<220> FEATURE:
<223> OTHER INFORMATION: Synthetic Oligonucleotide

<400> SEQUENCE: 38
actgtatctc taaccaaccc                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
ccaggaggaa gctggtaaag                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
gatgtgtttc taaggcacga                                          20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
ccattggtat tactttacca                                          20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
ttatttgtgc tgtaaagggg                                          20

<210> SEQ ID NO 43
<211> LENGTH: 21
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (20)..(21)
<223> OTHER INFORMATION: n is deoxy-T

<400> SEQUENCE: 43
gccuuuacua caugugugan n                                        21

<210> SEQ ID NO 44
<211> LENGTH: 21
<212> TYPE: RNA
<213> ORGANISM: Artificial Sequence
<220> FEATURE:

```
<223> OTHER INFORMATION: Synthetic Oligonucleotide
<220> FEATURE:
<221> NAME/KEY: misc_feature
<222> LOCATION: (20)..(21)
<223> OTHER INFORMATION: n is deoxy-T

<400> SEQUENCE: 44
ucacacaugu aguaaaggcn n                                              21

<210> SEQ ID NO 45
<211> LENGTH: 21
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (20)..(21)
<223> OTHER INFORMATION: n is deoxy-T

<400> SEQUENCE: 45
cuuagaacuu uaagugcaan n                                              21

<210> SEQ ID NO 46
<211> LENGTH: 21
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (20)..(21)
<223> OTHER INFORMATION: n is deoxy-T

<400> SEQUENCE: 46
uugcacuuaa aguucuaagn n                                              21

<210> SEQ ID NO 47
<211> LENGTH: 29
<212> TYPE: DNA
<213> ORGANISM: Artificial Sequence
<220> FEATURE:
<223> OTHER INFORMATION: Synthetic Oligonuclotide

<400> SEQUENCE: 47
acactatagt aacaaaccac ggtccatga                                      29

<210> SEQ ID NO 48
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 48
gccccaagtt atttcatcag gctaagaac                                      29

<210> SEQ ID NO 49
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 49
ggaaagtttc taagcaactt ctcac                                          25
```

```
<210> SEQ ID NO 50
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 50
cttaccatac agagcaacat accag                                        25
```

NEAT1 AS A PROGNOSTIC MARKER AND THERAPEUTIC TARGET FOR PROSTATE CANCER

CROSS REFERENCE TO RELATED APPLICATION

This application claims priority from U.S. Provisional Application No. 61/980,825, filed Apr. 17, 2014, the entire contents of which are incorporated herein by reference.

STATEMENT REGARDING FEDERALLY SPONSORED RESEARCH OR DEVELOPMENT

This invention was made with Government Support under NCI R01 CA152057 and NCI U01 CA111275, awarded by the National Institutes of Health. The Government has certain rights in this invention.

INCORPORATION BY REFERENCE OF SEQUENCE LISTING

The Sequence Listing in an ASCII text file, named 31008—6063—03—US—Sequence Listing.txt of 44 KB, created on Oct. 13, 2016, and submitted to the United States Patent and Trademark Office via EFS-Web, is incorporated herein by reference.

FIELD OF THE DISCLOSURE

This invention relates to diagnosis and prognosis of prostate cancer, as well as therapeutic treatment of prostate cancer. More specifically, this invention provides diagnostic and prognostic methods based on detecting NEAT1 levels in a sample. The invention also provide methods for treating prostate cancer based on targeting and inhibiting NEAT1.

BACKGROUND ART

The androgen receptor (AR) plays a central role in the progression of prostate cancer (Heinlein (2004)). Androgen ablation is highly effective in treating metastatic prostate cancer, though resistance inevitably develops leading to castrate-resistant prostate cancer (CRPC). Most cases of CRPC remain dependent on AR signaling, which has led to the clinical development and recent approval of potent AR-targeted therapies for CRPC (i.e., abiraterone, enzalutamide) (de Bono (2011); Scher (2012)). However, similar to first-generation anti-androgen therapies, patients develop resistance to these second-generation hormonal therapies. How CRPC tumors bypass AR signaling is emerging as a significant area of investigation.

In CRPC, crosstalk between estrogen- and androgen-signaling pathways may present an opportunity for clinical intervention. Estrogen receptor (ER) signaling through ER alpha (ERα) increases with prostate cancer progression (Ricke (2008); Clemson (2009); Rhodes (2007)) and can drive important oncogenic events, including TMPRSS2-ERG expression. Although ERα signaling has been extensively studied in breast cancer (Barwisck (2010); Best (2005); Glinsky (2004)), our understanding of the potential impact of this nuclear receptor on prostate physiology is less clear. Nevertheless, the connection is a particularly intriguing concept given that most cases of prostate cancer arise in the sixth decade of life, a time when testosterone levels are decreasing and estrogens are increasing in men. Mouse models suggest that antagonism of ERα may diminish prostate carcinogenesis (Ricke (2008))

SUMMARY OF THE DISCLOSURE

The inventors have demonstrated herein that ERα is recruited to both coding and non-coding regions of the prostate genome and orchestrates expression of non-coding regulatory RNAs. Amongst putatively ERα-regulated intergenic long non coding RNAs (lncRNAs), the inventors have identified Nuclear Enriched Abundant Transcript 1 (NEAT1) as the most significantly overexpressed lncRNA in prostate cancer. Analysis of two large clinical cohorts has revealed that NEAT1 expression is associated with prostate cancer progression. Prostate cancer cells expressing high levels of NEAT1 were recalcitrant to androgen or AR antagonists. Further, the inventors provide evidence showing that NEAT1 drives oncogenic growth by altering the epigenetic landscape of target gene promoters to favor transcription, and that knockdown of NEAT1 decreases proliferation and the invasive properties of the cells. Accordingly, this invention provides diagnostic and prognostic methods, as well as therapeutic methods, for care of prostate cancer patients.

In one aspect, this disclosure provides a method of determining a risk of developing prostate cancer in a subject who does not yet have prostate cancer, by detecting the level of NEAT1 in a biological sample from the subject, comparing the level of NEAT1 relative to control, and determining the risk of developing prostate cancer in the subject based on an elevated level of NEAT1 in the sample as compared to the control.

In another aspect, this disclosure provides a prognostic method for determining a risk of advancing the prostate cancer in a subject by detecting the level of NEAT1 in a biological sample from the subject, comparing the level of NEAT1 relative to a control level, and determining the risk of advancing the prostate cancer based on an elevated NEAT1 level relative to the control level.

In still another aspect, this disclosure provides a diagnostic method for determining the stage of cancer in a subject by detecting the level of NEAT1 in a biological sample from a subject, comparing the level of NEAT1 relative to a control level, and determining the cancer stage based on an elevated NEAT1 level as compared to the control level.

In a further aspect, this disclosure provides therapeutic methods for treating prostate cancer based on providing to a subject with an interfering RNA molecule that targets NEAT1. The methods of this invention are particularly useful for treating a patient having an advanced stage prostate cancer, including patients showing resistance to hormone therapy. In some embodiments, the interfering RNA molecule is an siRNA molecule, for example, an siRNA molecule comprising a strand that is complementary to any one of SEQ ID NOS: 3-11, 43 or 45. Delivery of the interfering RNA molecule can be achieved using a delivery vehicle composed of nanoparticles.

In another aspect, the disclosure provides therapeutic methods for treating prostate cancer based on providing to a subject with an interfering RNA molecule that targets NEAT1, in combination with another therapy targeting androgen-receptor mediated functions.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

DETAILED DESCRIPTION

Figures 1A, 1B, 1C, 1D:
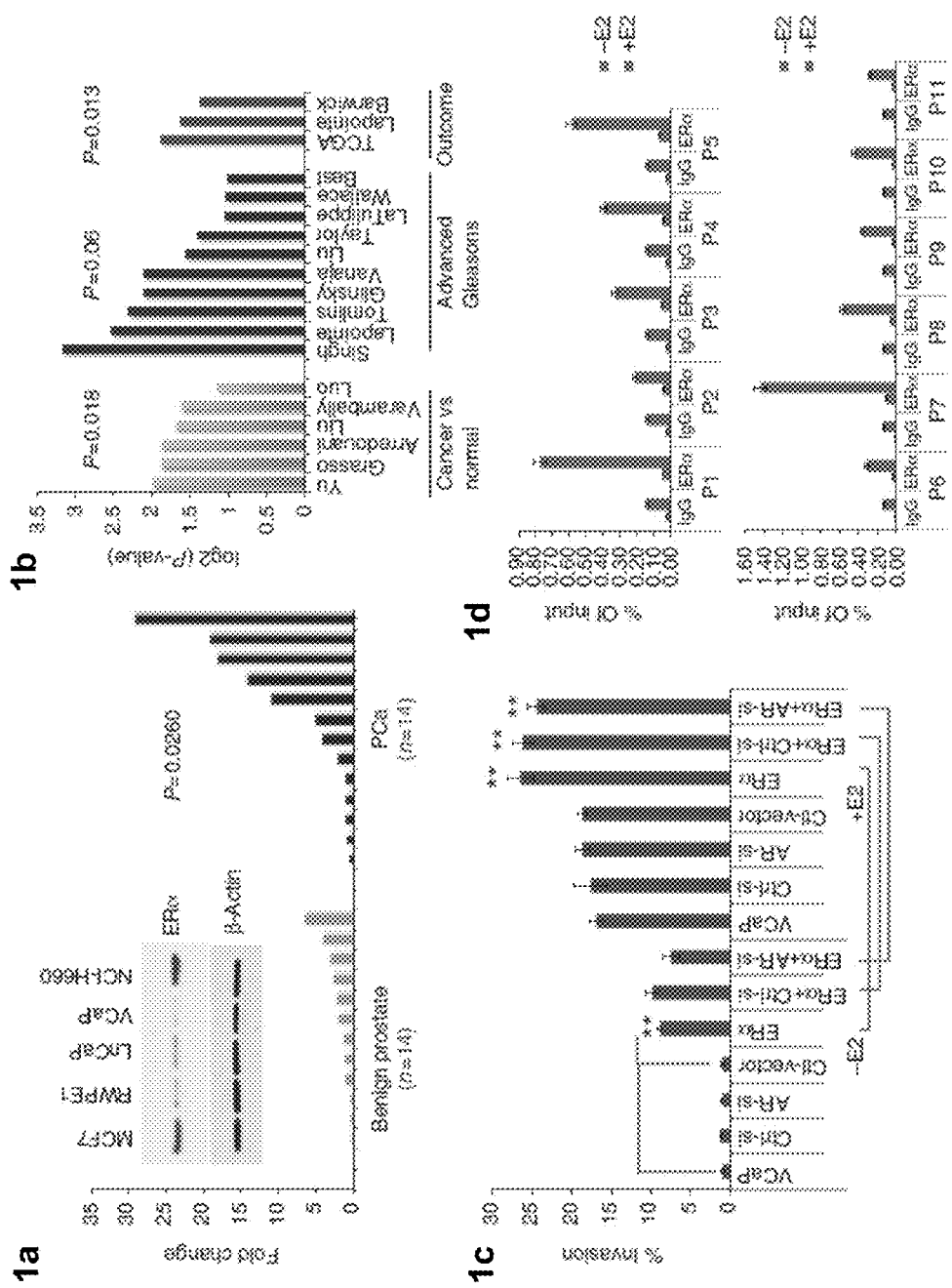
FIG. 1a-1f. ERα plays a distinct role in prostate cancer. (1a) ERα is upregulated in prostate cancer compared with matched benign controls. Waterfall plots depict the qPCR expression levels of ERα mRNA in an independent cohort of benign (n=14) and PCa (n=14). (inset A) The expression of ERα in different prostate cancer cell lines was determined by western blotting and compared with MCF7, a breast cancer cell line. (1b) Analysis of ERα expression in Oncomine public datasets of normal vs. prostate cancer and advanced disease. (1c) Invasion of VCaP and VCaP ERα cells analyzed 48 hrs post-treatment with vehicle control or E2 (10 nM) in presence of control or AR-siRNA. Results are expressed as the mean±s.d. of three independent experiments. Student's t-test was performed for comparisons (% Invasion) between −E2 and +E2 conditions for ERα, ERα-Ctrl siRNA and AR-siRNA and *p<0.05 and **p<0.01 was considered statistically significant. Error bars represent the range of data. (1d) Recruitment of endogenous ERα to target gene chromatin was analyzed in VCaP cells with or without E2 treatment. Results are expressed as the means of percentage of input±s.d. of two independent experiments. Error bars represent the range of data. (1e) Computational pipeline for identification of ERα-regulated lncRNA supregulated in prostate cancer: A schematic overview of the methodology employed to identify ERα-regulated lncRNAs that are differentially expressed between benign vs. prostate cancer and prostate cancer vs. NEPC. (1f) Box plots show expression levels of the top three ERα-regulated lncRNAs from 26 benign and 40 PCa cases, with ideogram depicting their chromosomal position. Waterfall plots depict the qPCR expression levels on an independent cohort of benign (n=14) and PCa (n=14) of the three nominated lncRNAs: NEAT1, NR_024490, and FR349599.

The present inventors have identified NEAT1 expression is associated with prostate cancer progression and a high level of NEAT1 is indicative of prostate cancer, particularly prostate cancer at an advanced stage. Further, the inventors have demonstrated that NEAT1 drives oncogenic growth by altering the epigenetic landscape of target gene promoters to favor transcription, and that knockdown of NEAT1 decreases proliferation and invasive properties of cells. Accordingly, this invention provides methods for diagnosis or prognosis of prostate cancer based on detecting the levels of NEAT1, and methods for treating prostate cancer based on inhibition of NEAT1.

NEAT1

The term "NEAT1" is the abbreviation for nuclear enriched abundant transcript 1, a molecule also known as multiple endocrine neoplasia 1 (or "MEN1"). The NEAT1 gene is located on chromosome 11q13.1 and produces two long non-coding RNA (lnc RNA) isoforms, a short isoform of about 3.7 kb referred to as NEAT1_1, NEAT1 v1, or MEN epsilon, and a long isoform of about 23 kb referred to as NEAT1_2, NEAT1 v2, or MEN beta. The sequences of the two isoforms (SEQ ID NO: 1 and SEQ ID NO: 2, shown below in their DNA counterparts) completely overlap at the 5' end (i.e., the 3729-nucleotides sequence of the short isoform is identical to nucleotides 1-3729 of the long isoform).

```
Short isoform (3729bp)-Homo sapiens nuclear
enriched abundant transcript 1 (NEAT1) mRNA,
complete sequence, GenBank #EF177379.1
(SEQ ID NO: 1):
GGAGTTAGCGACAGGGAGGGATGCGCGCCTGGGTG

TAGTTGTGGGGGAGGAAGTGGCTAGCTCAGGGCTT

CAGGGGACAGACAGGGAGAGATGACTGAGTTAGAT

GAGACGAGGGGGCGGGCTGGGGGTGCGAGAAGGAA

GCTTGGCAAGGAGACTAGGTCTAGGGGGACCACAG

TGGGGCAGGCTGCATGGAAAATATCCGCAGGGTCC

CCCAGGCAGAACAGCCACGCTCCAGGCCAGGCTGT

CCCTACTGCCTGGTGGAGGGGAACTTGACCTCTG

GGAGGGCGCCGCTCTTGCATAGCTGAGCGAGCCCG

GGTGCGCTGGTCTGTGTGGAAGGAGGAAGGCAGGG

AGAGGTAGAAGGGGTGGAGGAGTCAGGAGGAATAG

GCCGCAGCAGCCCTGGAAATGATCAGGAAGGCAGG

CAGTGGGTGCAGGGCTGCAGGAGGGCCGGGAGGGC

TAATCTTCAACTTGTCCATGCCAGCAGCCCCTTTT

TTTCCAGACCAAGGGCTGTGAACCCGCCTGGGGAT

GAGGCCTGGTCTTGTGGAACTGAACTTAGCTCGAC

TTTCGCTCGGCCTGGGACGGGGCCCAGGCCGGGCC

CAGCCTGGTGGAGCGTCCAGGTCTGGGTGCGAAGC

CAGGCCCCTGGGCGGAGGTGAGGGGTGGTCTGAGG

AGTGATGTGGAGTTAAGGCGCCATCCTCACCGGTG

ACTGGTGCGGCACCTAGCATGTTTGACAGGCGGGG

ACTGCGAGGCACGCTGCTCGGGTGTTGGGGACAAC

ATTGACCAACGCTTTATTTTCCAGGTGGCAGTGCT

CCTTTTGGACTTTTCTCTAGGTTTGGCGCTAAACT

CTTCTTGTGAGCTCACTCCACCCCTTCTTCCTCCC

TTTAACTTATCCATTCACTTAAAACATTACCTGGT

CATCTGGTAAGCCCGGGACAGTAAGCCGAGTGGCT

GTTGGAGTCGGTATTGTTGGTAATGGTGGAGGAAG

AGAGGCCTTCCCGCTGAGGCTGGGGTGGGGCGGAT

CGGTGTTGCTTGCCTGCAGAGAGGGTGGGGAGTGA

ATGTGCACCCTTGGGTGGGCCTGCAGCCATCCAGC

TGAAAGTTACAAAAATGCTTCATGGACCGTGGTTT

GTTACTATAGTGTTCCTCATGGCGAGCAGATGGAA

CCGGGAGACATGGAGTCCCTGGCCAGTGTGAGTCC

TAGCATTGCAGGAGGGGAGACCCTGGAGGAGAGAG

CCCGCCTCAATTGATGCCTGCAGATTGAATTTCCA

GAGGCTTAGGAGGAGGAAGTTCTCCAATGTTCTGT

TTCCAGGCCTTGCTCAGGAAGCCCTGTATTCAGGA

GGCTACCATTTAAAGTTTGCAGATGAGCTTATGGG

GGGCAATCTTAAAAAGTCCACAGCAGATGCATCCG

GCTCGAGGGGCCATCAGCTTTGAATAAATGCTTGT

TCCAGAGCCCATGAATGCCAGCAGGCACCCCTCCT

TTCCTGGGGTAAAGGTTTTCAGATGCTGCATCTTC

TAAATTGAGCCTCCGGTCATACTAGTTTTGTGCTT

GGAACCTTGCTTCAAGAAGATCCCTAAGCTGTAGA

ACATTTTAACGTTGATGCCACAACGCAGATTGATG

CCTTGTAGATGGAGCTTGCAGATGGAGCCCCGTGA

CCTCTCACCTACCCACCTGTTTGCCTGCCTTCTTG

TGCGTTTCTCGGAGAAGTTCTTAGCCTGATGAAAT

AACTTGGGGCGTTGAAGAGCTGTTTAATTTTAAAT

GCCTTAGACTGGGGATATATTAGAGGAAGCAGATT

GTCAAATTAAGGGTGTCATTGTGTTGTGCTAAACG

CTGGGAGGGTACAAGTTGGTCATTCCTAAATCTGT

GTGTGAGAAATGGCAGGTCTAGTTTGGGCATTGTG

ATTGCATTGCAGATTACTAGGAGAAGGGAATGGTG

GGTACACCGGTAGTGCTCTTTTGTTCTTGCTTCGT

TTTTTTAAACTTGAACTTTACTTCGTTAGATTTCA

TAATACTTTCTTGGCATTCTAGTAAGAGGACCCTG

AGGTGGGAGTTGTGGGGGACGGGGAGAAGGGGACA
```

-continued

GCTTGGCACCGGTCCCGTGGGCGTTGCAGTGTGGG

GGATGGGGTATGCAGCTTGGCACTGGTACTGGGA

GGGATGAGGGTGAAGAAGGGGAGAGGGTTGGTTAG

AGATACAGTGTGGGTGGTGGGGGTGGTAGGAAATG

CAGGTTGAAGGGAATTCTCTGGGGCTTTGGGGAAT

TTAGTGCGTGGGTGAGCCAAGAAAATACTAATTAA

TAATAGTAAGTTGTTAGTGTTGGTTAAGTTGTTGC

TTGGAAGTGAGAAGTTGCTTAGAAACTTTCCAAAG

TGCTTAGAACTTTAAGTGCAAACAGACAAACTAAC

AAACAAAATTGTTTTGCTTTGCTACAAGGTGGGG

AAGACTGAAGAAGTGTTAACTGAAAACAGGTGACA

CAGAGTCACCAGTTTTCCGAGAACCAAAGGGAGGG

GTGTGTGATGCCATCTCACAGGCAGGGGAAATGTC

TTTACCAGCTTCCTCCTGGTGGCCAAGACAGCCTG

TTTCAGAGGGTTGTTTTGTTTGGGGTGTGGGTGTT

ATCAAGTGAATTAGTCACTTGAAAGATGGGCGTCA

GACTTGCATACGCAGCAGATCAGCATCCTTCGCTG

CCCCTTAGCAACTTAGGTGGTTGATTTGAAACTGT

GAAGGTGTGATTTTTTCAGGAGCTGGAAGTCTTAG

AAAAGCCTTGTAAATGCCTATATTGTGGGCTTTTA

ACGTATTTAAGGGACCACTTAAGACGAGATTAGAT

GGGCTCTTCTGGATTTGTTCCTCATTTGTCACAGG

TGTCTTGTGATTGAAAATCATGAGCGAAGTGAAAT

TGCATTGAATTTCAAGGGAATTTAGTATGTAAATC

GTGCCTTAGAAACACATCTGTTGTCTTTTCTGTGT

TTGGTCGATATTAATAATGGCAAAATTTTTGCCTA

TCTAGTATCTTCAAATTGTAGTCTTTGTAACAACC

AAATAACCTTTTGTGGTCACTGTAAAATTAATATT

TGGTAGACAGAATCCATGTACCTTTGCTAAGGTTA

GAATGAATAATTTATTGTATTTTTAATTTGAATGT

TTGTGCTTTTTAAATGAGCCAAGACTAGAGGGGAA

ACTATCACCTAAAATCAGTTTGGAAAACAAGACCT

AAAAAGGGAAGGGGATGGGGATTGTGGGGAGAGAG

TGGGCGAGGTGCCTTTACTACATGTGTGATCTGAA

AACCCTGCTTGGTTCTGAGCTGCGCTCTATTGAATT

GGTAAAGTAATACCAATGCTTTTTATCATTTCCT

TCTTCCCTTTAAGTTTCACTTGAAATTTTAAAAAT

CATGGTTATTTTTATCGTTGGGATCTTTCTGTCTT

CTGGGTTCCATTTTTTAAATGTTTAAAAATATGTT

GACATGGTAGTTCAGTTCTTAACCAATGACTTGGG

-continued

GATGATGCAAACAATTACTGTCGTTGGGATTTAGA

GTGTATTAGTCACGCATGTATGGGGAAGTAGTCTC

GGGTATGCTGTTGTGAAATTGAAACTGTAAAGTA

GATGGTTGAAAGTACTGGTATGTTGCTCTGTATGG

TAAGAACTAATTCTGTTACGTCATGTACATAATTA

CTAATCACTTTTCTTCCCCTTTACAGCACAAATAA

AGTTTGAGTTCTAAACTCA

Long Isoform (22743bp)-*Homo sapiens* MEN beta, complete sequence, GenBank # GQ859162.1 (SEQ ID NO: 2):

<u>GGAGTTAGCGACAGGGAGGGATGCGCGCCTGGGTG</u>

<u>TAGTTGTGGGGAGGAAGTGGCTAGCTCAGGGCTT</u>

<u>CAGGGGACAGACAGGGAGAGATGACTGAGTTAGAT</u>

<u>GAGACGAGGGGGCGGGCTGGGGGTGCGAGAAGGAA</u>

<u>GCTTGGCAAGGAGACTAGGTCTAGGGGGACCACAG</u>

<u>TGGGGCAGGCTGCATGGAAAATATCCGCAGGGTCC</u>

<u>CCCAGGCAGAACAGCCACGCTCCAGGCCAGGCTGT</u>

<u>CCCTACTGCCTGGTGGAGGGGAACTTGACCTCTG</u>

<u>GGAGGGCGCCGCTCTTGCATAGCTGAGCGAGCCCG</u>

<u>GGTGCGCTGGTCTGTGTGGAAGGAGGAAGGCAGGG</u>

<u>AGAGGTAGAAGGGGTGGAGGAGTCAGGAGGAATAG</u>

<u>GCCGCAGCAGCCCTGGAAATGATCAGGAAGGCAGG</u>

<u>CAGTGGGTGCAGGGCTGCAGGAGGGCCGGGAGGGC</u>

<u>TAATCTTCAACTTGTCCATGCCAGCAGCCCCTTTT</u>

<u>TTTCCAGACCAAGGGCTGTGAACCCGCCTGGGGAT</u>

<u>GAGGCCTGGTCTTGTGGAACTGAACTTAGCTCGAC</u>

<u>GGGGCTGACCGCTCTGGCCCAGGGTGGTATGTAAT</u>

<u>TTTCGCTCGGCCTGGGACGGGGCCCAGGCCGGGCC</u>

<u>CAGCCTGGTGGAGCGTCCAGGTCTGGGTGCGAAGC</u>

<u>CAGGCCCCTGGGCGGAGGTGAGGGGTGGTCTGAGG</u>

<u>AGTGATGTGGAGTTAAGGCGCCATCCTCACCGGTG</u>

<u>ACTGGTGCGGCACCTAGCATGTTTGACAGGCGGGG</u>

<u>ACTGCGAGGCACGCTGCTCGGGTGTTGGGACAAC</u>

<u>ATTGACCAACGCTTTATTTTCCAGGTGGCAGTGCT</u>

<u>CCTTTTGGACTTTTCTCTAGGTTTGGCGCTAAACT</u>

<u>CTTCTTGTGAGCTCACTCCACCCCTTCTTCCTCCC</u>

<u>TTTAACTTATCCATTCACTTAAAACATTACCTGGT</u>

<u>CATCTGGTAAGCCCGGGACAGTAAGCCGAGTGGCT</u>

<u>GTTGGAGTCGGTATTGTTGGTAATGGTGGAGGAAG</u>

<u>AGAGGCCTTCCCGCTGAGGCTGGGGTGGGGCGGAT</u>

<u>CGGTGTTGCTTGCCTGCAGAGAGGGTGGGGAGTGA</u>

<u>ATGTGCACCCTTGGGTGGGCCTGCAGCCATCCAGC</u>

TGAAAGTTACAAAAATGCTTCATGGACCGTGGTTT

GTTACTATAGTGTTCCTCATGGCGAGCAGATGGAA

CCGGGAGACATGGAGTCCCTGGCCAGTGTGAGTCC

TAGCATTGCAGGAGGGGAGACCCTGGAGGAGAGAG

CCCGCCTCAATTGATGCCTGCAGATTGAATTTCCA

GAGGCTTAGGAGGAGGAAGTTCTCCAATGTTCTGT

TTCCAGGCCTTGCTCAGGAAGCCCTGTATTCAGGA

GGCTACCATTTAAAGTTTGCAGATGAGCTTATGGG

GGGCAATCTTAAAAAGTCCACAGCAGATGCATCCG

GCTCGAGGGGCCATCAGCTTTGAATAAATGCTTGT

TCCAGAGCCCATGAATGCCAGCAGGCACCCCTCCT

TTCCTGGGGTAAAGGTTTTCAGATGCTGCATCTTC

TAAATTGAGCCTCCGGTCATACTAGTTTTGTGCTT

GGAACCTTGCTTCAAGAAGATCCCTAAGCTGTAGA

ACATTTTAACGTTGATGCCACAACGCAGATTGATG

CCTTGTAGATGGAGCTTGCAGATGGAGCCCCGTGA

CCTCTCACCTACCCACCTGTTTGCCTGCCTTCTTG

TGCGTTTCTCGGAGAAGTTCTTAGCCTGATGAAAT

AACTTGGGGCGTTGAAGAGCTGTTTAATTTTAAAT

GCCTTAGACTGGGGATATATTAGAGGAAGCAGATT

GTCAAATTAAGGGTGTCATTGTGTTGTGCTAAACG

CTGGGAGGGTACAAGTTGGTCATTCCTAAATCTGT

GTGTGAGAAATGGCAGGTCTAGTTTGGGCATTGTG

ATTGCATTGCAGATTACTAGGAGAAGGGAATGGTG

GGTACACCGGTAGTGCTCTTTTGTTCTTGCTTCGT

TTTTTTAAACTTGAACTTTACTTCGTTAGATTTCA

TAATACTTTCTTGGCATTCTAGTAAGAGGACCCTG

AGGTGGGAGTTGTGGGGACGGGGAGAAGGGGACA

GCTTGGCACCGGTCCCGTGGGCGTTGCAGTGTGGG

GGATGGGGGTATGCAGCTTGGCACTGGTACTGGGA

GGGATGAGGGTGAAGAAGGGGAGAGGGTTGGTTAG

AGATACAGTGTGGGTGGTGGGGGTGGTAGGAAATG

CAGGTTGAAGGGAATTCTCTGGGCTTTGGGGAAT

TTAGTGCGTGGGTGAGCCAAGAAAATACTAATTAA

TAATAGTAAGTTGTTAGTGTTGGTTAAGTTGTTGC

TTGGAAGTGAGAAGTTGCTTAGAAACTTTCCAAAG

TGCTTAGAACTTTAAGTGCAAACAGACAAACTAAC

AAACAAAAATTGTTTTGCTTTGCTACAAGGTGGGG

AAGACTGAAGAAGTGTTAACTGAAAACAGGTGACA

CAGAGTCACCAGTTTTCCGAGAACCAAAGGGAGGG

GTGTGTGATGCCATCTCACAGGCAGGGGAAATGTC

TTTACCAGCTTCCTCCTGGTGGCCAAGACAGCCTG

TTTCAGAGGGTTGTTTTGTTTGGGGTGTGGGTGTT

ATCAAGTGAATTAGTCACTTGAAAGATGGGCGTCA

GACTTGCATACGCAGCAGATCAGCATCCTTCGCTG

CCCCTTAGCAACTTAGGTGGTTGATTTGAAACTGT

GAAGGTGTGATTTTTTCAGGAGCTGGAAGTCTTAG

AAAAGCCTTGTAAATGCCTATATTGTGGGCTTTTA

ACGTATTTAAGGGACCACTTAAGACGAGATTAGAT

GGGCTCTTCTGGATTTGTTCCTCATTTGTCACAGG

TGTCTTGTGATTGAAAATCATGAGCGAAGTGAAAT

TGCATTGAATTTCAAGGGAATTTAGTATGTAAATC

GTGCCTTAGAAACACATCTGTTGTCTTTTCTGTGT

TTGGTCGATATTAATAATGGCAAAATTTTTGCCTA

TCTAGTATCTTCAAATTGTAGTCTTTGTAACAACC

AAATAACCTTTTGTGGTCACTGTAAAATTAATATT

TGGTAGACAGAATCCATGTACCTTTGCTAAGGTTA

GAATGAATAATTTATTGTATTTTTAATTTGAATGT

TTGTGCTTTTTAAATGAGCCAAGACTAGAGGGGAA

ACTATCACCTAAAATCAGTTTGGAAAACAAGACCT

AAAAAGGGAAGGGGATGGGGATTGTGGGGAGAGAG

TGGGCGAGGTGCCTTTACTACATGTGTGATCTGAA

AACCCTGCTTGGTTCTGAGCTGCGTCTATTGAATT

GGTAAAGTAATACCAATGGCTTTTTATCATTTCCT

TCTTCCCTTTAAGTTTCACTTGAAATTTTAAAAAT

CATGGTTATTTTTATCGTTGGGATCTTTCTGTCTT

CTGGGTTCCATTTTTTAAATGTTTAAAAATATGTT

GACATGGTAGTTCAGTTCTTAACCAATGACTTGGG

GATGATGCAAACAATTACTGTCGTTGGGATTTAGA

GTGTATTAGTCACGCATGTATGGGAAGTAGTCTC

GGGTATGCTGTTGTGAAATTGAAACTGTAAAGTA

GATGGTTGAAAGTACTGGTATGTTGCTCTGTATGG

TAAGAACTAATTCTGTTACGTCATGTACATAATTA

CTAATCACTTTTCTTCCCCTTTACAGCACAAATAA

AGTTTGAGTTCTAAACTCATTAGAATTGTTGTATT

GCTATGTTACATTTCTCGACCCCTATCACATTGCC

TTCATAACGACTTTGGATGTATCTTCATATTGTAG

ATTTAGGTCTAGATTTGCTAGCTCCAAGTAATTAA

GGCCATGTAGGAGAGCATGGTAACCACAGATAGAA

CTGGTATTATCCCAAGTGGTCTGCAGACTGCTGAG

TGGGGATGGGATCTGCTCTCTGTTGAGAGTTGGTA

ATCATTGGTTTGAAATGTGATGAAACCACTCAAGC

CAATGAAGGTGGGTGTGTAGGTGGGGAGTACTTTG

CCATAATATTTTAAAACATTACCTGGTTAGAGTTC

TAAGTGGTACTTATTTTTGTTTGGTTAGGGGAAAG

CCTGAATAAAAACAGAAATGGACACATAATATGCA

TATTCCATAGTCTTTGGGAGGCTGGAATGTGCCTG

GGATTTGGGTCTAAGTGTATGCGTAATTCTTACCT

CACTAAAGAATTTGCCTTGTTTTTTTCCTTTTGGT

GAGTGACTAAAACGTCTGGGCTTCCCTGTGTGCGT

GCTACAGTAAGCAAGCAGAGGCTGTGCAAAGGTGT

GAGCAGGATCACGTGGAATCTGGAGGATACATCTT

GGCTTGCAAACTGCCTCTGTCTCCTGGGTGGGACT

GTTCTGTCCTTGCACTGCTGTTCTGTGTTACCTCT

TGGGGTGTAAGGTTTTGCTTACAGGAGACAAACTT

TGGGCGTAGAATGGAAGCCACTGCCAGCCTCTGTG

CTGAGAAGGAAGGTGCTTGTTTCAAAGGGAGCAGC

AAGGGAGGCTTGTTCTACTCACCTGGGCCTGTTTG

CCTGAGAAGGGGAGATAAGGGCTGAACTGGGACTA

GCCAGGGGACCAACACAAATGGTGGGGATCATG

ACCTGAAGGATTCTTTCCTTCCCATGAGCTGCAGG

GCTGGTTGCCGTCCTTGCAACTGTGTCTTATTTGC

CTGTGCCGTTATATCTTGGTGACCCCTCCACGTGT

ACACTACTGACAAACGGGTGGAGTGCTGGGAGAA

GTCACTGTGCCGCCCACCTAGTAAACCTTCTGTCT

GTGCTCATGGCATCTCCAAGATGGGGCACTGCTGT

GTGCAGAATCCAGGGTCCTCTTTCTGCTTGCAACT

CCTTTCCCTGGATGCCCCAGAAACAATCCAGGCCT

CCTTTCCTATCTTACCCCTTTGCTTTGCTTTTTAC

CCCAGCACCTCTATAACCGCCTTCTCTTCTTTTCA

GAACTCCTTGTTTCTCGTCCTGTTTTTTATGATTA

CAAAACTCTTGCTTCCACCCTGGAAGATAACTGCT

ATAGATGCCTGTATGTAAATGGTGCTGTCTCCAGC

AACTGGCATGCTGAAGAAGAATTGATTCACGGGGT

ATAAATGTTGGGGATTGGAAGTGGGGATGAAATGG

CACTTGTTGATACAGGAGCAGAGAGGTGAGGCCGA

CTGCTGAAGACAGCTCGCCACCCTCCTTGCCTCCA

CTCCAATCCAGGGGCTGGGGCACATTCTTTGCCT

TCATTTATCCTCAGATCAGGTGAGATCGACAGGAG

GTGTTGATGGCAGTGCCAGCAATTATTGCTAATCC

GTTTGCATCCTTATGCATAGATCTGAATTCAGACT

TTGTGAATTTCCAGAGGTGTGGGTAATATAATAGA

ATTCAGTGAGTGGGCATGGCTGATCTTGTGCAAAT

TAAAAGTTATGGGGCATAAGAATAGCAAAAGTTGA

ACTTCTTTTAAAAAGGAAAGTACCCTGAGAGCCAG

TATTGGTTGAGGCTCTTCAGTATGCCCAGGTTGGC

AGCACTGAGAACCGCAGGAACGGCCTGTTGTTACA

AAAAGGAGATTGACTCAGCTGCCCTTGGTGCATCT

GACTGACTATGACTGCTGAGAGATTCCAAGGACCC

TTAATGCCAGGGCTAACCTCTCCATGTGCAGTGAG

ACCTCTGGAGGAAGTGTCATCCTCTGGCTTTGTGT

GGTACTCATTATGGTGCAGTGCGGGCATGAAATGA

AGACACCCAAATAGGCTTACAGATACGATATGTTT

TAAATGTTCGTATTTAACAAAAACATACTGACACT

GTTTGGAAATGGCAACAGGAAGATAGCAAAATGAA

TACTAACATTACGAAAAGATGAACAGGTACATGTT

CCAAGGCAGGTGGCTGTGAACTTCCTCTGAGTGAA

GGCATCCCCTCCAGCACCTTTCAGCCTGCTAGTTA

GGACGACCCGCCGCCACCCTCCAGGACCTCCAGCC

CTGCACTGCCTTTCCTCTCTTTTAAATAATTCTTC

ATTGAGTTCTAATATGTAAAAAAAAGTTTACTGTA

AAGTTTGCAAAAATAAAGGAATTTTTTTTAAAAAG

TCCTCAGTAATCTTACCAGTAACAATTGTTATGGG

CACATTTGCTTTTGGAAGATTTCTTTTGTATGCAT

GGGATAAGTACATTTTTAAACAAAAATGGGATTAT

GCCATAAATTCTATTTTGTGACTTTAATATATAGT

GAACACCTTTTTTAATGATGACAGGATGTTCCCTT

GCATGGCTGTATCAATTTAAACAATCTTGTTTCAA

TGGGCATACAGGGTATTTTCTAGTTTTTTTTTCCT

CTTAGAAAATAATACTTGCGATGACTTTCCTTGTA

GCTCAGACTTTTTCACGTCTGTTGTTATCTCTTTG

GGAATGCTGAATACATACATTTCGAGAAGGAAATG

ACTGTTAAACTCTTAAGACTTCAGGTTCATATTGC

TAAACTGCCCAGCAGGGAGGGATTTTTTCAATTAG

TGTTCTCACTGGTGAGGCAAACCTGATGCCTTCCC

CTCTTCCTCAGAACCGGCTTTATCACATTGAAAAC

CTTTGCTCCTCCGACGGATCGAGTCTGCTTTCCCT

CTGGATGTGAGCATTGCTTTGTCTGCTGGTGACTG

AACATCTCTACCTTGTGTCAATTGGCCATTTGTGG

TGTGTGTGTGTGCGTGTGTGTGTGTGTGTGTGTGT

GTATGATTTTCTAATTCCTAGTCATTTTTCTATTG

ATTGTTTTGCAAAAGCCATTTACATCTTAAGGATA

```
TTGATAATCTTTTGTTATATTTGATGCAAATATTT
TTTTCCAGTTTATAGGTTGCCTTTTAATTTTGTGT
TTCAGGTAGATAAAAGTTAAACGATTTTCTTAGGT
TAGTTTATCACTGTGGTTTCTGAACTTGTTATGTG
TAGATCTTTTCCACCCCAAGAGTACATAAATATTA
ATCCATACTTTCTTATGGAACTTGTATGGTTTCGT
TTTTTACATTTAAACCTTCTTCCCCGTGGTGTGTG
TTGTGGAATCTGTGTTTGTGTGAGGAGGGGCATGG
TGCTCTCAGAACCCACCTCCTGTGGCCAGAGAGCC
CTGTCCTGTGAGGGTGGTTGTCACAGTGGCAGGGT
TCAATTCAGAAGACCTTGAGGGCAGGCTGATGTTT
CCTGAATGGGCCCCTGGTTGTTGCTTGTCCCTGAC
TCTCCATTTCCCCATCTGAGTGGATTTGGACCTAA
TAGGGCACTGGAGCTGGTTCGAATCCTGACTGGAC
TACTTGGCAACTTTATGTCTGGGAGCAAGTTACTT
AACCTCCCCAAGCCTGTGTCTGTGAAATGCGGGTA
AATGAATGTAGATGTTTGGCAGCAGCTACTCCTTG
TTGAGCTCTCACAGTGAACTCTCCTGCCTCTGCCC
TCCTTCCCCGCCTCCCCTGGTGCCTAGCGTCAGGT
CTAGCCACTTCCTCCTGGGCCCCTCTCCCTTTTCT
GTGGCTGGCTGCCTGCCCGCCTGGCGCTGGACCTT
TCATGTAACGGGAATCAGCATGTATATTCTGGTCT
GGTCTGTTTCTACACTTAATTTTGTTTCCAGTAGT
ATTTCCCTGTACCGGCAGAGTTCACAAACACATTT
GAAGAGGCTTTTTCTCAGGATTCTTAACCTTCCCA
AAGGAAGTCCCATGGATGGGTTTCTAGAAGTCTAT
AAATGCTCTGAAATTGTATTTTCTGTGGAAAGCA
TAACTTTCATCTGCTTGTTCGTGCTCAAAAAGAT
CATGAATGAATGATTGCATGATTTTATGCCATTGT
GCTTATACTAAAGGATATGTAGCCCATCTCTTGAG
CTGTTAAACTGTTTTGACTACTTTAAATCGTGCAG
CTGTGAGCATCTCTGTAAATTTAGTGTACACATGT
ATCCCCTGGAGTGGCATTGCCTCGGCAGTGAGCAC
TTATGGTTTTATAACTCTCTTCACAGACTCAAATG
ACTCCAGAAAGCTACACTTCCTGTTGTGAGTATAT
GATATCCATTTCCCTACATAGCCACTAACATCAGG
TTTTTACAATTTTATTTATTTCTTGCTACTTTAAG
AAATTTTGTGGTGAAATACATATAATAGAAGTTG
ACTATCTGAATCATTTTTAAGTATACATTCAGTAG
TGTTAAGTATGTCGCCATTGTTGTACAACCAATCT
CCAGAACTTTTTCATCTTGCAAAACAAACTCTGTA
CCCATTAAATAACATTAAACATTCCATTCCCTCCA
GCCTCAGCAACCCCATTCTACTTTCTGTTTCTGTG
AGTTTGACTATTCCAAGCACTTCATATCAGTTAAA
TCATGAAGTATTTGTCTGTCTGTGACTGGCTTATT
TCTCTGAGCACAGTGTCCTCGAGATGCGTCTATGT
TGTAGCATATGTCAGAATTTCCTTCCTTTTTAAAA
GATCCAAATAATATTCTTATTTTATATCTTTTTTT
TATCCATTCATCCATTAGTGGACACTTGGGTTGCT
TTTGGCTATTGTAAATAATGGTGCTATGTACAAAT
ATCTATATTATTGTATTTACAAGTATAATGCTGTA
ATGTACACACATCTTTTTGAGATCCTACCTTCAGT
TCTTTTGAGTATATAGCCAGAAGTGGTATTACTAA
ATCTTACGATATTTCTATTTTTAATTTATTGAGGA
ACCACTGTAGTTTTTCATAGCAACTGCACCATTTT
ACGTTCTCACCAAGAGTGCACAAGGGTTCCGAGGT
TCCCACATCCTCCCCAACACTTGTTATTTTCTGCT
TTTTTTAGATTGCAGCCATCATAGTGGGTGTGAGG
TGACATTTCATTGTGGTTTTGATTTGCATTTCCCT
AATGAGGAGTGATGCTGAGCATCTTTTCATATGCT
TACTGGTCATTTGTATGTTGTCTTTGGAAAAATGT
CTATTCAAGTCCTTTGACTATTTTAAAAATTGGGT
TATTAGAGTTATCGTTGTTGTTGACTTGTAGGAGT
TTCTTTCTATATTCTGGATATTAATCCCCTATCAG
ATATATGATTTGCAAATATCTTCTCTTATTCCATA
AGGTTACTTTTTCACTTTGTTGATTGTGTTCTTTG
ATGTATAGAAGTTTTTAGTTTTGAAATAGTCTAAT
TTATCTGTTTTTACTTTTGTGGTCTGTGCTTTTGG
TGTCATATCCAAGAAATCCTTGCCAAATCCAACGT
TATAAGGTACTTTTAAGGTATTTTAGTTGTCTTAG
TCTATATTTCTGTACTCACCTTTCTTTATCCACTC
ATCAGTTGATGGGCATGTAGGTTGGTTCCATATCT
TTGCAATTCTGAATTGTGCTATGATCAGGTGTCTT
TTTAGTATAATGATTTACTCTCCTTTGGGTAGATA
CCCAGTAGTGGGATTGCTGGATCGAATGGTTTTTA
TAATTTTCTATTTTACCACAGTTTCTCTCTGCATT
TTTCCTCTTTGACCACTAACCATGTGAAATTCTCA
TATTGACCTTTATAATGATCATGAACTCTTAGTAT
CATTGGGAAGGCCACATTTGCCACTTATGATTGTA
AACCTTATCCTCCATTTTTCCTGTTATTGTTGGTG
CAAAAAGCACCTATTATACCAGGACTTTAAAAATC
```

```
AGTCTGATAAGTCTTTGATAAGTCTAATAATAATA
ACTGATAAGTCCATTGAATTTGCTTCTGATTACTT
TTTCTTTAGTAGCTAAACATGTATGTACTCCTATG
ATTACAATGAACACTCCTCTCCATTTAAATTAATT
ATTTACATTGATGAAATAGCAAAATGTTAATGACT
AAATACTGTCTTGGTTTTTTCGTTCCAGGTCAGTC
AATATTAACTTCTTATAATTTTCTTTTTTTTCTTT
ATGTGTGTGTGTGTGTATTTTTTTTTTTTAAT
TTCAATGGCTTTTGGGGTACAAATGGCTTTTGGTC
ATATAGATGAATTCTACAGTAGTGAAGTCTGAGAT
TTTACTGCACCGGTCACCTGAGTAGTGTACATTGT
ACCCAATATGTGGTTTTTTATACCTTGCCCCCCTC
TTACCCTCCCCACTTTGAGTCTCTAGTGTCCATTA
TGTCACTCTGTATACCTTTTTGTACCCATAAGTTA
GCTCTCACTTATAAGTGAGAACACACAGTATTTGG
TTTTCCATTCCTGAGTTGCTTCACTTAGAATAATA
TCCTCCAGCTCCATCCAAAATTGCTGCAAAAAAAA
AAAAAACCACAAACATTATTTTGTTCTTTTTTATT
GCTAAGTCATATTCCATGGTGTAGAGATACCACAT
TTTATTTATCCACTCACTGGTTGATGGGTTGGTTC
CACATCTTTGCAATTGTGACTTGTACTGCCATCAA
GTGTCTTTCTGGTATAATGACTTCTTTTCCTTTGG
GTAGATACCCAGGAGTGGGATTGCTAGATCAAATG
GTTCTTAACATTTTCTCTCTGGATCTATTTCTGGA
AATTTTAGGCTCCAGTTTTTGTTGTTGTTGTTAAT
AAAATGCAATGGAATGTAATGATCATCACTTTTCA
TTATGCTTTAAAATCTGGTAAATGGAGGCTAGAAC
ACTCCTGTAAGGCAAGAATATTCTCTCTGTTGGAA
CTCAAATACACAGAACTGGGTAAATCTCAATCTTA
ATCTTTGATTCAGGACACAACATGGCTCTCTTTTA
CTTGCTTTCTTTAATTGTTTTTAATAATGTGGTA
AGCATTTCTGAATCTCCTATCCAATACAAAAACTA
GGACAATACAGACAGTAACTCCTATGGTTACAATG
AACACTCCTCTCCACTTAAATTAATTATTTACACT
GATGAAATTGAAATAGCAAAATTTTAATGACTAAA
TACTGTCTTTGATTTTTGTTCCAGGTCTGTCAAT
ATTAACTTCTTATAATTTTCTTTTTTTTCTTTAT
GTGTGTGTGTGTGTGTATATATATATATTTAAT
TTCAATGGCTTTTGGGGTACAAATGGCTTTTGGTC
ATATATATGAGTTCTACAGTAGTGAAGTCTGAGAT
TTTACTACACCTTCCACTTATGTGGTCCCACACCA
```

```
CCCGCCTCCCCTGCCGCCTCCTGCCACCCCCTAGG
CCAAGGTAATAATCATCCTGAATCCTGGGTTTATC
TCTCACTTGCTTTCTTTTCATATAATTTTGCAAAA
GAATCTGATCTAAATGTGTTTTTCAGAGTATATAT
TTATATTTTAGCTGTTCTTAGAGAAAATTTATTAT
TTTGCATGTAATCTTATGGAACATTCTCATTTAAT
ACCATGGTAAGATTCAGCCCTTGCCCAGGGGATAG
TTCATTTAGTTTGTTTACTGGATAGAGCTCATCAT
GTGACTATACCTCAGTTAGTTTATCAGTTCTCCCA
TCCATGGTGACTAGGTTGCCTCTCAGCCTCTCAAC
AACACTGTTTCTCAGTGTCCTTGTAGAAGTGATAT
GTGGGTGTTTCTCCTTACACAGAGTTGAAAGGTG
ACGACAACAACGTTGGCACTACCAATCCCCCACCC
TCCAGAGGGGTAACCAGTGTTACCAGTTTGCTGTG
TTTCCTGCTACACCTCGCCTTATTCACTTCCATTT
GTATCTGAAAAACGTGTTGCATGGTTTCTTTTCTA
TAGAAGTGGTAAAATGCTATTGTGTCCTGTACATT
ATTGATTACTTTTTTTCATTTAACAGTAGGGAGAT
GCCTGGGAGTACACAGAGAACTGCCCTCATTGTTT
TCAACTTCTGCACTGTATGTCTGTGAGTTTAGCCA
TTCTGCTGTTAATGGAAATTTACAGTATTCTAATC
TTTTGATATTACAAACAGTTCTGTGCGATCATCGT
CATACACAACCCCTTGTGCACAATGCATGAGTGTT
TCTCAGGGTAGGTACCAAGAAGTGAAATTCCTGGG
TCATAGGGCGTGAGTCCGACATTTTTCTCCATTCT
GCCCTGTTGCCCTCCAGAGTGGGTGTCCAGCTTTG
CATACCTAAGTATGAGAGTATCTGTTGTTCATATC
CTCTACGACGCTCCATATATGAAACTTAAGTTTCT
GCTAGTTGCCATCTTTGATCTATCATGTATGCAGT
GACCTACTAAGACTGTAATTGGTACAGTAGATTCT
TGTCATCTGTGTGTGAATTTAGCATTCATGGGCTT
AATGCTGACAAGGCCCCCAGGGTCCAAGACATATA
ATCATGTATAATTTTGTCAAGGTATAATTTTTTAA
ATTGCTTTTGTCATGTGTCTGCTGGTGATGCCCAA
CCCAGTGCTCTGCACCCAGGTCACACTGTGGCTTT
GTCCTCTGCTTATGCCTGCATTGCAGCAACTGTCC
TGAAGAGACCAAAATTATGCAGATTTAGGTAAGTC
CATGGCTAATGTTATTATATTATGTGCTATTGTAA
TGGATGGGCTGTGGAGTGTATGAATTTATAAATC
ACTGGTCTTGTAATTAAAATTCAAACACTATAGAA
```

```
AAAGGCCATGTAGAAGATAAAAGTTCCTCTATAAT
CCCGGACCCCTAAGATAACTACTAATGACAACTTC
ATTTATATTCCTTCAGACATTTTCTGGCTGTGGAT
GTACTAAAATGTATCCTATTATTCTCTGCCCTAAA
ATGGAATCATACAAGGTGTACTGTTATTTTATGG
CTCTATAACATGTCATATTGTACGTGTTGGTATGG
TCATTTTAACCATTTTTCTAGTGATGGCTTTGAGG
TTATTTGCAGTTTCCTAGCCATCTCAAAGTGTGCT
GCGGGGATCTCTTTTGCATCCCTCTGGGTGCAGAG
CTGAGGCACCCAGAGGCAGTGTCCAGAGGAGGCAG
CATCTGTAGGTGTCTTCACCTGCTCTGGCTCTTGG
CACATCTGGTTGGTGACACTGTTTTGTGAGATGGG
TTGAAAGCACGTGCTGCCAAAATAGAATAATGTTG
GTCCTCTCCTCATGTGCCGTGGAACTGGGGTAAAA
CTGCGTAGTGGCTGCAGCTGCCTGTCCATACCGGA
ATCGAGTATAACACGGTGCCTGGCTTAGCACAAAA
CAGTAGTGGGTCCTGCAGGCCCCAGAGTCTAATTC
CTGGTATTCTTTCCCCTACACAGATTAAATAAACC
AAAAACAAACTATTCTAGGAAAGCGTCTGTGACAT
TTGTAAAAAGTGGTATTTAATGATCTTTTATTCAC
TTGTCTGTTTAGTTTGTTGAAATCTTAAGTGGCAT
CCTGGTCTGGGAAGGAGTGCTGTCTGCGCCTGCCC
TCCGCTGGGCACAGCGTGGCTGCTTCAGGGGCTAA
GCACACACTTTCTGTCTTCTAAAGGGCCGCCACAT
GCCAGGAGCTCAGGTGTGAGCCCGGCTCTGGCTCT
TACCTCATAGGGTCACTCATAGGGGCACAGGGAGC
AGAACATTGTACACAGCGAGGCACCACCCGGCTTG
GCATCTGCCTCGGTGGACTTACTACCTCTAGAAGG
AAATACCTGAGTTCCTCTGGCCTCAGCTCCTAGAG
TGACTGGTGTGCTGTCCCTGTTACTCTTCTGTCAA
GGTGACAACTGTGTGACCCATCATCTGTGTGTCAA
AGCAAGGCCCTGCCTGGGCCTCTGCTCCTGTGCTG
ACCCCAAAGGCAAATGCTTTGCTAGTTTCCTTCCA
GTTAATTTCACCTATGAATAGATGTGTGAAAACTG
TTCAAAGCCATACCTGCACATGTTTGAACTTCAAA
CCCTGTGGGTGATTCAGTGGCATCTTTCTCTAACC
CCCAGCCTCCCTTCCCACAGAGGCCACCGTCATGG
CCAGTTGCTGCAGTTTCTTTCCAGAGAACCTGTGT
ATGTGTAAAGCTGTACAGGCGTGGGTACACCACAC
AGCCTGTCTTGCACTGTGGACTGTTGAGTTACTAG
TACATCTAGGTAAGCACCGCATATCTGTATTCATG
TCTGCCTTGGTCTTTTCAACATCTGTGTGGTAGCC
GTGTTTGAATTACCCATTCCCTTTTTGGGGAACCA
TTAAGTTGTTTCAGCAATTTTTACTGTAGATAAGG
CTATACCGCATATCTGTGTACATGGGTTTTTATGT
ACATGGGCAAGTATATCTGTGAGAGAAAAGTTTCC
TCAGGAGGAATTCTGGGCACAGCATGTGTAAATTT
CTAAATATGATGGACACCCCCAGCTTCCACCTCAA
GGAGGTTGGTCCCATTGACATTTCCCCACACCTTC
ACCCAGGCTGTGCCCTTAAACTTGGTTATTTGTCA
ATGTGAGAAGTGGAAAATAGTATTTAATTGTAGTT
TGGATTTGTATTTCTATTGGGTTGTATACTTACTG
ATTAATAATAAGAGCTCTTTACATATTAAGGAAAT
TAACCCTTTTCAAATACATTCCTATTTCTCACTAA
TCTTTAAGTTTTATTGTAATATTTTGCTCTTTAGT
TTATATATATATGTATATATATATATATGTATATA
TATATATATACATATATATATACATATATATATAC
TAATTTTCTTTTATGGTTCCTGGATTTTGTGAGTA
GTTTGAAAAGGCTAATCCAGCTGAAGATTTTGTTG
TTGTTGTTAAACCCCATGTTTTCTCCTAACTCTTT
TTATTTTTATTTTGGAGGACTCTATCTAGACTTAA
TTTTAGCATAACAAGTGACAGGGTTAGTTAGCCTG
TTGTCCTTACACCATTTTCTGGCTAATACAGCTAT
TAACTATTGATCTGTCTATTCACGTGCCAGTTCCT
AATGGTTTTACATAGTGTAATCTGCACTTCAAAAT
AGCGAAGGGAAGCCCTACCTCATTATTCTACTTTT
CCAGAATTCTCCTGGCTATTCCAGGCTGCATGTTT
ACCTTAACCTTCCCTGTGATGTCTTCATGCCGTTG
TCTTCTTATGCAAGAATAAGGTACGTCTTTCCATC
CACTCACGTCTATTTAATTTGACTTTGCATTACAC
AGAAAGCTGGTCTTGGTCTGTCTACCTCGGCATCT
AGTTGTCCTCACTGCCCCCTAGCCGACCCCACCCC
ATCTGACTGACTACCCCATCACAGAGTACTTTTAT
TTACGTTTTGCTCTGCCTAATGGTTACTTGATACT
GTCACGCCGACAGTGTCCAGTTCAGTGGTCTTTGC
AGTTGAAATGCTCCCGTACACACTGTCTTGTTAAA
AATGCCAGTAAGTTCATACAAACCCAGCTTGCACC
CAAGGTCACATTCAGAGAGCGTAGGGCTGGGATGG
GTTGTTTTCCAAGCTTCTGCCACTGTGTGGCTAGC
TCTTCCCACTGGGAAGTTCTGTGTACCCGGAATGT
CGGAGTGGAGTCCTGTTCTAGTGTCCAGCACCTGA
```

-continued

CCCTGTGCCCAACCCCTCAACAGCCTATTCCTGCT

GTCCACAGCCTGCTGGAACTTTTTACAAAATATGT

TGCCATGCTGGACCCTGGGCACTGGACATAAGCCC

CCTGGCAGCCTTTTTCATGTCACCCAAAGGGGTAA

TTGTCCTACTGGTGGTCTGTAAGATGAGTTAGGGT

GACTTGCTAATAGACATTGTAAATCTTAATATTTA

TGTATGTATTTTATTATTACCGGTTTTCCATTTAT

GATGGTAATATTGTTTCTTCTAAGAATATTTATTT

TTCCTTCTAAATATTGAGATAAAATTCATGCTTTT

GAAATGTTCTATTCAGTGGCTTTTAGTATATTTGC

TATGTTGTGCAACCATCGACACTATCCATTTCTAG

AACTTTTTCGTCATCCCAAACAGACGCTCTGTATT

CATAAAAAAATAACTTCCTACCTGTCTCTCCCCCT

AGTCTTTGGTAACCTTTGTTATACTGGTAAACTTT

GTTGTGCTCTCTGTCTGTGTGAATTTGCCTATTCT

AGGGGCCTCATATAAGTGTAATCATACAGTATTTG

TCTTTTTGGGTCTGTCTGATTTCACTTAGCGGGTT

TTCAGGGTTCATTCATGTTGCAGCATATAACAGTA

CTGCGTTCCTTTTTCTGGCTGAATAATATTCCACT

GTATGGATAGACCCCATTTTGTTTATTCACACATC

ATTTGGACATTTGGATTATTTCTGGTTTTTGGCTA

TTATGAACAATGGTGCTATGAACAGTTGCGTACAA

GTTTTTGTGTGAACATATGTTTTCAATTCTCTCAT

TATATACCTAGGAGTAGAATTACTGGGTCATATGG

TAACTGTATATTTTTGAGGAACTGCCAAACTATTT

TCCCACGTCCATGCACCATTTCACATTCCCACCAG

TAAGTAAGAGGGTTCCAATTTCTGCGCATTCTTGC

CAACACTAGTTATTATCTGACTTTCTGGTTATAAT

CATTCTAATGAGTGTGAAGTAGCCTCTGGTGTCAT

TTGGATTTGCATTTCTCTGATGAGTGATGCTATCA

AGCACCTTTGCTGGTGCTGTTGGCCATATGTGTAT

GTTCCCTGGAGAAGTGTCTGTGCTGAGCCTTGGCC

CACTTTTTAATTAGGCGTTTGTCTTTTTATTACTG

AGTTGTAAGAGTTCTTTATATATTCTGGATTCTAG

ACCCTTATCAGATACATGGTTTGCAAATATTTTCT

CCCATTCTGTGGGTTGTGTTTTCACTTTATCGATA

ATGTCCTTAGACATATAATAAATTTGTATTTTAAA

AGTGACTTGATTTGGCTGTGCAAGGTGGCTCACGC

TTGTAATCCCAGCACTTTGGGAGACTGAGGTGGGT

GGATCATATGAGGAGGCTAGGAGTTCGAGGTCAGC

CTGGCCAGCATAGCGAAAACTTGTCTCTACTAAAA

-continued

ATACAAAAATTAGTCAGGCATGGTGGTGCACGTCT

GTAATACCAGCTTCTCAGGAGGCTGAGGCACGAGG

ATCACTTGAACCCAGGAGGAGGAGGTTGCAGTGAG

CTGAGATCATGCCAGGGCAACAGAATGAGACTTTG

TTTAAAAAAAAAAAAAAGTGACTTGATTTAAGGGA

AAAAATGACTGGCTATATTCAGTCAGATATGGCAA

AAAGTCTCAAGGTGTTAATGTGAATGATTAAGGTC

TTGGGGGGGGTGTCCCCTATCAGACTACAGGTGTT

TAGAGGCACAGAAAAGGTGCAGTTGGGTTCTTAA

TGTGAAATGATGAGAAGCACAACTCCAGTGTGTCT

CTTTGTGTAGAATGTCAGCAGACACCCCCTGCTAG

ATGTGCTGGATCATGGGAAAGCATTTCCATTTGTT

ACTAGATTGTTCAGAAGTTTTAATTTATGATGGGT

GTGGTGGCTCATGCCTGTAGTCCCAGCACTGTGGG

AGGCTGAGGCAGGAGGATCATCTGAGGCCAAGAGT

TCAAGATCAGCCTGGGCAACATAGTGATACCCTAT

CTCTTAAAAAGAAGAAGTTTTTAAATTTGAAATA

ATAATAGGTACTGGATTTATGCAAATGTCTTTTCT

GCGTCTTTTGAGATGAGTATCAGGTTTTTTTTTTT

CCTTTTATCATCTGATGATGAACTTAATGTTTCCA

TTTGTATTAATGGAATACTAAGTCCCTCTGTGATT

TCTGAACCAAGCTATTCCTAGGCCTGAGTTTTATT

TTGTTGACACAGAAATAAATTAGAAGGCCAAGCGT

GGTGGCATGTGCCTGTAGTCCTAGTTGCTGAGGTA

AGAGGATTGCTTGAGCCCAGGAGTTCAAGGCTGCA

GCAAGCTTTGATTGCGCCACTGCACTCCAGCCTTG

GCGACAGACTAAGACGCTGTCTCAAAAAAAAACAA

AAACGACAAAAAAAAAACAAAACAGAAAAAATAAA

CTAAGGCAATGACAGTCCCTGGCAAATGCTGGGAG

GGAGGCAGCAGTGGTCAGGGAAGGTAACCCTGAAG

CAGGACTTGTAAAGCAAATAAGATTGGGAGGCCAA

GGTGGGTGGATCACGAGGTCAGGAGTTCGAGACCA

GCCTGGCCAACATAGTGAAACCCCGTCTTTACTAA

AAATACAAAAAATTAGCCAGGTGTGGTGGTGGGT

GCCTGTAGTCCCAGCTACTTGGGAGGCTGAGGCAG

GAGAATCTCGAACCCAGGAGGCGGAGGTTACAGTC

AGCTGAGACCGCACCATTGCACTCCAGCCTGGGTG

ACAGAGCAAGATTCCGTCTCAAAAAAAAAAAAAAA

AAAAAAACCAAGAAGAAAAGGAATGAATTAGAACT

TCTTCTGCTTGGACTTAAGGGCATCATCAGGCAGG

TTTTGGGTAGGATAGCAGGGGAGGCAGAGACATAG
TCGGGGTCAGTGGTCATGAGTGTGGCTTTGAGCCC
AAAAACTTGGTTTCTGTTCCCTACTTTGCCACTCA
GTAGTGCATGACTTTGGCCAAATTTCTTAAATTCA
TGAAGCAAGTTTCCGGGTGAATGAAATGGGGATAA
AAATAGTGTTCAAACCTATCCGTTGGTTTGTGTGA
AACTGAAATGAATAGTATCGTGCAGGTACTTGTGA
GCAAGGGGAGCTGCTGTTTCCTGTCCCTTTATGAT
GGGAAATATCTAGACAAGTTCCCAACCCTCTGCAC
TGCAGGCTGCATGGCACGGAGGGTCTTGTAACACC
AGCTGGGGCTGGCCTTCTTTTAGGAGCTTCAGTGG
TTCTGAAAACTTTTATTTGTTTGTTTGTTTTAGTA
GATGTGGGGTCTTTCTGTGTTGCCCGGACTGGTCT
CAAACTTCTGGACTCAAGTGATCCTCCCCCGCTCA
ACCTCCCAAAGTGTTGGGATTACAGGTGTGAGCCA
CTGTGCCCAGCCTTGAAAACTTTTTCAGGTTCTTC
CAGGGTTACTGGGCTATTAAATATTTCTATTTCAT
TATAAGTCAGTTTTTCAAAGTTATATTATCTTAAT
TACCTTTTTATATGTATTAGTGTAGAGTAGCATT
TTATATTTGATATCCTCCTTATGCATAGTTTTTC
ACTTTTTATTCCTAGTTTTTCGTTTTTAATAAGAC
TTTCAAGAAATTTATTTTATTGGCCTTTTGAAAAA
AGCAGCTTTAGATAAAGTAAGCAGTTCTGCTTTCA
TTTTATAATTTATTTCTACTTTTGTTTCATTAATC
TTTTCCTCCGGCATGCCTTGGATTTTGTTGTGTTA
CTCTTTTTCTAGAGGCTCGCATTGTGTGTCTGGTT
CACTTATGATCACGCTTGCCTACTTTTAAGAATGG
AAGAGGGGAGGTGGAGGGTGGCTGCACAGTCGAGG
GTGTGAGGCAGTCTTGCTCTAGCCCCACCATGCCC
TCAGCCCGCTGTGGCCACGCTGGTTCCTCAATTGC
TGGGGCGTGCAGTGTCTGTAAGGGAGGCTACTGAT
GCCATCCGAGGAAGATGTAAGGTTTCGTGTGGGCA
GCGAGAGCCTAGCAGGCATGTGGGGTGCCCAGCAA
AGGGTAACAGTGGACAGTTGTTGCCTCATTCCACA
GAGTTTTGATTTTTTTTTTTTTTAATGGTCACT
CCATCAACATCCCCCATGGCCAGAGCCTGAGCTGG
TCCCCAGAGACACAGGCATTCAGCTGACAGCCTCG
CCTTCACGCTGCTGCTGTTCTCATGGGGACAGGC
CTCAGGTGGCAATGCACAAATCATTAGTTAAGGGC
AGTTGTGACAGTTACCAAGGAGTGTAGTCCCCCGC
CCCCCGCCCAGTGAAAACAGCCCTAACCAGGGGTG
GGGACCTTTGGGCTCTGACCCGAAGGGTAGGAGAA
GCTGGAAGGACAGCATTCCTGTCTGCGAAGGCAGG
AGCAAAGCTGCCAGGCTATGAAGGAAATGGCTGGA
GCCTGAAGTCATGCAAGCTGGGGCTGGCAGGGACA
GGGCCAACTTCCAGGCCTGGGGGCCACCATGAGGA
TTCAGGACGTGACCCCCAGGGCACATGAAGGCCTT
CCATCTGTATTTAAGAAAAGACTTTATCAGACGAG
TATGGTGGCTCACGCCTGAATCTTAGCACTTTGGG
AGGCTGAGGCAGGTGGATCACGAGGTCAGGAGTTC
AATACCAGCCTGGCCAATATGGTAAAACCCCATCT
CTACTAAAACTACAAAAATTAGCCAGGCATGGTGG
CGCACGCCTGTAGTCCCAGCTACTCGGGAGGCTGA
GGCAGAAGAATCACTTGAACCCGGGAGGTGGAGGT
TACAGTGAGCCAAGATCGCGCCACTACACTCCAGC
CTGGGTGACAGAGTGAGACTCCGTCTCAAAAAAAC
CAAAAGACTTTATCTTATTTCCTATATGTTTGTGG
TTTCAGTCCTGATGTATAATTTGACCCTAGTTAGA
ATGGTTATCTGAGGAAGTGGCCTGTACGATTTCTG
CTTTTTTAAATGTGTGGCTCCCTTTCTTCATTGAT
TAACGTATGATTATTTTTATAAATGTTCCATGGCA
GTGGGAAGGGATTCTCTGTCACATTCCACATCTGG
ATCAGTTCCTCCCCATTTTGTTGGTCAAATCCGAT
CTGCCATATCCTGTGTAATGACAAGTGAGTTGCAT
TCTCACCGTCACTCCTGGGGTCTCTCCGCTTCCCC
TGAGCTGGCTCAGCAGTCTGCTCCATGTGTTTTGA
TGCAGGGTGACCCATTGGTATTCCCGACACTAACG
CCCCCGTCTGTGGACTGCTTGCTGCTTGGGCTTCA
CTGTGTCTGGTGTTGACAGTGCAGACCTAAAGGTG
TGCACACATGTGCACACACACTCCGCTGTCTTCTT
GTTTGCACTGGACTTAAATATCTATGAGGGTTATT
TTCAACTGCTGAATTTGGAATGATTTTTATATCTT
TTCTGCTTTCTGCCCATGTACATGTGTTTATTTTA
CACTGTTGTGATTGGTAGTTACTATGTGGGACAC
AATTACTTGGGCTGAAATAATCCACCTGTTGTGGT
TGGGGTCCTCTGGGGCATTCCAGGGTGAGAGGTTG
TCACTGCCACCTGGGCCATGTGGGCCGGCACCAGC
ATTTTGTGGTTACGAATTCTACAGTCACAAATATC
TTTGGGCAAATCCCCTTCTATACCTCAAGGCAGCT
TTTGGTTTGCAACCCCACTGGCCAGAGGGAAGGGC
CAGTCACTTGGCTCTCTCACTGCCCTGCGCCCCAG

```
ATGGTTCTAGGGCTGCTGTTTTCCCTTGGCCCTGC
CAACACCACTGTTTTTACTTCTGCTCATTGGCTGA
GTGCAGTGGTTCCTGGAAGCCAGTGGCACGTTTCC
CCGCGTAGCTCGCTTATCCCACAGCACACACCCAA
GGGTTCTGTTGCTAACACGCTGAATTAATTCTTTG
CTCATCTTACAGAGTGTGTTTTGACTGCCCCCATT
TCTGAGGCCTTGTAAGGCCAGAGCTTTGTTGCTTC
ATCGGCAGGTTGGGACTTAGATGGCCGTGAATGTT
TCCTCTCTGCTGCTGCAGTAAGTAAGTGCCCGCAC
CATAGTGTGTTTGGAGGCTGAAGTTGAAGCGAGGC
TGTGAGGGGAGATGGACGTGTGAGGAGGGATGATG
GGGCTTGAGCAAAGTGGGGGAGGGGGCAAAGGCAG
TTGGCCCAACACATTCCCCACCCCTTTGAGAGGTC
TGAGGCCTGCAGACCTGGCTCGGAGCCCACCTGGT
AGTCCTCAGACTGTGTGTGTGTGTGTGTGTGTGTG
TGTGTGTGTGTGTGTGTGTGTGTGTGTGTGTGTGT
AAAAGAGAGAAGTTGTGGAGAAATGGGGGCTGAT
TCTGCTCAGATTCATCAGGATGAGTAGAAGGCACC
CAGCTCTCACCCTGGCCTGACATGTGTGTCCCTGA
GCAGGTTACAGTCCTCTCTGAGCCTCTGCTTCCCA
TCTGGACCCTGCTGGGCAGGGCTTCTGAGCTCCTT
AGCACTAGCAGGAGGGGCTCCAGGGGCCCTCCCTC
CATGGCAGCCAGGACAGGACTCTCAAATGAGGACA
GCAGAGCTCGTGGGGGGCTCCCACGGACCCGCCGT
GGGCCCAGGGGAGGCAGAGCCTGAGCCAACAGCAG
TGGTGCTGTGGACCGTGGATCCTGAGGGTGGCCTG
GGGCAAGTACCGGCTGAGGGTCCAGGTGGGCTTTG
TGTACCTTTGGGTCCTGGGGCCCTGGTGACTTGGA
CTCCAGGTTAGAGTCAAGTGACAGGAGAAAGGCTG
GTGGGGCCCTGTGCTTCCGACTTCATTTCGAGTGA
TGGCAGTTCCCAGGAAGGAATCCACAGCTGACGGT
GGCTGACAGATCAGAGAATGGAAGGCGAGGCAGGC
GGGCGTCTGCGTGACCTCAGGTGCTTGGGGCCCAG
CAGACCCAGAGAACCATTTCCACTAGGCCAGGGTG
CCGGAAGTGTCCACAGGTCTTAGATTCCCTGTTCA
GATGAAAAGATTTGTGCCTTTAATGATAAAAGTGA
TCTGCATAGAGTCAAAAATTCAAGCCATGGGTATA
AAATGCAAGTAAAATCCCTGCCCTCACCTATCCCA
CCCTACTACACAGAGATGTCCTCTCGAGTTTCCTA
GACTCACTCTGGAAATTTCTGTATACACACAGAAG
CTTGTGCCTCTGCTCGTGAAGGCAGAGGGAGGGAG
AGCTGAAGGGCCAGCACCTTCTCACCTGTGGGCCC
CCTCAGTGCTCGGTCCCAGAGCATGCAGGACTGTG
CCTCGTGTTCAGTTTGCTGGTCTGACTTCATGCTC
CTTGGGCAGGATATGCATGTGCCATGCTAGGAGAC
ATGTGGATGTGAAGCTGGGGGACAATGTCCCCTGG
CTATGCCTTTACAAGGGAAGTAAGGAAGGTAGGAG
GTGAGCCTGGGAGGGAGGGAGGGAGGCGCGGAGCC
GCCGCAGGTGTTTCTTTTACTGAGTGCAGCCCATG
GCCGCACTCAGGTTTTGCTTTTCACCTTCCCATCT
GTGAAAGAGTGAGCAGGAAAAAGCAAAA
```

Methods of Diagnosis and Prognosis of Prostate Cancer

This invention provides diagnostic methods for determining the stage of prostate cancer, for example, the presence of an advanced stage prostate cancer. The invention also provides prognostic methods for determining a risk for developing prostate cancer, and a risk for an existing prostate cancer to progress towards an advanced stage prostate cancer. These diagnostic and prognostic methods are based on detecting the level of NEAT1, i.e., the level of the NEAT1 RNA molecule, in a biological sample in a subject.

The term "risk", as used herein, means likelihood, i.e., more likely than not.

Prostate cancer can be evaluated based on well established procedures and techniques, including physical examination (e.g., tissue biopsy, digital rectal exam); imaging studies such as CT scan (which reveals blood flow and anatomy of tissues in and around the prostate), MRI, PET/CT scan (an advanced nuclear imaging technique which combines positron emission tomography (PET) and computed tomography (CT) into one machine), ProstaScint scan (which may be used to detect if prostate cancer has spread to the lymph nodes, adjacent tissue or bone), ultrasound imaging; blood or genetic tests (testing established biomarkers of prostate cancer such as prostate-specific antigen or "PSA" and prostate cancer antigen 3 gene or "PCA3").

Prostate cancer can be staged based on the above evaluations. A commonly used staging scheme is the "TNM" system, which evaluates the size of the tumor ((T1/T2/T3/T4), the extent of involved lymph nodes (Nx/N0/N1), any metastasis (M0/M1/M1a/M1b/M1c), and also taking into account cancer grade (determined by the Gleason Grading system). According to the TNM system, prostate cancer is classified as Stages I-IV. Briefly, Stage I disease is cancer that is found incidentally in a small part of the sample, and the cells closely resemble normal cells and the gland feels normal to the examining finger. In Stage II, more of the prostate is involved and a lump can be felt within the gland. In Stage III, the tumor has spread through the prostate capsule and the lump can be felt on the surface of the gland. In Stage IV, the tumor has invaded nearby structures, or has spread to lymph nodes or other organs.

In one aspect, this disclosure provides a method of determining a risk of developing prostate cancer in a subject who does not yet have prostate cancer, by detecting the level of NEAT1 in a biological sample from the subject, comparing the level of NEAT1 relative to control, and determining the risk of developing prostate cancer in the subject based on an elevated level of NEAT1 in the sample as compared to the control. According to this aspect of the invention, the control level of NEAT1 can be a pre-established value or a range of values, for example, from healthy individuals (such as healthy individuals who do not develop prostate cancers in follow up studies).

In another aspect, this disclosure provides a prognostic method for determining a risk of advancing the prostate cancer in a subject, for example, a subject who is diagnosed to have prostate cancer based on other clinical or pathological evaluations. According to this aspect, an elevated NEAT1 level in a biological sample of the subject relative to a control level provides a basis for determining a risk of advancing the prostate cancer, i.e., the cancer progressing towards an advanced stage.

The present inventors have shown that patients with higher NEAT1 expression have significantly worse outcomes, as reflected by at least high Gleason score, biochemical recurrence, and metastasis events. Thus, the NEAT1 expression level provides a prognosis basis independent of common clinical and pathological variables. More specifically, based on the comparison of the NEAT1 level in a prostate cancer patient to a control level, one can determine a risk of the cancer progressing towards an advanced stage.

By "advanced stage" prostate cancer, it is meant herein to include prostate cancer of at least Stage III or IV, prostate cancer that has significant involvement of lymph nodes, prostate cancer that has metastasized, prostate cancer that recur after surgical removal or other therapy, and/or prostate cancer that is resistant to hormone therapy or other therapy targeting post castration (such as NEPC and CRPC).

By "cancer progressing towards an advanced stage" it is meant that the cancer advances or worsens based on one or more clinical or pathological evaluations such as those described hereinabove. Progression of cancer can be, but does not require to be, a change from one stage to a more advanced stage as defined by the TNM system—it can be, for example, a change from a less advanced sub-stage to a more advanced sub-stage within the same TNM stage; and it can also be from any of Stages I-IV to a more advanced, aggressive prostate cancer (e.g., NEPC, or cancer resistant to hormone therapy or therapy targeting post castration).

Figures 8A, 8B:
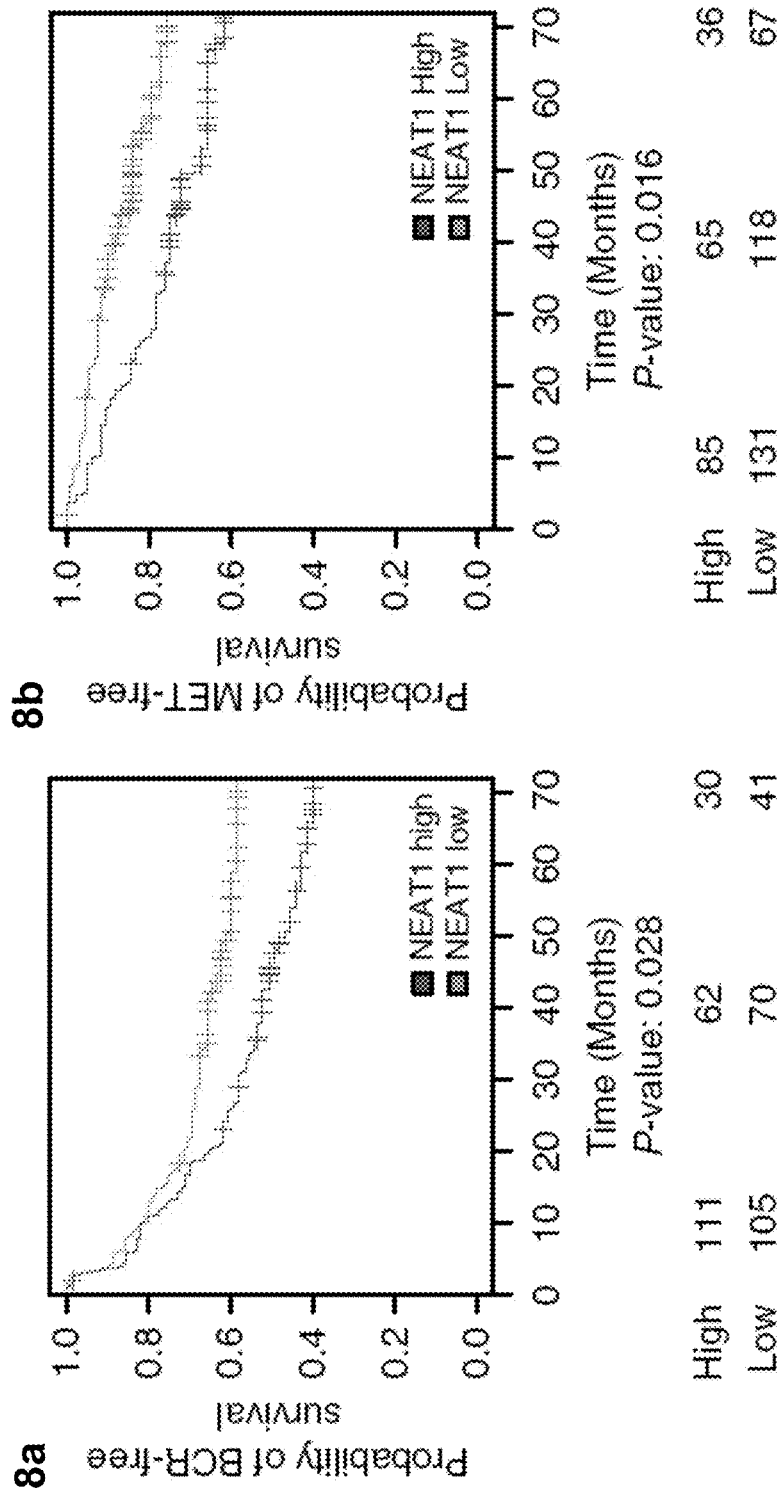
FIG. 8a-8j. NEAT1 overexpression is associated with aggressive prostate cancer. (8a-8b) Kaplan Meier curves showing (8a) Biochemical recurrence (BCR) free survival and (8b) metastatic recurrence (MET) free survival for NEAT1 low and high expression groups of samples from the Mayo case-cohort dataset (Erho (2013)) (n=216). The cut points to define high and low NEAT1 expression were selected using patients from the Mayo nested case-control dataset (n=378) (Blute (2001)) by maximizing the product of the sensitivity and specificity for each endpoint. The number of patients at risk for each group is shown beneath the plot. AUCs and 95% confidence intervals for the expression of NEAT1_1 transcript predicting BCR (8c), MET (8d) GS>7 patient outcomes (8e) and PCSM (8f), and NEAT1_2 transcript predicting BCR (8g), MET (8h), GS>7 patient outcomes (8i) and PCSM (8j). p-values calculated using the Wilcoxon signed-ranked test indicate that both the long and short forms of NEAT1 are found to be significant prognosticators for each outcome.
Figures 8C, 8D, 8E, 8F:
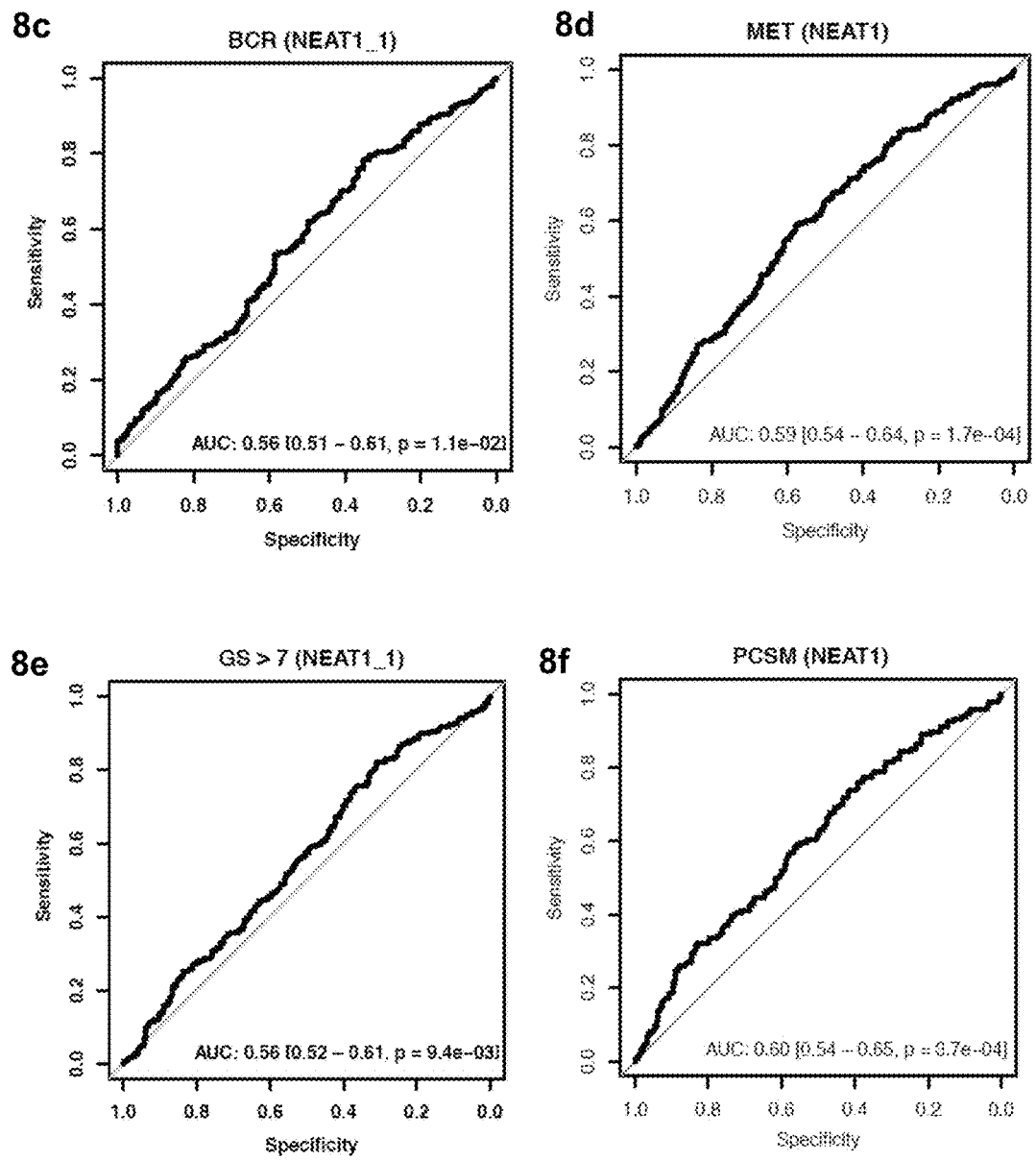
Figures 8G, 8H, 8I, 8J:
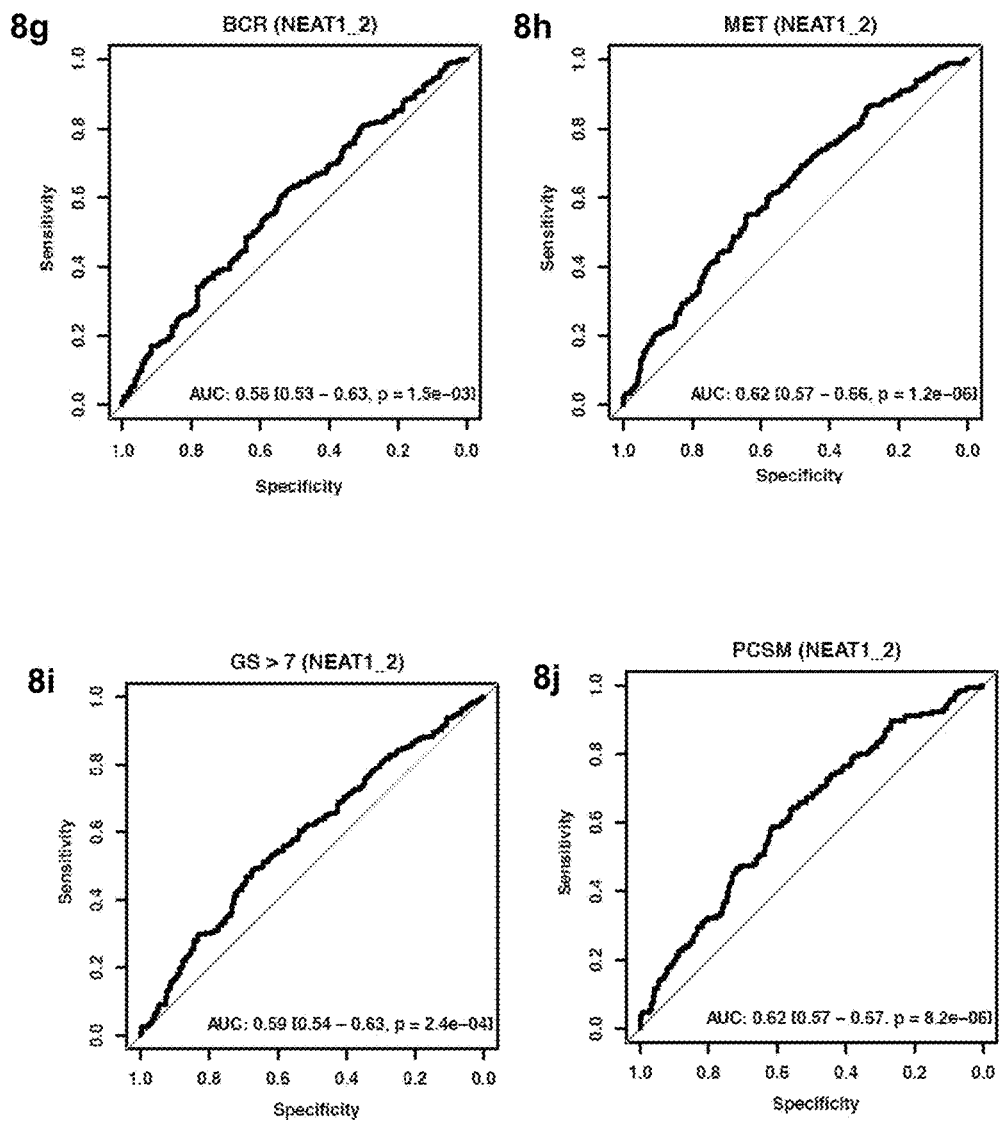
Figures 9A, 9B, 9C, 9D:
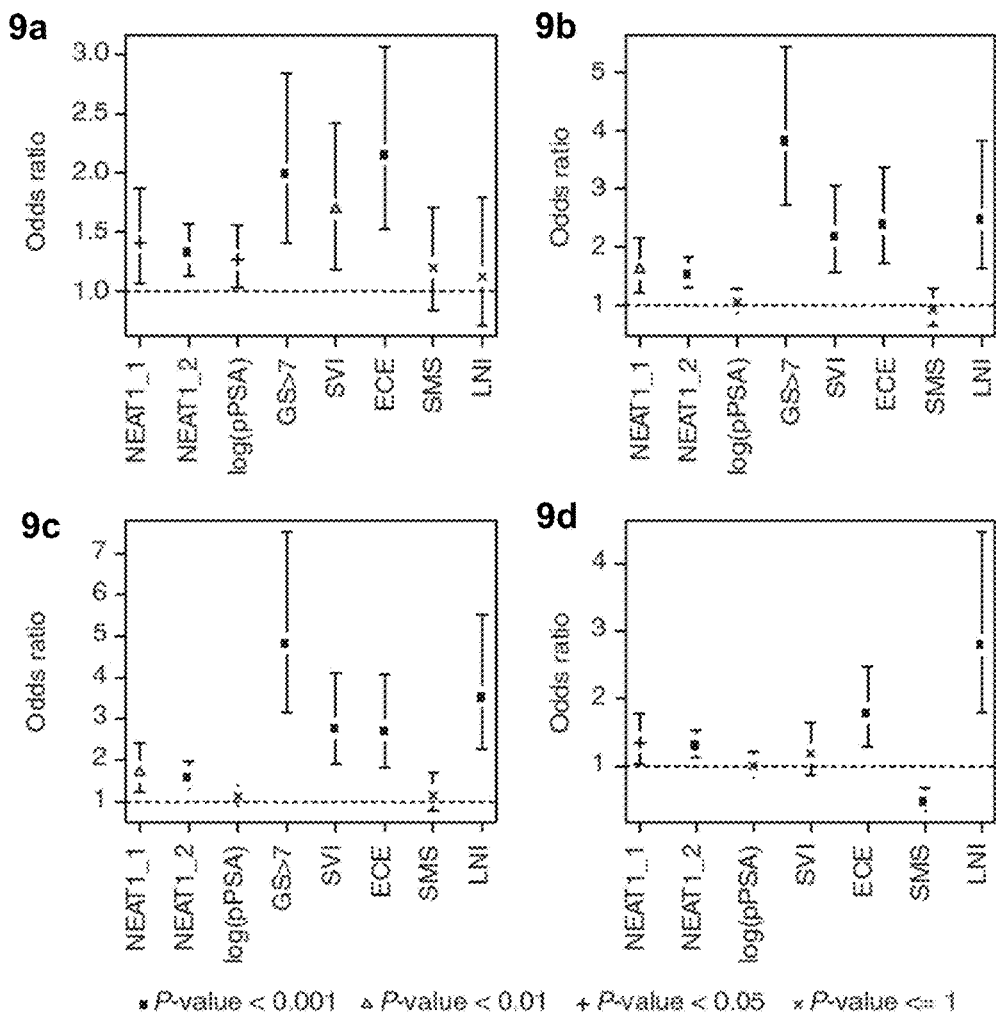
FIG. 9a-9l. NEAT1 is a strong prognosticator of prostate cancer. (9a-9d) Univariable forest plots comparing the expression of NEAT1's short (NEAT1_1) and long isoform (NEAT1_2) to clinicopathologic variables in the pooled Mayo cohort (n=594) (9a) BCR, (9b) MET, (9c) prostate cancer specific mortality (PCSM), (9d) Gleason score (GS) >7. Pathological tumor stage 3 or greater (pT3+), Lymph Node Invasion (LNI), Surgical Margin Status (SMS) positive, Seminal Vesicle Invasion (SVI), Extra Capsular Extension (ECE), preoperative PSA (pPSA), adjuvant hormone therapy, and adjuvant radiation therapy are shown. (9e-9m) Multivariable odds ratio forest plots for expression of NEAT1_1 and NEAT1_2 transcript. Forest plots show (9e) BCR, (90 MET, (9g) PCSM and (9h) GS>7 multivariable odds ratios for NEAT1_2 and (9i) BCR, (9j) MET, (9k) PCSM and (9l) GS>7 multivariable odds ratios for NEAT1_1 adjusted for clinicopathologic factors and adjuvant treatment (n=594). NEAT1 is found to contribute significant independent information for the prognostication of each endpoint.
Figures 9E, 9F, 9G, 9H:
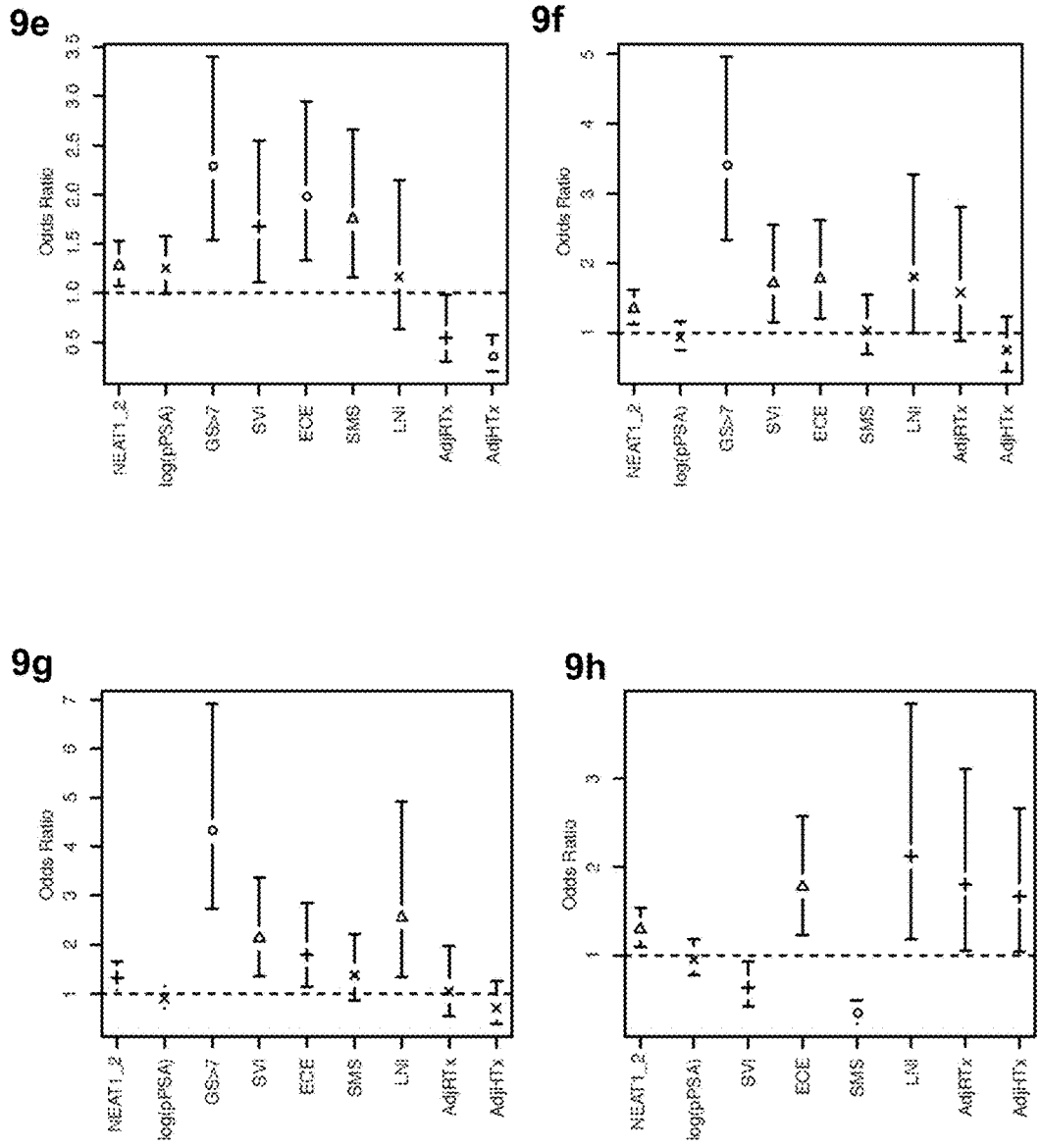
Figure 9I:
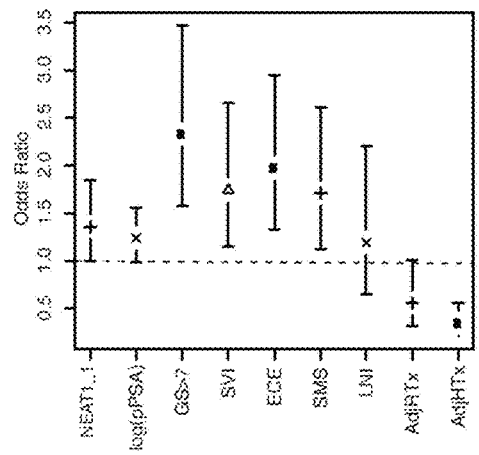
Figure 9J:
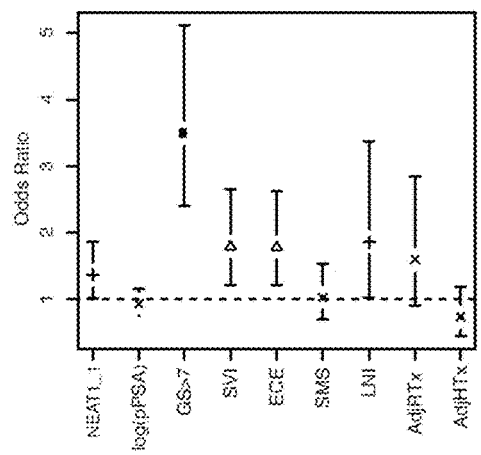
Figure 9K:
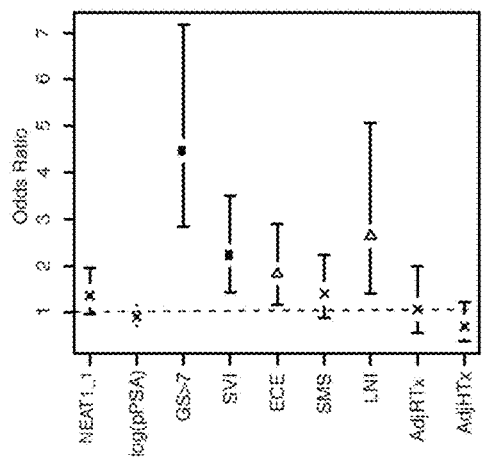
Figure 9L:
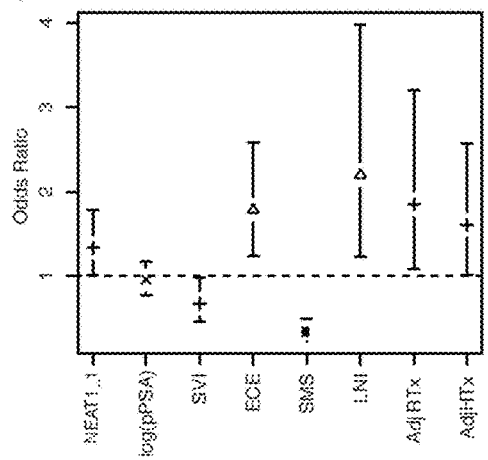

According to this aspect of the invention, the control level can be a pre-established value or values or a range of values, for example, based on clinical studies and statistical analysis. The control level may correlate with the NEAT expression levels in healthy individuals and/or individuals having localized prostate cancer and good clinical outcome after therapy in follow up studies. To illustrate without intending to be bound, a control value, in this case, a cut off value or cut point of NEAT levels, can be determined as described in the Examples herein-below. As described in the description of FIGS. 8a-8b, the cut points to define high and low NEAT1 expression were selected using patients from the Mayo nested case—control data set by maximizing the product of the sensitivity and specificity for each endpoint and to distinguish between low and highly aggressive cancer from indolent cancer. More specifically, two cut points were established for each the NEAT1 long and NEAT1 short expression based on log 2 expression determined in microarray expression analysis, with one for the BCR endpoint and one for the MET endpoint:
BCR—Long—8.77
MET—Long—9.08
BCR—Short—10.22
MET—Short—10.22

In still another aspect, this disclosure provides a diagnostic method for determining the stage of cancer, including for example, the likelihood that the prostate cancer is an advanced stage cancer. According to this aspect, the NEAT1 level in a biological sample of the subject relative to a control level provides a basis for determining the cancer stage, with an elevated NEAT1 level correlating with a more advanced stage of prostate cancer.

Figures 7A, 7B, 7C, 7D:
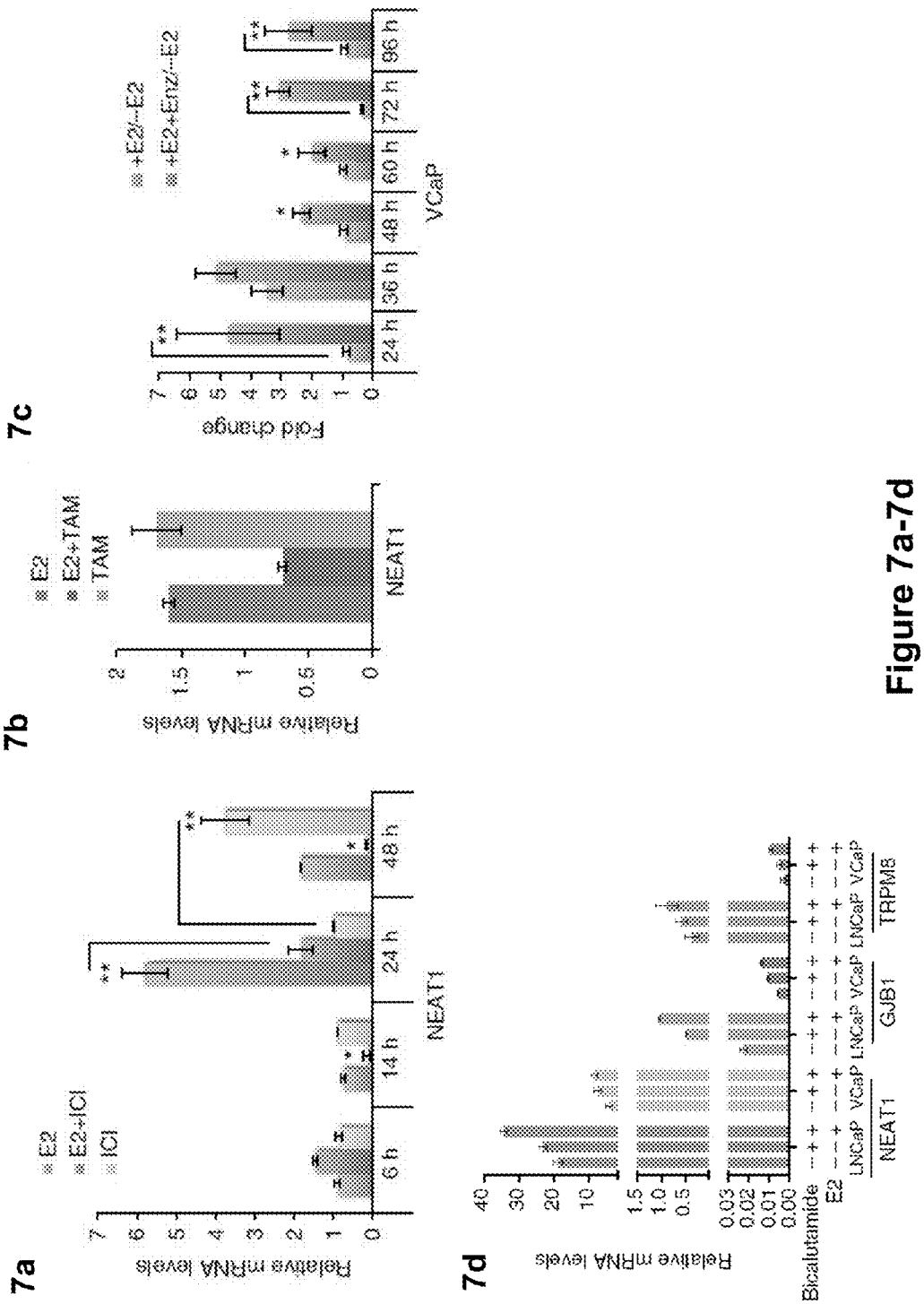
FIG. 7a-f. NEAT1 in therapy resistance. (7a) NEAT1 expression in VCaP cells treated with E2 (10 nM) at different time points alone, E2+ICI (10 nM+10 µM) or ICI (10 µM) alone. Results are expressed as the mean±s.d. of three independent experiments. * p<0.05, **p<0.01, Student's t-test. (7b) NEAT1 expression in VCaP cells treated with E2, E2+4OHT (10 nM+10 nM), and 4OHT (10 nM) alone for 48 h. (7c) NEAT1 expression in VCaP cells treated with or without E2 (10 nM) or E2+Enzalutamide (10 n1M+10 µM) at different time points. Results are expressed as the mean±s.d. of three independent experiments. *p<0.05 and **p<0.01, Student's t-test. (7d) qRT-PCR analysis of NEAT1, GJB1 and TRPM8 in LnCaP and VCaP control cells, with bicalutamide treatment (10 µM) alone or in combination with E2 (10 nM) for 48 h. Results are expressed as the means±s.d. of three independent experiments. Vertical bars represent range of data. Results were reproducible between representative experiments. (7e) Quantitation for the RNA ISH signals for RNA ISH of NEAT1 in benign, localized PCa and in advanced disease shown in using RNA Spot Studio. (7f) Scatter plot showing the correlation between ERα and NEAT1 expression by qRT PCR in 9 cases of benign prostate, 7 PCa, and 7 CRPC. Pearson's correlation coefficient R=0.86 (p-value=1.9e-07).
Figures 7E, 7F:
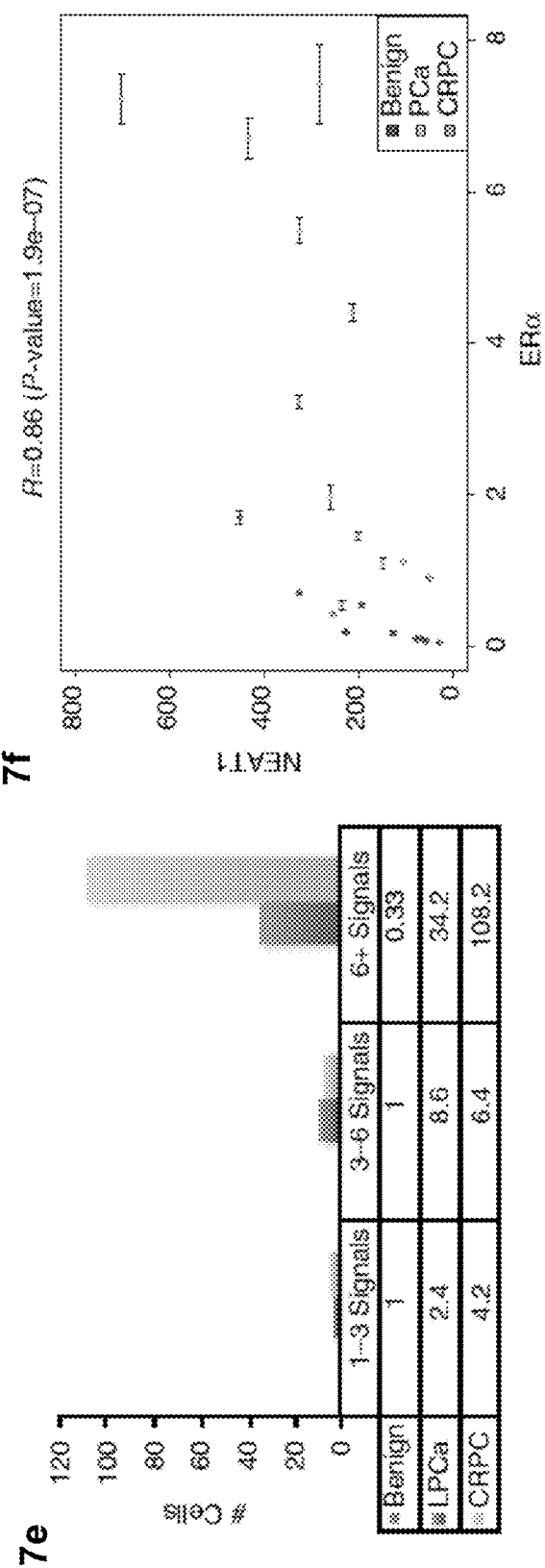

The present inventors have demonstrated that NEAT1 levels are elevated in localized prostate cancer, and are more significantly elevated in advanced prostate cancer such as CRPC (see, e.g., FIGS. 7e-7f). Thus, the NEAT expression level can be used as an independent diagnosis parameter, and can also be integrated in a multi-parameter panel for diagnosis.

Similar to other aspects of the invention, the control level according to this aspect of the invention can be a pre-established value or values or a range of values, for example, based on clinical studies and statistical analysis. The control level may correlate with the NEAT expression levels in healthy individuals in certain embodiments, and with individuals having a less advanced and less aggressive prostate cancer in other embodiments.

Sample sources suitable for use include any biological specimen that may contain prostate cancer cells, such as tissue, urine, blood, semen, prostatic secretions or prostate cells. Methods of procuring cell and tissue samples are well known to those skilled in the art, including, for example, tissue sections, needle biopsy, surgical biopsy, and the like. For a cancer patient, cells and tissue can be obtained from a tumor. A cell or tissue sample can be processed to extract, purify or partially purify, or enrich or amplify the nucleic acids in the sample for further analysis. In a specific embodiment, a urine sample is collected immediately following a digital rectal examination (DRE), which often causes prostate cells from the prostate gland to shed into the urinary tract. Samples obtained from the above-identified sources can be further processed, for example, to enrich for prostate cancer cells or extract the nucleic acid or protein molecules from the cells. The processing may include obtaining the serum or plasma portion of blood, obtaining the supernatant or cell pellet portion of urine, homogenization of tissue, lysis of cells, and the like.

Suitable assays for detecting and determining the levels of NEAT1 include, but are not limited to, Northern blot, RNA ISH (for in situ hybridization), RT-PCR (for reverse transcriptase mediated polymerase chain reaction, including quantitative RT-PCR or "qRT-PCR"), and RNA-Seq, all of which have been well known to the skilled artisan and are also illustrated in the Examples section below.

Performance of any of the assays may involve the use of a nucleic acid oligonucleotide (a probe for hybridization, or a primer or a pair of primers for PCR) that is specific for NEAT1.

By "oligonucleotide specific for NEAT1", it is meant that the oligonucleotide is sufficiently complementary to NEAT1 in sequence (e.g., 80%, 85%, 90%, 95%, 96%, 97%, 98%, 99% or 100% complementary or forming base pairs), such that the oligonucleotide hybridizes under stringent conditions to NEAT1 without significant non-specific hybridization to other molecules. The percentage of non-specific hybridization should be not more than 40%, 30%, 25%, 20%, 15%, 10% or 5%, to be considered insignificant. Stringency is dictated by temperature, ionic strength, and the presence of other compounds such as organic solvents. For example, "high stringency conditions" can encompass hybridization at 42° C. in a solution consisting of 5×SSPE (43.8 g/l NaCl, 6.9 g/l NaH2PO4H2O and 1.85 g/l EDTA, pH adjusted to 7.4 with NaOH), 0.5% SDS, 5×Denhardt's reagent and 100 µg/ml denatured salmon sperm DNA, followed by washing in a solution comprising 0.1×SSPE, 1.0% SDS at 42° C. or higher. "Medium stringency conditions" can encompass hybridization at 42° C. in a solution consisting of 5×SSPE with NaOH), 0.5% SDS, 5×Denhardt's reagent and 100 µg/ml denatured salmon sperm DNA followed by washing in a solution comprising 1.0× SSPE, 1.0% SDS at 42° C.

In some embodiments, an assay uses one or more oligonucleotides that are specific for the 5' portion of NEAT1 that is shared by both isoforms of NEAT1, which permits detection of both isoforms. In other embodiments, an assay uses one or more oligonucleotides that are specific for the 3' portion of the long isoform of NEAT1, which permits the detection of only the long isoform of NEAT1. In yet other embodiments, two or more oligonucleotides are use, at least one being specific for the long isoform, and at least another one being specific for the 5 ' portion of NEAT common to both isoforms.

According to this invention, one can detect and determine the levels of the long or short isoform of NEAT1 individually, or can detect and determine the collective levels of the long and short isoforms of NEAT1 in combination, based on appropriate choice of assays and oligonucleotides. The findings made by the inventors in respect to the relationship between the level of NEAT1 and prostate cancer, as illustrated in the Examples below, are consistent with the two isoforms. Thus, the diagnostic and prognostic methods disclosed above and herein can be practiced by detecting the level of either of the long or short isoform of NEAT1, or by detecting the combined levels of the long and short isoforms of NEAT1, and comparing to the respective controls.

Methods of Treatment

This disclosure also provides methods for treating prostate cancer.

The term "treating" as used herein includes inhibiting and retarding the growth and progression of prostate cancer, causing regression of prostate cancer, preventing or reducing the risk of recurrence post operation or treatment, and/or preventing or reducing the risk of prostate cancer progressing into an advanced stage.

The therapeutic methods of this invention are based on providing to a subject with an interfering RNA molecule that targets NEAT1. The subject include a subject who has been diagnosed with prostate cancer, especially prostate cancer at an advanced stage, including patients who are resistant to hormone therapy or other therapy targeting post castration, as well as subject who has been determined to have high levels of NEAT1.

Interfering RNA Molecules Targeting NEAT1

By "an interfering RNA molecule targeting NEAT1", it is meant that the interfering RNA molecule specifically interferes with the level or activity of NEAT1 (i.e., the NEAT1 RNA molecules) via RNA interference. RNA interference (RNAi) is a process by which double-stranded RNA (dsRNA) is used to silence gene expression. RNAi begins with the cleavage of longer dsRNAs into small interfering RNAs (siRNAs) by an RNaseIII-like enzyme, dicer. siRNAs are dsRNAs that are usually about 19 to 28 nucleotides in length and often contain 2-nucleotide 3' overhangs, and 5' phosphate and 3' hydroxyl termini. One strand of the siRNA, also referred to as the antisense strand, is incorporated into a ribonucleoprotein complex known as the RNA-induced silencing complex (RISC), which uses this siRNA strand to identify mRNA molecules that are at least partially complementary to the incorporated siRNA strand, and then cleaves these target mRNAs or inhibits their translation. Therefore, the antisense strand of an siRNA that is incorporated into RISC is known as the guide strand. The other siRNA strand, known as the passenger strand or the sense strand, is eliminated from the siRNA and is at least partially identical to the target mRNA.

Typically, an interfering RNA molecule includes a strand that corresponds to, i.e., substantially identical with, a portion of the DNA sequence coding for the NEAT1 RNA. That is, an interfering RNA molecule includes a strand having a sequence substantially complementary to a portion of NEAT1 (RNA). The portion of NEAT1 to which an interfering RNA molecule is substantially complementary to, is also referred to herein as the target sequence or target site.

In certain embodiments, target sequences within NEAT1 are selected using design tools and techniques available in the art, for example, those by Tuschl, T. et al., "The siRNA User Guide," available on the Rockefeller University web site; by Technical Bulletin #506, "siRNA Design Guidelines," at Ambion Inc. web site. Parameters for selection can include G/C contents between 35% and 55% and siRNA lengths between 19 and 27 nucleotides. Interfering RNAs corresponding to a selected NEAT1 target sequence can be tested in knock down experiments as described herein.

Examples of suitable target sequences within NEAT1 include those to which the siRNAs of SEQ ID NOS: 3-11, SEQ ID NO: 43 and SEQ ID NO: 45 correspond to. For example,

| Sequence of Sense Strand of siRNAs in NEAT1 | Start Site |
|---|---|
| UGGUAAUGGUGGAGGAAGAUU (SEQ ID NO: 3) | 998 |
| GUGAGAAGUUGCUUAGAAAUU (SEQ ID NO: 4) | 2352 |
| GGAGGAGUCAGGAGGAAUAUU (SEQ ID NO: 5) | 366 |
| GCCUUUACUACAUGUGUGA (SEQ ID NO: 43) | 3266 |
| CUUAGAACUUUAAGUGCAA (SEQ ID NO: 45) | 2383 |

As described, an interfering RNA molecule includes a strand having a sequence substantially complementary to a portion of NEAT1 (RNA). For example, a double stranded siRNA molecule can contain a sense nucleotide strand that includes a region substantially identical in sequence to a target sequence of NEAT1, and an antisense nucleotide strand substantially complementary to the same target sequence of NEAT1. By "substantially identical", it is meant at least 85%, 90%, 95%, 98% or 99% identity in sequence, or that the differences are not more than 5, 4, 3, 2, or 1 nucleotides between the target sequence of NEAT1 and a region of the sense strand of an interfering RNA. Similarly, by "substantially complementary" it is meant at least 85%, 90%, 95%, 98% or 99% complementarity between the target sequence of NEAT1 and a region of the antisense strand of an interfering RNA. "100%" or "perfect" contiguous complementarity is standard Watson-Crick base pairing. The region of the sense or antisense strands that is substantially identical or complementary to the target sequence of NEAT1 can be at least 13, 14, 15, 16, 17, 18, 19, 20 or more contiguous nucleotides. An interfering RNA molecular may also include a region or regions of one or more bases that is (are) not substantially identical or complementary to target sequence within NEAT1, e.g., the 3',5' or both ends of a substantially identical or complementary region. A region can be one or more bases or at least two bases.

In some embodiments of the present invention, an interfering RNA molecule provided to a subject having prostate cancer is an siRNA molecule that targets NEAT1.

In some embodiments, the siRNA of the invention is a double-stranded nucleic acid molecule comprising two nucleotide strands, each strand having 18 to 30 nucleotides (i.e., 18, 19, 20, 21, 22, 23, 24, 25, 26, 27, 28, 29 or 30 nucleotides). One or both of the strands of double-stranded siRNA may have a 3' overhang of from 1 to 6 (i.e., 1, 2, 3, 4, 5 or 6) nucleotides, which may be ribonucleotides or deoxyribonucleotides or a mixture thereof. In one embodiment, the siRNA comprises a 3' overhang of TT or UU. In another embodiment, the siRNA comprises at least one blunt end. Specific examples of suitable double stranded siRNAs targeting NEAT1 include those whose sense strands are set forth in Table 2 as SEQ ID NOS: 3-11, SEQ ID NO: 43 and SEQ ID NO: 45.

In other embodiments, the siRNA molecule provided to a subject is a single stranded siRNA molecule of 18 to 30 nucleotides. Examples of suitable single stranded siRNA molecules include those that comprise a sequence that is complementary to any of the sense strands as set forth in SEQ ID NOS: 3-11, SEQ ID NO: 43 and SEQ ID NO: 45.

In still other embodiments, an interfering RNA molecule provided to a subject is a short hairpin RNA (shRNA) that targets NEAT1. A hairpin interfering RNA is a single molecule (e.g., a single oligonucleotide chain) that comprises both the sense and antisense strands of an interfering RNA in a stem-loop or hairpin. Examples of shRNAs include those having a sense sequence as set forth in Table 2, and an antisense sequence substantially complementary to the sense sequence.

In other embodiments, an interfering RNA molecule provided to a subject is another interfering RNA molecule and RNA-like molecule that can interact with RISC and silence gene expression. Examples of such other interfering RNA molecules include microRNAs (miRNAs) and dicer-substrate 27-mer duplexes. Examples of RNA-like molecules that can interact with RISC include siRNA, single-stranded siRNA, microRNA, and shRNA molecules containing one or more chemically modified nucleotides, one or more non-nucleotides, one or more deoxyribonucleotides, and/or one or more non-phosphodiester linkages.

In some embodiments, a single interfering RNA molecule targeting NEAT1 is provided to the patient. In other embodiments, two or more interfering RNA molecules targeting NEAT1 are provided.

Interfering RNAs may be generated by chemical synthesis, by in vitro transcription, or by cleavage of longer double-stranded RNA with dicer, for example. Interfering RNAs can also be expressed in cells from plasmid or viral expression vectors or units, many available from commercial sources. Examples of commercially available plasmid-based expression vectors for shRNA include members of the pSilencer series (Ambion, Austin, Tex.) and pCpG-siRNA (InvivoGen, San Diego, Calif.). In the Examples section below, the inventors made four double stranded siRNAs (see Table 2) using RNA interference lentiviral vectors from ABM (Applied Biological Materials Inc., Richmond, BC, Canada). Unlike conventional shRNA vectors, the RNA interference lentiviral vectors from ABM employ dual convergent promoter system—the sense and antisense strands of the siRNA, which are cloned into a lentiviral vector, are expressed by two different promoters in the vector, rather than expressed as a single strand transcript that folds itself into a hairpin loop.

Nucleotides in interfering RNAs may be modified on their base portion, sugar portion, or the phosphate portion, for improved function, stability, delivery, or targeting.

Delivery Systems for Interfering RNAs Targeting NEAT1

Interfering RNAs targeting NEAT1 can be administered directly to a patient (e.g., via intratumoral injection), via a viral vector (which upon administration to a patient gains entry into the cells and expresses the desired interfering RNA molecule in the cells), or via non-viral delivery system. See review by Rao (2009). Non-viral delivery systems typically employ polymeric vehicles that are made of synthetic polymers, natural or biodegradable polymers, or lipids. The delivery vehicles may take the form of nanoparticles. A number of nanoparticle delivery systems have been described for successful delivery of interfering RNAs; see, e.g., Hong (2011), Xu (2013), Fredman (2015), and review by Rao (2009), the contents of all of which are incorporated herein by reference. A microfluidic platform for combinatorial synthesis and optimization of targeted nanoparticles is also described by Valencia (2013), incorporated herein by reference.

In some embodiments, the interfering RNA molecules targeting NEAT1 are conjugated (or form a complex) with PLA and/or PLGA based nanoparticles for delivery, such as nanoparticles described in Xu (2013) or Fredman (2015), or derived or modified therefrom.

In other embodiments, the interfering RNA molecules targeting NEAT1 are conjugated (or form a complex) with flexible TEA (Trietholamine) core PAMAM dendrimers, such as those described by Liu (2009), incorporated herein by reference.

Pharmaceutical Compositions and Administration

In certain embodiments, the invention provides pharmaceutical compositions (also referred to herein as "compositions") containing an interfering RNA molecule of the invention, or containing a conjugate or complex of a delivery system with an interfering RNA molecule of the invention, provided or formulated in a suitable physiologically or pharmaceutically acceptable carrier, such as water, buffer, saline, glycine, hyaluronic acid, mannitol, and the like. The compositions can be formulated as solutions, suspensions, or emulsions, for administration.

An interfering RNA molecule is administered to a patient at an effective amount, i.e., an amount of interfering RNA that produces a therapeutic response in a recipient mammal An effective amount of a formulation may depend on factors such as the age, gender, condition of the recipient, the potency and stability of the interfering RNA, and the type of delivery vehicles used, for example. Generally speaking, an interfering RNA can be provided to a recipient at 0.02-0.5 nmoles, 0.03-0.4 nmoles, or 0.04-0.3 nmoles, per administration; i.e., at least 0.02, 0.03 or 0.04, and not more than 0.5, 0.4 or 0.3 nmoles, nmoles per administration. The precise amount of a formulation that is therapeutically effective can be ascertained by one of ordinary skill in the art.

Suitable routes for administration of an interfering RNA molecule, a delivery system, or a pharmaceutical composition, include but are not limited to aerosol, intradermal, inhaling, intramuscular, intranasal, intravenous, intraperitoneal, intratumoral, for example.

Combination Therapy

In another aspect, the NEAT1 targeting therapeutic treatment described hereinabove is combined with one or more other therapeutic treatments conventionally used for prostate cancer. Generally, treatment for subjects diagnosed with prostate cancer includes cytotoxic chemotherapy, radiation, a therapy targeting androgen receptor mediated signaling.

Because ER/NEAT1 mediated signaling has been determined herein to be independent of androgen receptor (AR) mediated signaling, a treatment scheme that combines a therapy targeting NEAT1 with a therapy targeting androgen receptor mediated functions is particularly advantageous.

Therapy targeting androgen receptor mediated functions includes androgen deprivation therapy, which lowers the levels of hormones associated with prostate cancer progression, such as androgens. See, e.g., de Bono (2011); and Scher (2012). Androgen deprivation therapy includes, for example, treatment with anti-androgen agents, e.g., a gonadotropin-releasing hormone (GnRH) agonist (such as goserelin or leuprolide). Therapy targeting androgen receptor mediated functions also includes treatment with an agent directly targeting AR (i.e., to an agent that inhibits androgen receptor function, activity or expression), which includes small molecules, antibodies, antisense nucleic acid molecules, and interfering RNAs such as siRNA, shRNA, and miRNA. Therapy targeting androgen receptor mediated functions also includes treatment with an agent that suppresses local synthesis of androgenic steroids in the prostate, e.g., CYP17 inhibitors, such as abiraterone acetate (Zytiga), TAK-700 (orteronel), TOK-001 (galeterone) or VT-464. A wide variety of therapeutic agents targeting androgen receptor mediated functions, including agents directly targeting AR, have been described in U.S. Pat. Nos. 4,097,578, 5,411,981, and 5,705,654, U.S. Published Applications 2004/0009969 and 2007/0004753, and PCT international applications published as WO 97/00071, WO 00/17163 and WO 06/124118, the entire contents of which are incorporated herein by reference. Androgen deprivation may also include castration in the form of surgical castration (orchiectomy, i.e., surgical removal of testes) or chemical castration.

The present description is further illustrated by the following examples, which should not be construed as limiting in any way. The contents of all cited references (including literature references, issued patents, and published patent applications as cited throughout this application) are hereby expressly incorporated by reference.

EXAMPLE 1

Material and Methods

Cell culture and treatments: LnCaP and PC3 cells were grown in RPMI 1640 (Invitrogen) and supplemented with 10% fetal bovine serum (FBS) and 1% penicillin-streptomycin. RWPE1 cells were grown in Keratinocyte Serum Free Medium (K-SFM), Kit (Gibco, #17005-042). VCaP and DU145 cells were grown in DMEM (Invitrogen) and supplemented with 10% fetal bovine serum (FBS) with 1% penicillin streptomycin. NCI-H660 cells were grown in RPMI 1640 supplemented with 0.005 mg/ml insulin, 0.01 mg/ml transferrin, 30 nM sodium selenite, 10 nM hydrocortisone, 10 nM β-estradiol, 5% FBS, 1% penicillin-streptomycin and an extra 2 mM of L-glutamine (for a final concentration of 4 mM). For cell treatments in several experiments, the inventors used 10-100 nM β-estradiol (Sigma Aldrich), 10 μM Enzalutamide (Astellas), 10 μM bicalutamide (Sigma Aldrich), 1-10 nM R1881 (PE Biosystems), 10-100 nM 4-hydroxy tamoxifen (4OHT) (Sigma Aldrich), 1-10 μM ICI 182,720 (Tocris Bioscience).

Plasmids, siRNAs and transfection: pcDNA 3.1, pcDNA3.1-ERα, pcDNA 3.1 AR, piLenti-GFP, piLenti-NEAT1 siRNA-GFP (set of four, sequences provided in Table 2), iLenti-si-scrambled, pLenti-bicistronic-luc-NEAT1. siRNAs for ERα, ER, AR, NEAT1, NEAT1_2 were used and the sequence is provided in Table 2. For the mammalian expression vectors Lipofectamine 3000 (Invitrogen) and Lonza nucleofection were used for transfection. The stable clones for NEAT1 overexpression as well as the scrambled and NEAT1 siRNA expressing cells were generated by using the lentiviral vectors and by selection in puromycin.

Identification of ERα-regulated lncRNA: A set of known lncRNAs was generated from various data sources: RefSeq: GENCODE v7;—ncRNA.org; and lncRNAdb (Amaral (2011)) and those that were at least 200 nt long were selected, resulting in 12,483 lncRNAs. These lncRNAs were characterized according to their potential of being regulated by ERα by using ERα binding sites information from ChIP-seq experimental data. Moreover, several histone marks were considered to provide evidence of transcription, including H3K4me3 and H3K36me3.

Differential expression analysis: In order to prioritize the experimental validation of lncRNAs, a pair-wise differential expression analysis was performed on the expression values determined by paired-end transcriptome sequencing of 73 samples (26 benign prostate, 40 PCa, and 7 NEPC). A pair-wise Wilcoxon test was performed and all p-values were corrected for multiple hypotheses testing using Benjamini-Hochberg (Benjamini (1995)).

ERα and NEAT1 signature via Oncomine concept analysis: RNA sequencing was done for VCaP and VCaP ERα-expressing cells as well as in vector control and NEAT1 overexpressing VCaP cells. The expression of the genes was computed and those genes with a log 2-fold change greater than 2 were selected. 588 genes were found to be overexpressed in VCaP ERα cells. A custom concept of this gene list was generated in Oncomine. Similarly, genes from the VCaP NEAT1 group with a log 2-fold change greater than 2 were selected and a custom concept was built in Oncomine using the top 1000 genes from NEAT1 signature. The significantly associated tumor vs. normal concepts with odds ratio >2.0 and $P<1\times10^{-6}$ considering tumor vs. normal analysis was determined. The resulting concepts and associations are represented through a concept network using Cytoscape version 2.8.2. Each node represents a concept to which the signature is associated at a greater than 3-fold odds-ratio for ERα signature and >2 fold odds ratio for NEAT1 signature. Node size reflects the concept size, i.e. the number of genes in each concept; red and green colors represent correlation with over- or under-expressed genes in the concept, respectively; and edge thickness represents the odds—ratio of the association between concepts, ranging from 1.4 to 29.9 and 1.2 to 637 for ERα and NEAT1 signatures, respectively. The border color of each node represents the tumor type. The layout of the network is based on the Edge-weighted spring-embedded algorithm.

Luciferase reporter assays: For ERE luciferase assays, VCaP cells were transiently transfected with the (ERE)3-5V40-luc reporter plasmid and/or ERα and/or AR as well as an internal control construct pRL harboring the *renilla* luciferase gene. VCaP cells were also transfected with empty vector or NEAT1 promoter (1+2) luciferase reporter constructs alone or with ERα as well as an internal control construct pRL harboring *renilla* luciferase gene. In order to determine the PSMA reporter activity, 293T cells and PC3 cells were co transfected with empty vector or PSMA luc and *Renilla*-luc reporter genes alone or with NEAT1, NEAT1+ERα, or NEAT1+AR.

24 h post transfection the media was changed to 5% charcoal stripped media and the cells indicated were treated with E2 (10 nM) or R1881 (1 nM) for 14 h. At 48 h cells were lysed with passive lysis buffer and luciferase activities were measured using the dual luciferase system (#E1910, Promega) and normalized with *renilla* luciferase activity.

RNA in situ hybridization for NEAT1: RNA ISH for NEAT1 was performed on 5 benign, 5 PCa and 3 CRPC cases using kits and probes designed by Advanced Cell Diagnostics. Briefly, the single-color chromogenic detection assay uses pairs of specially designed oligonucleotide probes that, through sequence-specific hybridization, recognize both the specific target NEAT1 RNA sequence and the signal amplification system. Unique target probe oligonucleotides were designed to hybridize in tandem to the target RNA. Cross-hybridization to other sequences is minimized by screening against the entire human RNA sequence database.

The signal amplification system consists of the preamplifier, amplifier, and enzyme-conjugated label probe, which assemble into a tree-like complex through sequential hybridization. Signal amplification occurs at target sites bound by probe pairs only. Nonspecific off-target binding by single probes does not result in signal amplification.

All steps of NEAT1 RNA ISH staining of the slides are performed manually, optimized in tissue microarrays (TMAs). Briefly, formalin-fixed, paraffin-embedded (FFPE) unstained tissue sections (5 μm) were mounted on positively charged microscopic glass slides, deparaffinized in xylene and rehydrated through a series of alcohols. The rehydrated sections were treated with 3% hydrogen peroxide at room temperature for 10 minutes to block endogenous peroxidase. Sections were then boiled in 1×citric buffer (10 nmol/L Nacitrate, pH 6.0) for 15 minutes and incubated with protease (2.5 mg/mL; Sigma Aldrich, St. Louis, Mo.) at 40° C. for 30 minutes. The slides were hybridized sequentially with target probes (20 nmol/L) in hybridization buffer A (6× saline sodium citrate [SSC] buffer [1×SSC is 0.15 mol/L NaCl and 0.015 mol/L Na-citrate], 25% formamide, 0.2% lithium dodecyl sulfate [LDS], and blocking reagents) at 40° C. for 2 hours, signal preamplifier in hybridization buffer B (20% formamide, 5×SSC, 0.3% LDS, 10% dextran sulfate, and blocking reagents) at 40° C. for 30 minutes, amplifier in hybridization buffer B at 40° C. for 30 minutes, and horseradish peroxidase- or alkaline phosphatase-labeled probes in hybridization buffer C (5×SSC, 0.3% LDS, and blocking reagents) at 40° C. for 15 minutes.

Hybridization signals were detected under bright field microscope as red colorimetric staining (using Fast Red chromogen, BioCare Biomedical, Concord, CA) followed by counterstaining with hematoxylin. Signals were granular and discrete red signals corresponding to individual lncRNA targets. The signals were scored using the RNA Spot Studio software.

Chromatin immunoprecipitation: All ChIP experiments were carried out using Millipore EZ-*Magna* ChIP kit (Catalogue #17-10086). Briefly 5-10×10$^6$ cells were crosslinked with 1% formaldehyde for 10 min at room temperature. The crosslinking was then quenched with 0.125 M glycine. Chromatin was sonicated in the lysis buffer to 300-500 bp and the extraction of ChIP DNA was done as per the kit protocol. Antibodies used include ERα (AC-066-100, diagenode, 514), AR (06-680, Millipore, 514), H3K4me3 (ab8580, Abcam, 514), H3K9me3 (ab8898, Abcam, 514), H3K36me3 (ab9050, Abcam, 5 μg), H3K27me3 (07-449, Millipore, 514), and Ace-H3 (no. 06-599, Millipore, 5 μg).

ERα ChIP was also performed in crosslinked VCaP cells with E2 treatment for 0, 14 h and 48 h. In VCaP ERα cells E2 treatment was for 6 h, 14 h and 48 h.

Chromatin Isolation by RNA Purification (ChIRP): Chromatin immunoprecipitation for NEAT1 was done in VCaP control and NEAT1 expressing cells with and without E2 treatment using the ChiRP protocol (Chu (2012)). Briefly, biotin TEG antisense oligos were generated using singlemoleculefish.com for NEAT1, Lac Z and scrambled NT NEAT1 (see also Table 4). The NEAT1 probes were divided into 2 pools. Cells cross-linked in 1% gluteraldehyde were lysed and sonicated. The biotinylated probes were hybridized followed by RNA and DNA isolation. qPCR was performed on the DNA samples.

Preparation of NEAT1 RNA ISH probe: The full length NEAT1 gene was cloned in pCRII-TOPO (Invitrogen) vector. The plasmid was digested with NotI (New England Biolabs) and purified with the Qiaquick PCR Purification Kit (Qiagen) according to manufacturer's protocol. In vitro transcription was accomplished using 500 ng of linearized plasmid DNA and the MEGAscript SP6 kit (Ambion) as directed by the manufacturer. The resultant RNA was cleaned using the RNeasy kit (Qiagen) using the manufacturer's protocol. 5 ug of RNA was mixed with 10 ul of buffer A, 5 μl of ML DNP reagent (both provided by Ventana-Roche) and water to 50 μl. The reaction was incubated at 37° C. for two hours. The labeled RNA was cleaned with the RNeasy Kit (Qiagen). 50-250 ng/ml of probe was mixed in Ribohybe solution (Ventana-Roche) and 100 ul of the probe was used for each slide. RNA in situ hybridization on FFPE slides was performed using an automated protocol developed for the Discovery XT automated staining system (Ventana-Roche).

RNA-ISH for NEAT1 on cell lines: Cells were grown on a 15 mm, poly-L-lysine coated glass coverslip. At ~70% confluence cells were serum starved in 8% charcoal stripped media for 48 h, followed by 48 h treatment with 10 nM E2. At the end of treatment, cells were fixed in 4% formaldehyde, dehydrated by an ethanol gradient (50-100%) and stored at −20° C. For the hybridization assay cells were rehydrated by an ethanol gradient (100-50%) into PBS. Between subsequent steps cells were washed with PBS. The Affymetrix QuantiGene ViewRNA ISH cell assay kit was used for NEAT1 staining. Cells were permeabilized by 5 min incubation at RT in Detergent Solution QC, and digested for 10 min at RT by Protease QS (1:4000 in PBS). Then the target specific Probe Set (1:100 in Diluent QF) was allowed to hybridize for 3 h at 40±1° C. Between subsequent steps cells were washed by soaking in Wash Buffer. Sequential hybridization steps were conducted for signal amplification-PreAmplifier Mix (1:25 in Diluent QF), Amplifier Mix (1:25 in Diluent QF) and Label Probe Mix (1:25 in Diluent QF) each incubated 30 min at 40±1° C. After 2 10 min washes in Wash Buffer, nuclei were stained with DAPI and cover slips were mounted to slides with Prolong Gold Antifade Reagent (Life Technologies) for visualization.

Proliferation assay: Cell proliferation was assessed using the CyQUANT NF cell proliferation assay kit (Life Technology). Cells were seeded in 96-well plates at 3-4×10$^4$ cells per well. Cells were incubated in DMEM media with 10% FBS for 24 h. The cells were then serum starved in 8% charcoal stripped DMEM medium for 48 h followed by E2 treatment at 10 nM concentration for indicated time points. The media was then aspirated and replaced with the dye binding solution followed by incubation for 30-60 minutes. The fluorescence was then measured in a microplate reader using excitation at 485±10 nm and fluorescence detection at 530±15 nm. The assay was performed in triplicates.

Invasion assay: The CHEMICON cell invasion assay kit (EMD MIlipore) was used for determining the cell invasion.

Cells were serum-starved for 48 hours and then seeded at a density of 2×10$^5$ cells/well in the upper well of the invasion chamber. 500 µl of phenol res free DMEM media supplemented with 8% charcoal stripped serum and 10 nM E2 was added to the lower chamber. After 48-hour incubation, the invaded cells were stained by dipping the inserts in the staining solution for 20 minutes. The stained cells were then dissolved in 10% acetic acid and transferred to a 96-well plate for colorimetric reading of OD at 560 nm.

Migration assay: The Cell Biolabs Inc. Radius™ 96-Well Cell Migration Assay was used to determine cell migration. Cells were serum-starved for 48 hours, then seeded to a pretreated (incubated 20 minutes in Radius™ Gel Pretreatment solution and washed with Radius™ Wash Solution) Radius™ 96-Well Plate at a density of 8×10$^4$ cells per well with or without E2 (10 nM). After 24 hours incubation, the Radius™ Gel Spot was removed via the Radius™ Gel Removal Solution and pre-migration images were captured. After 24 hours incubation, cells were stained with Cell Stain Solution and post-migration images were captured for analysis using the CellProfiler™ Cell Image Analysis Software (Broad Institute).

Statistical analysis: The Wilcoxon test was employed with Benjamini-Hochberg (Benjamini (1995)) correction for multiple hypotheses for pair-wise comparisons for differential expression analysis. The Chi-square test was used for comparison of proportions and the Pearson's correlation was used to compare the expression of selected genes. For quantitative real time PCR, the Delta CT value was computed according to the ABI qPCR protocol. To compare qPCR data a student's t-test was employed. Median-rank statistics results are reported for analyses with the Oncomine datasets (Rhodes (2004)).

Analysis of Mayo Clinic cohort: Affymetrix HuEx microarrays were used to analyze NEAT1 expression in two post-radical prostatectomy cohorts from the Mayo Clinic. Details on tissue preparation, RNA extraction, amplification, hybridization, and clinical characteristics for these cohorts have been described previously (Erho (2013); Karnes (2013)). Both cohorts were filtered using the same criteria (patient either exhibiting preoperative prostate-specific antigen >20 ng/mL, Gleason score >8, pT3b, or GPSM (Blute (2001)) score >10) to increase the homogeneity of patient characteristics. The two sets were pooled to improve analytic power, resulting in a dataset of 594 patients. The patient characteristics of the pooled dataset can be found in Table 1.

A representative Probe Selection Region (PSR) for the genomic span of the short and long NEAT1 isoforms was selected by minimizing the technical variance across the pooled dataset. Based on these two PSRs, the prognostic performance of NEAT1 short and long isoforms was evaluated using univariable and multivariable odds ratios and area under the receiver operating characteristics curve (AUC) for BCR, MET, PCSM, and GS>7 endpoints. Kaplan Meier (KM) curves were used to perform survival analysis on the Mayo case-cohort patients only (Erho (2013)) since the nested case-control cohort (Blute (2001)) was not suitable for KM analysis.

RNA isolation, cDNA synthesis and PCR experiments: Total RNA was isolated from frozen prostate tissue samples (for qPCR) and cell lines (for transcriptome sequencing and qPCR) using Trizol (Invitrogen) with DNase I digestion according to manufacturer's instructions. RNA integrity was verified on an Agilent Bioanalyzer 2100 (Agilent Technologies). cDNA was synthesized from total RNA using Superscript III (Invitrogen) and random primers (Invitrogen). Quantitative RT-PCR was performed using Power SYBR Green Mastermix (Applied Biosystems) on an Applied Biosystems 7900 Fast Real Time PCR machine. All primers were designed using Primer 3 and synthesized by Integrated DNA Technologies.

RNA sequencing: Standard poly-A selected RNA sequencing was done for VCaP, VCaP ERα expressing cells as well as for VCaP cells overexpressing empty vector and VCaP NEAT1 overexpressing cell lines using Illumina TruSeq RNA-seq protocol. Reads were aligned to the reference genome NCBI36/hg18 without the minor haplotypes and the minor sequences using STAR aligner3. Reads mapped to the mitochondrial genome were removed. The expression of each gene (UCSC knownGenes) was computed using mrfQuantifier, part of RSEQtools4. The resulting expression data was used to identify variation in gene expression between VCaP and VCaP ERα cells and also between the vector control and NEAT1 expressing cells. The inventors computed the ratio between VCaP and VCaP ERα and control cells and VCaP NEAT1, after adding 1, and selected those genes with a log 2-fold change greater than 2.

ChIP sequencing: ERα ChIP followed by sequencing was performed in VCaP, VCaP+E2, VCaP ERa+E2 expressing cells and in NCI-H660 cells with and without E2 treatment. Cells were treated with E2 for 48 hrs. ChIP experiments were carried out using Millipore EZ-Magna ChIP kit (Catalogue #17-10086). Briefly 5-10×106 cells were crosslinked with 1% formaldehyde for 10 min at room temperature. The crosslinking was then quenched with 0.125 M glycine. Chromatin was sonicated in the lysis buffer to 300-500 bp and the extraction of ChIP DNA was done as per the kit protocol. For ChIP sequencing the concentrations of the ChIP DNA were quantified by Qubit Fluorometer (Invitrogen). ChIP DNA was prepared into libraries and direct sequencing of the ChIP libraries was performed using illumine Genome Analyzer according to standard manufacturers procedures.

ChIP seq data analysis: Peak detection for all ChIP-seq experiments was performed with ChIPseeqer5, using the same parameters for all datasets (i.e., p-value threshold for peaks=10-5, minimum distance between peaks=100 bp). Genomic annotation of ChIP-seq peaks, comparison between ChIP-seq datasets and motifs analysis were performed using the corresponding tools in the ChIPseeqer software. The binding sites were ranked according to their p-value as determined by ChIPSeeqer and considered the expression levels of the potential target genes. In this case, a target gene is defined if it is within 20 KB of the peak and considered only genes whose expression is higher than 1 in at least one condition (either VCAP con or VCAP ERα).

RNA extraction, sample preparation and sequencing: For RNA sequencing analysis frozen tissue was cored (1.5 mm biopsy cores) and RNA extracted using TRIzol Reagent (Invitrogen, CA). Tissues were obtained from radical prostatectomy series at the Weill Cornell Medical College. All samples were collected with informed consent of the patients and under an Institutional Review Board approved protocol. The extracted RNA was subjected to DNase treatment using a DNA-free™ Kit (Applied Biosystems/Ambion, Austin, Tex., USA). RNA quality was measured using the RNA 6000 Nano Kit on a Bioanalyzer 2100 (Agilent Technologies, Santa Clara, Calif., USA). RNA with RIN (RNA integrity number) >8 was used for subsequent library preparation. Illumina's sample preparation protocol for paired-end sequencing of mRNA was used. The paired end reads were then aligned to the human genome (hg18) using ELAND/CASAVA.

EXAMPLE 2

Results

ERα in Transcriptional Regulation of Prostate Cancer

To elucidate the role of ERα in prostate cancer, the inventors analyzed ERα protein and transcript levels in a panel of prostate cancer cell lines (n=5) and in a cohort of matched benign prostate tissue (n=14) and prostate adenocarcinoma (PCa) (n=14), respectively. The inventors observed that ERα was significantly upregulated (p=0.03) in prostate tumors compared with benign tissues (FIG. 1a). To determine the clinical relevance of ERα in prostate cancer, immunohistochemistry was performed using a tissue microarray composed of tissue cores from 64 samples of benign prostate tissue, 16 high-grade prostate intraepithelial neoplasia (HGPIN), 292 PCa, and 42 neuroendocrine prostate cancer (NEPC). While benign prostate had only low expression levels of ERα, ERα was detected in adenocarcinoma and the adjacent HGPIN through focal nuclear and cytoplasmic staining. ERα is overexpressed in a significant number of prostate cancer cohorts. It was also found to be overexpressed in prostate cancers with high Gleason score compared to those with low Gleason score as well as in those with tumor recurrence when analyzed via the Oncomine database (FIG. 1b). Analysis of subcellular distribution in prostate cancer cell lines revealed significant nuclear distribution of ERα in all cell lines tested. ERα protein levels were similar in both AR-positive LnCaP and VCaP cells (FIG. 1a, inset). The inventors used parental VCaP and the ERα-positive prostate cancer cell line NCI-H660 as model cell lines to further explore and delineate the specific contribution of ERα to prostate cancer. A ligand-dependent modulation of invasive potential was observed in VCaP cells upon estrogen (E2) treatment (FIG. 1c). These results suggest that a functionally relevant, ligand-dependent ERα signaling pathway is active in prostate cancer cell lines.

To further understand the impact of ERα, the inventors generated VCaP cells that overexpress ERα (VCaP ERα). Stable expression of ERα was confirmed by Western blot. VCaP ERα exhibited significantly higher invasive potential than VCaP parental cells or the vector control cells (FIG. 1c). Intriguingly, the noted effects of ERα overexpression were independent of AR status, as experimental silencing of AR in VCaP ERα cells did not compromise the increased invasive potential of E2-treated VCaP ERα cells (FIG. 1c). These data suggest that prostate cancer cells can utilize alternate nuclear receptor signaling (e.g., ERα signaling) to propagate, and understanding these mechanisms will help discern the complete spectrum of key regulators of prostate cancer progression.

Studies have established ERα's dominant role in transcriptional regulation of target genes in breast cancer. Likewise, high nuclear levels of ERα in prostate cancer cells and their direct association with chromatin implicate ERα in the transcriptional regulation of this cancer, as well. The inventors used ERα chromatin immunoprecipitation coupled with high-throughput sequencing (ChIP-seq) in VCaP cells, with and without E2 treatment, and also in VCaP ERα and NCI-H660 cells with E2 treatment to investigate the underlying mechanisms by which ERα might drive a transcriptional program in prostate cancer. The majority of ERα-binding sites were cell-specific. Analysis of the ChIP-seq data for ERα in NCI-H660 and VCaP ERα cells revealed that 64.9% of ERα binding occurred within intergenic regions of the prostate genome. This fraction is higher than the expected fraction if peaks were randomly distributed across the genome (p=3e-05).

Using publicly available datasets (Yu (2010)), the inventors found that 28% of the intergenic ERα binding sites in the prostate cancer genome (from VCaP ERα and NCI-H660 cell lines) overlapped with the active histone marks trimethylated lysine 4 of histone H3 (H3K4me3) and trimethylated lysine 36 of histone H3 (H3K36me3) (p<1e-7). On the other hand, 20.7% of those sites overlapped with histone marks typical of inactive chromatin, such as trimethylated lysine 9 of histone H3 (H3K9me3) or tri-methylated lysine 27 of histone H3 (H3K27me3). To prioritize experimental validation of ERα targets, the inventors ranked the peaks according to the average p-value determined by the peak-calling algorithm ChIPSeeqer (Giannopoulou (2011)) and selected the highest ranking peaks for further analysis. The inventors analyzed recruitment of endogenous ERα to the top 11 binding sites in parental VCaP cells (FIG. 1d) providing an experimental validation of the ChIP-seq data. A significantly higher recruitment of ERα was evident at the binding sites compared to control IgG.

Figures 1E, 1F:
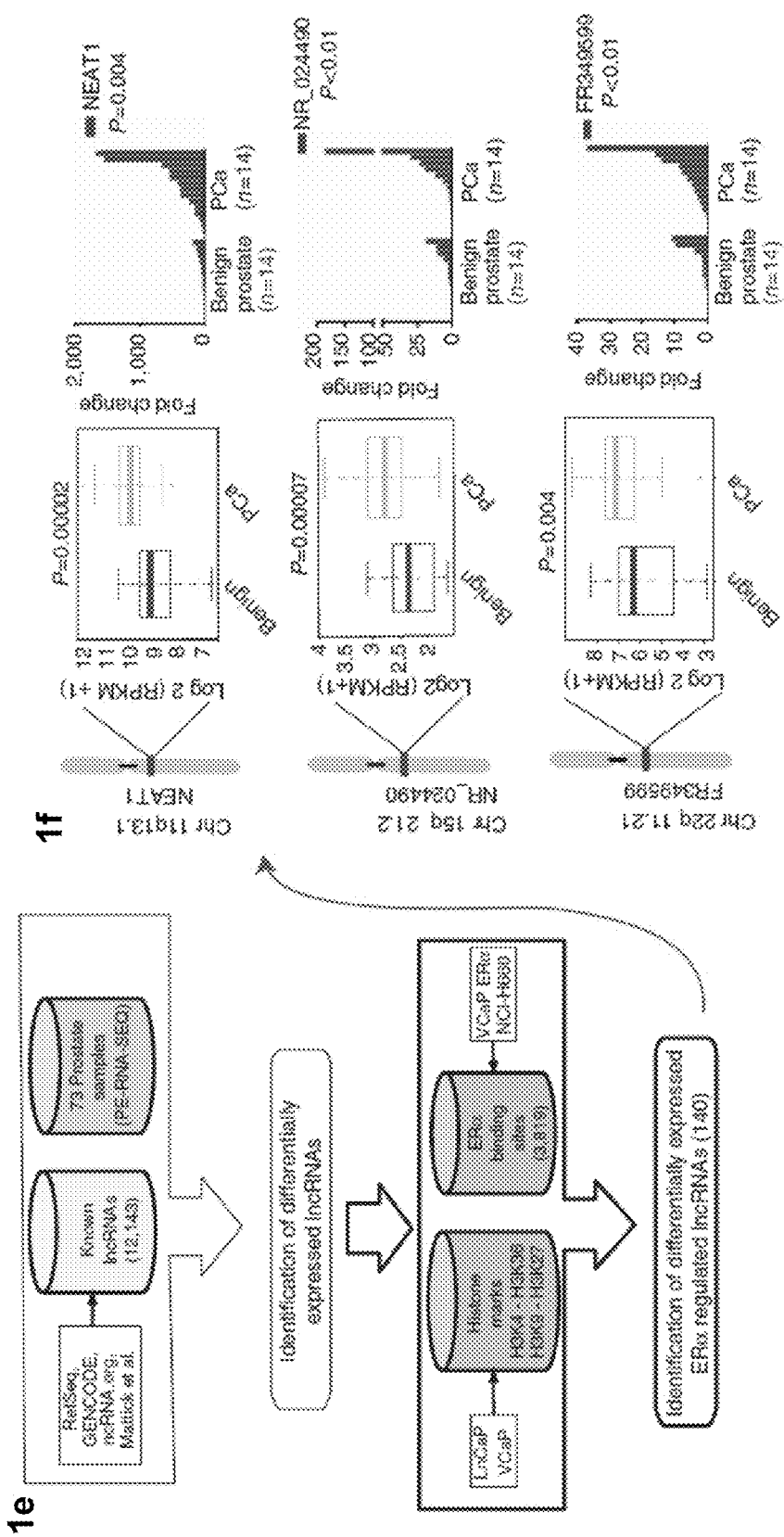

Given the enhanced recruitment of ERα to intergenic regions in the prostate genome, the inventors evaluated the likelihood that ERα might influence transcriptional output and thereby the repertoire of non-coding RNA in the context of prostate cancer. The inventors thus analyzed the abundance of non-coding transcripts in RNA-seq data derived from a cohort of 73 prostate tissues which included 26 benign prostate samples, 40 PCa, and 7 NEPC, focusing our analysis on 6,850 intergenic lncRNAs out of 12,143 known lncRNAs. The inventors identified 1,314 and 1,399 intergenic lncRNAs that were differentially expressed between benign and PCa and between PCa and NEPC, respectively (FDR<0.01). The inventors identified 140 intergenic lncRNAs putatively regulated by ERα (FIG. 1e). An analysis of AR binding sites (Yu (2010)) identified 98 lncRNAs that have an AR binding site within the promoter. This supported the view that ERα might significantly influence the non-coding transcriptome in prostate cancer. Using the RNA-seq data on VCaP and VCaP ERα cell lines to validate the expression levels of the top differentially expressed ERα-regulated lncRNAs, the inventors selected six potential candidate lncRNAs that had higher expression in VCaP ERα compared with VCaP. The inventors used quantitative real-time PCR (qRT-PCR) to validate expression for these six ERα regulated lncRNAs in VCaP and VCaP ERα-expressing cell lines. Expression of three of these lncRNAs was further determined in a cohort of 28 matched benign and prostate cancer samples, confirming upregulation of these three nominated lncRNAs in prostate cancer compared with benign prostate (FIG. 1f). Taken together, these analyses indicate that ERα is a transcriptional regulator of the non-coding transcriptome in prostate cancer.

Among the putatively ERα-regulated intergenic lncRNAs, the inventors identified Nuclear Enriched Abundant Transcript 1 (NEAT1) as the most significantly overexpressed lncRNA in prostate cancer versus benign prostate in our patient cohort (73 samples) (FIG. 1f). The NEAT1 gene is located on chromosome 11q13.1 and produces two RNA isoforms that overlap completely at the 5 end. The shorter isoform (hereafter abbreviated as NEAT1_1) is 3.7 kb in length and more abundant than the longer, 23 kb isoform (NEAT1_2) (Bonf (2009)). NEAT1 lncRNA is essential for the formation of subnuclear bodies called paraspeckles (Bond (2009)), and while both isoforms localize to paraspeckles, their physiological role in prostate cancer remains unknown.

ERα-regulated NEAT1 lncRNA is Upregulated in Prostate Cancer

The inventors analyzed the expression data of NEAT1 in the Oncomine database, and observed significant overexpression of NEAT1 lncRNA in several prostate cancer datasets (normal vs. cancer) and aggressive prostate cancer (FIG. 2a) (Arredouani (2009); Glinsky (2004); Grasso (2012); Lapointe (2004); LaTulippe (2002); Liu (2006); Luo (2001); Singh (2002); Taylor (2010); Tomlins (2007); Vanaja (2003); Varambally (2005); Wallace (2008); Yu (2004); Holzbeierlein (2004); Magee (2001); Tamura (2007); Welsh (2001)). The inventors first confirmed that amplification of chromosome 11q (where NEAT1 resides) was not seen across 109 adenocarcinoma cases (Barbieri (2012)), eliminating chromosome 11q13.1 amplification as an explanation for high NEAT1 expression (Cerami (2012); Gao (2013)). The expression of NEAT1 in two radical prostatectomy cohorts with long-term clinical follow-up from the Mayo Clinic (Erho (2013); Karnes (2013)) was measured using Affymetrix HuEx microarrays (see Methods). Table 1 contains the patient characteristics of the datasets.

Figures 2A, 2B, 2C, 2D:
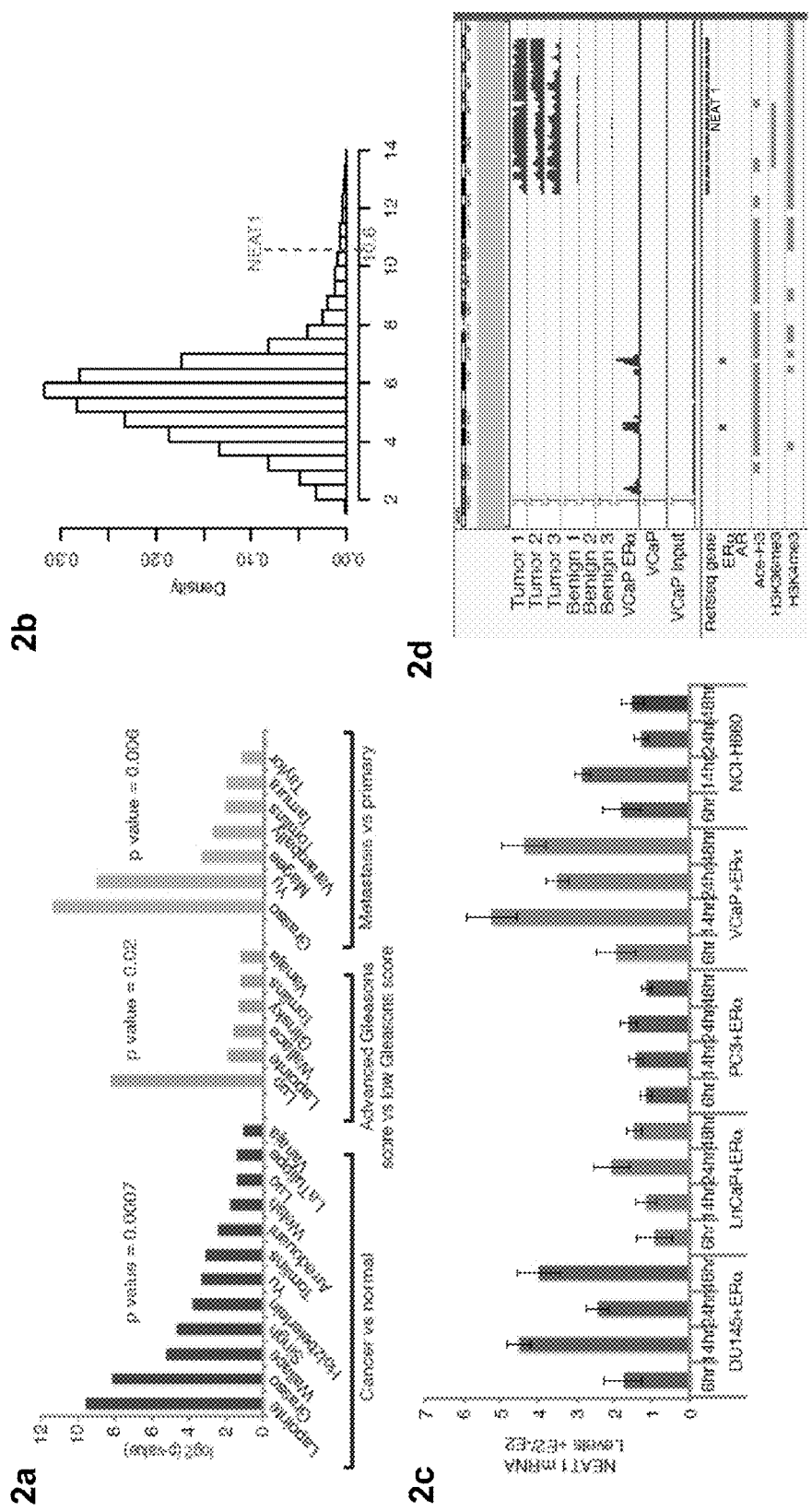
FIG. 2a-2g. ERα regulated NEAT1 lncRNA is upregulated in prostate cancer. (2a) NEAT1 is overexpressed in various prostate datasets (Oncomine). (2b) Distribution of the median expression of all genes (core transcript clusters) on the Human Exon 1.0 ST array in the pooled Mayo Clinic cohort (n=594). NEAT1's expression ranks in the 99th percentile of all genes on the array. (2c) Expression of NEAT1 with/without ERα overexpression and E2 treatment (10 nM) at different time points in a panel of prostate cancer cell lines. Results are expressed as the mean±s.d. of three independent experiments. (2d) View of NEAT1 genomic location indicates presence of two ERα binding sites in the promoter region. Read coverage tracks derived from RNA sequencing data indicates higher abundance of NEAT1 transcripts in PCa compared to benign tumors in 3 representative cases. The figure also reports the ChIP sequencing coverage tracks for ERα (VCaP ERα, VCaP and input DNA as control). The bottom panel shows the binding sites of ERα, AR (from Yu et al, GEO Accession GSM353651-tissueAR), Ace-H3, H3K4me3 and H3K36me3 in VCaP cell line (from Yu et al, GEO Accession GSM353629, GSM353620 and GSM353624), respectively. (2e) Chromatin immunoprecipitation followed by quantitative PCR to study ERα recruitment to NEAT1 promoter in VCaPcells with/without E2 treatment (10 nM) was performed with primers spanning the binding regions identified by ERα ChIP-seq data. Primers for non-specific region were used as negative control for ChIP studies. Results are expressed as the means of percentage of input±s.d. of two independent experiments. Vertical error bars represent the range of data. (2f) Luciferase based promoter reporter assays was utilized to analyze effect of ERα and/or AR on ERE-Luc promoter in VCaP cells. Cells were transiently transfected with the (ERE)3-SV40-luc reporter plasmid and/or ERα and/or AR treated with/without E2 or R1881 (1 nM) for 48 h. Results are expressed as the mean±s.d calculated from three independent experiments. (2g) Luciferase based promoter reporter assays was utilized to analyze NEAT1 promoter activity following ERα expression −/+E2 (10 nM) for 24 hr. Results are expressed as the means±s.d. calculated from three independent experiments. Error bars represent the range of data. Student's t-test was performed for comparisons where indicated and *p<0.05 and **p<0.01 was considered statistically significant.

NEAT1's expression ranked in the $99^{th}$ percentile of all genes on the microarray (FIG. 2b). The inventors determined levels of NEAT1 by RNA in situ hybridization (ISH) in a tissue microarray that included 16 benign prostate tissues, 21 PCa, 12 PCa with neuroendocrine differentiation, and 7 NEPC cases. NEAT1 was found to be highly expressed in prostate cancer compared with benign tissue.

The inventors observed that in a panel of prostate cancer cell lines ERα overexpression and E2 treatment upregulated NEAT1 transcript levels in a time-dependent manner (FIG. 2c). In DU145, an ERG-negative cell line, E2/ERα signaling was intact (FIG. 2c), supporting an ERG-independent phenomenon. Following ERα overexpression, the inventors recorded an increase in expression of the long isoform NEAT1_2, but to a lesser extent than the short form. This was not surprising as both isoforms of NEAT1 are driven by the same promoter (Nakagawa (2011)). Interestingly, knockdown of ER beta (ER) did not alter NEAT1 levels, suggesting that NEAT1 regulation is specific for ERα.

NEAT1 was originally identified with subnuclear organelles called paraspeckles that are free of chromatin and function as repositories of edited RNA and a number of nuclear RNA-binding proteins (Clemson (2009)). Loss of NEAT1 dramatically reduces the formation of paraspeckles. The inventors observed that treatment of the VCaP cells with E2 resulted in re-distribution of NEAT1 from paraspeckles to an enhanced distribution throughout the nucleus.

Figure 2E:
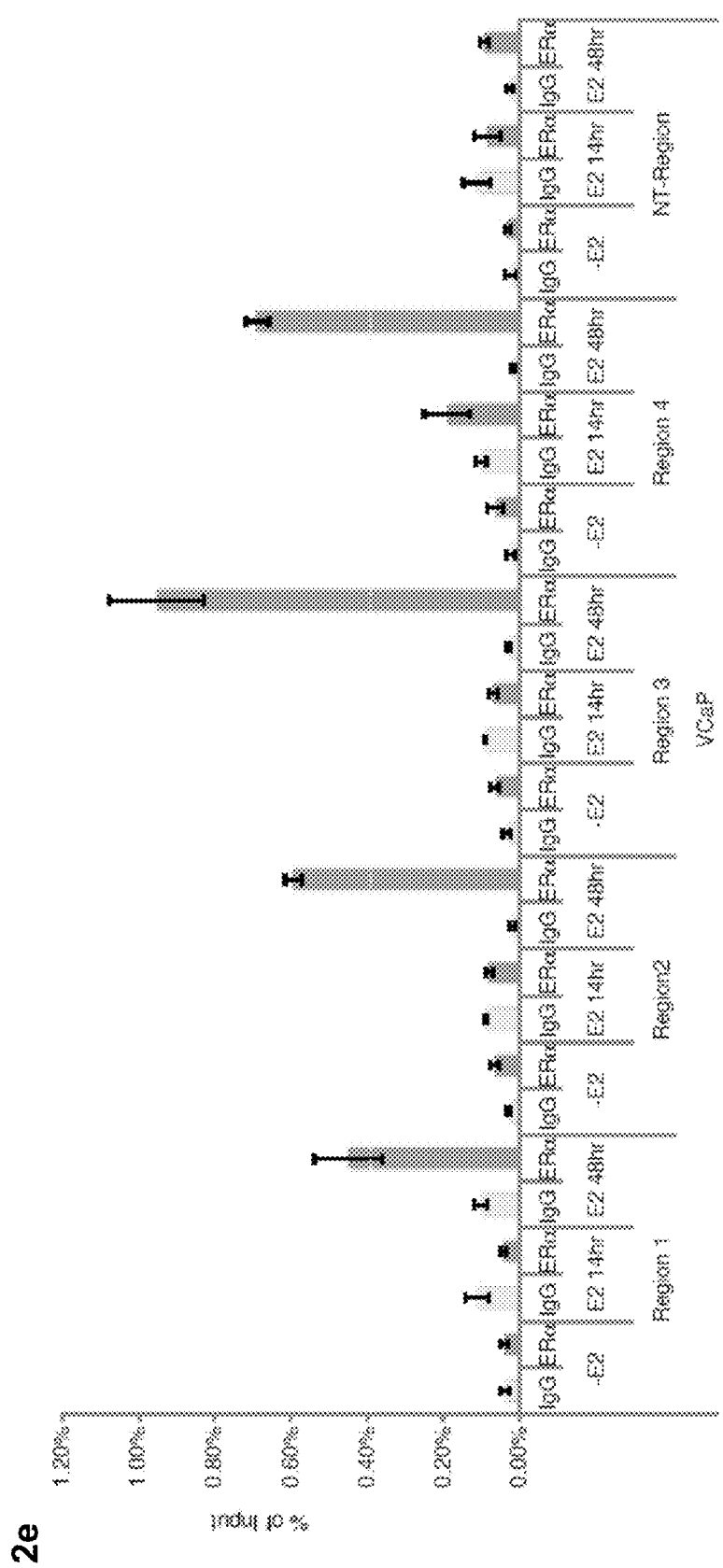
Figures 2F, 2G:
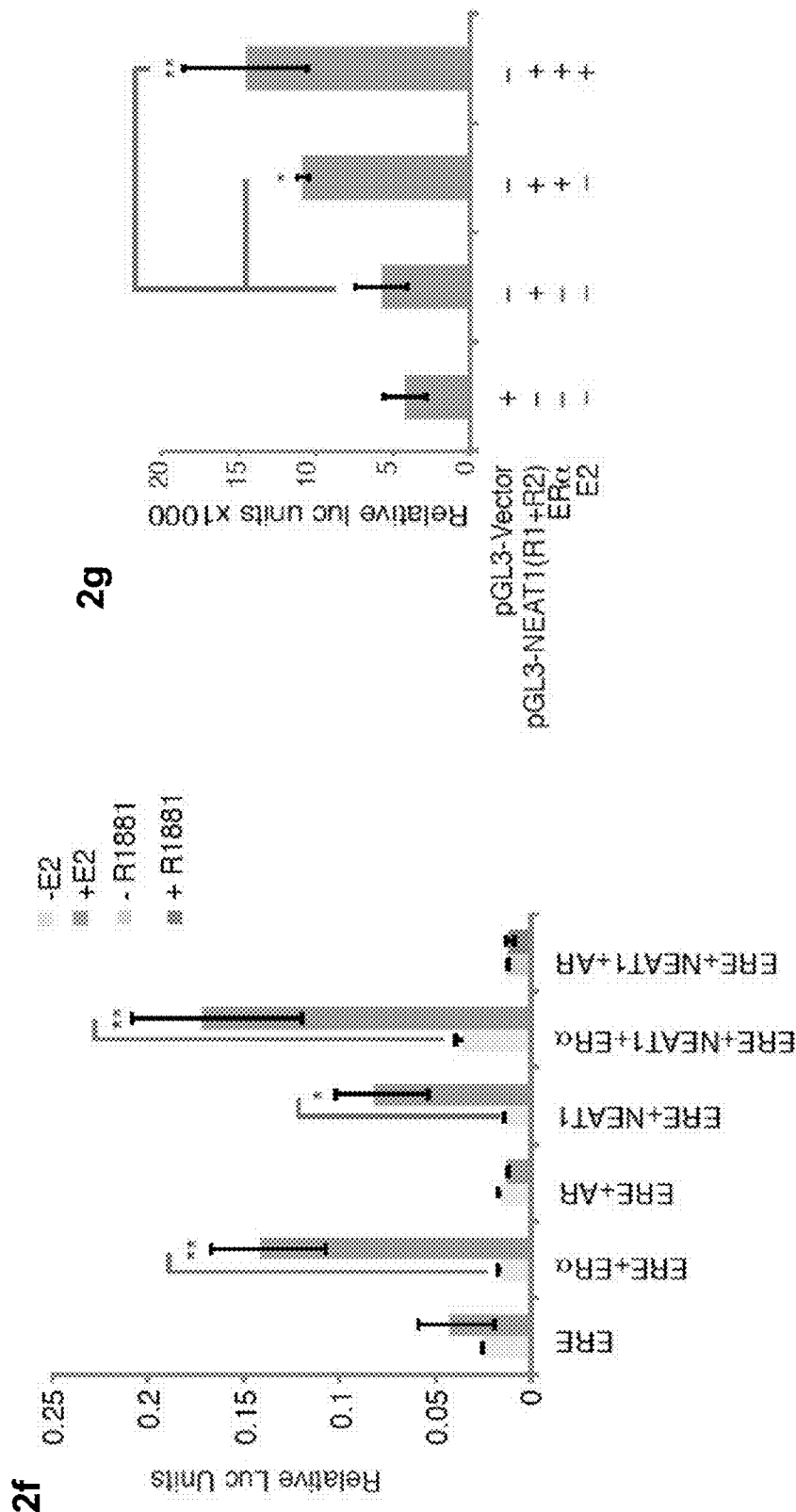

The inventors inspected our ERα ChIP-seq data in VCaP ERα and NCI-H660 cells and identified two ERα binding sites on the NEAT1 promoter (FIG. 2d). Analysis of chromatin marks using ChIP-seq data sets for histone marks (Yu (2010)) revealed the presence of active histone marks H3 Acetyl K9 and H3K4me3 in the promoter region of NEAT1, while H3K36Me3 marks were abundant in the gene body (FIG. 2d). A recent study revealed that bivalent H3K4Me3 and H3K36Me3 marks are indicators of functional transcriptional loci from the non-coding genome (Guttman (2009)). ERα recruitment to specific regions of the NEAT1 promoter was independently validated by ERα ChIP in VCaP, VCaP ERα and NCI-H660 cells (FIG. 2e) using specific primers encompassing ERα binding sites in the NEAT1 promoter. The inventors found that a functional estrogen/ERα signaling pathway was active in VCaP cells, as determined by reporter-based ERE luciferase assays in VCaP cells, with ERα and AR overexpression and E2 or R1881 treatment respectively for 48 h (FIG. 2f). To further test whether ERα is required for NEAT1 transcriptional activation, the inventors generated luciferase promoter reporter constructs with both ERα binding sites upstream of the luciferase-coding region. Luciferase reporter assays in VCaP cells confirmed that NEAT1 promoter activity was upregulated in an ERα-dependent manner and further enhanced with E2 treatment (FIG. 2g).

ERα and NEAT1 Regulate Several Prostate Cancer Genes

The inventors next sought to understand the physiological role of NEAT1 and to determine the downstream targets of the ERα-NEAT1 axis in prostate cancer. Transcriptome sequencing of VCaP and VCaP ERα cells and pairwise comparison revealed 588 genes to be upregulated in VCaP ERα cells (log 2 fold change >2). The inventors performed a comparative analysis of this 588-gene signature using Oncomine concept analysis. The inventors focused on datasets from prostate cancer studies that included both prostate tumor and benign prostate tissues. The analysis revealed that the ERα gene signature was significantly upregulated in a number of prostate cancer datasets, but was downregulated in other non-prostate datasets, indicating that ERα regulates prostate cancer-specific genes.

Figure 3A:
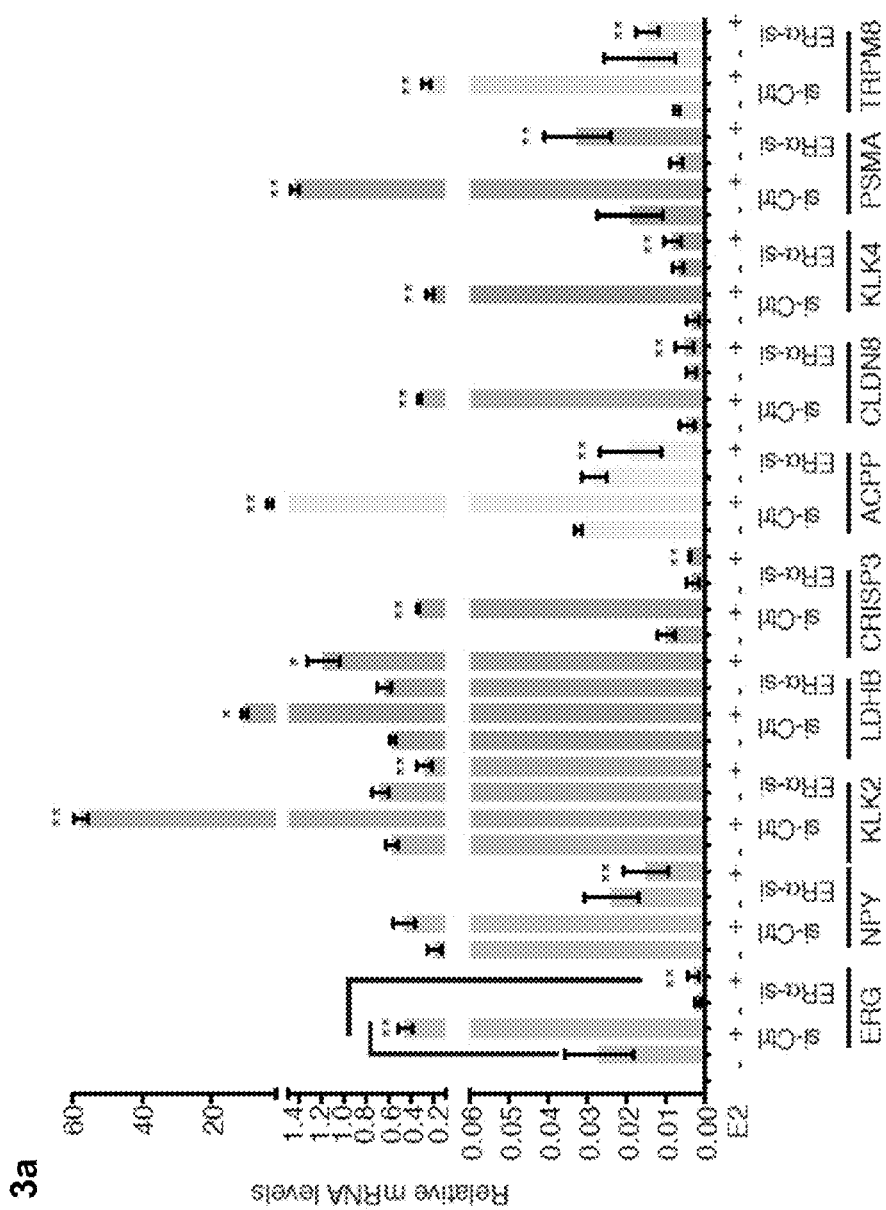
FIG. 3a-3b. NEAT1 ERα signature correlates with prostate cancer. (3a) qRT-PCR analysis of relative mRNA levels of ERα target genes in VCaP cells with knockout of ERα with and without E2 treatment. The target genes selected for validation are the ones that had the highest log 2 fold difference in VCaP and VCaP ERα cell lines. Results are expressed as the mean±s.d. calculated from three independent experiments. Student's t-test was performed (as indicated) for comparisons between −E2 and +E2 conditions for Ctrl siRNA and ERα-siRNA transfections and *p<0.05 and **p<0.01 was considered statistically significant. A representative example is shown for ERG target expression. (3b) qRT-PCR analysis of ERα target genes in VCaP cells with ERα overexpression and NEAT1 knockout with and without E2 treatment. Results are expressed as themean±s.d. calculated from three independent experiments. Error bars represent the range of data. Student's t-test was performed for comparisons between −E2 and +E2 conditions for scrambled siRNA and NEAT1 siRNA transfections in VCaP and VCaPERα cells and *p<0.05 and **p<0.01 was considered statistically significant. Vertical error bars represent the range of data. A representative example is shown for SPDEF target expression.

To validate if ERα targets identified by in silico analysis are dependent on cellular levels of ERα, the inventors experimentally silenced ERα in VCaP cells using an siRNA approach and determined transcript levels of 10 target genes using qRT-PCR. The target genes selected for validation were those genes that demonstrated the highest log 2 fold difference in VCaP and VCaP ERα cells. Results indicated that mRNA levels of the target genes selected were dependent on ERα (FIG. 3a), suggesting a distinct contribution of ERα in determining the transcriptional program.

NEAT1 is a Downstream Target in the Eα Signaling Pathway

Figure 3B:
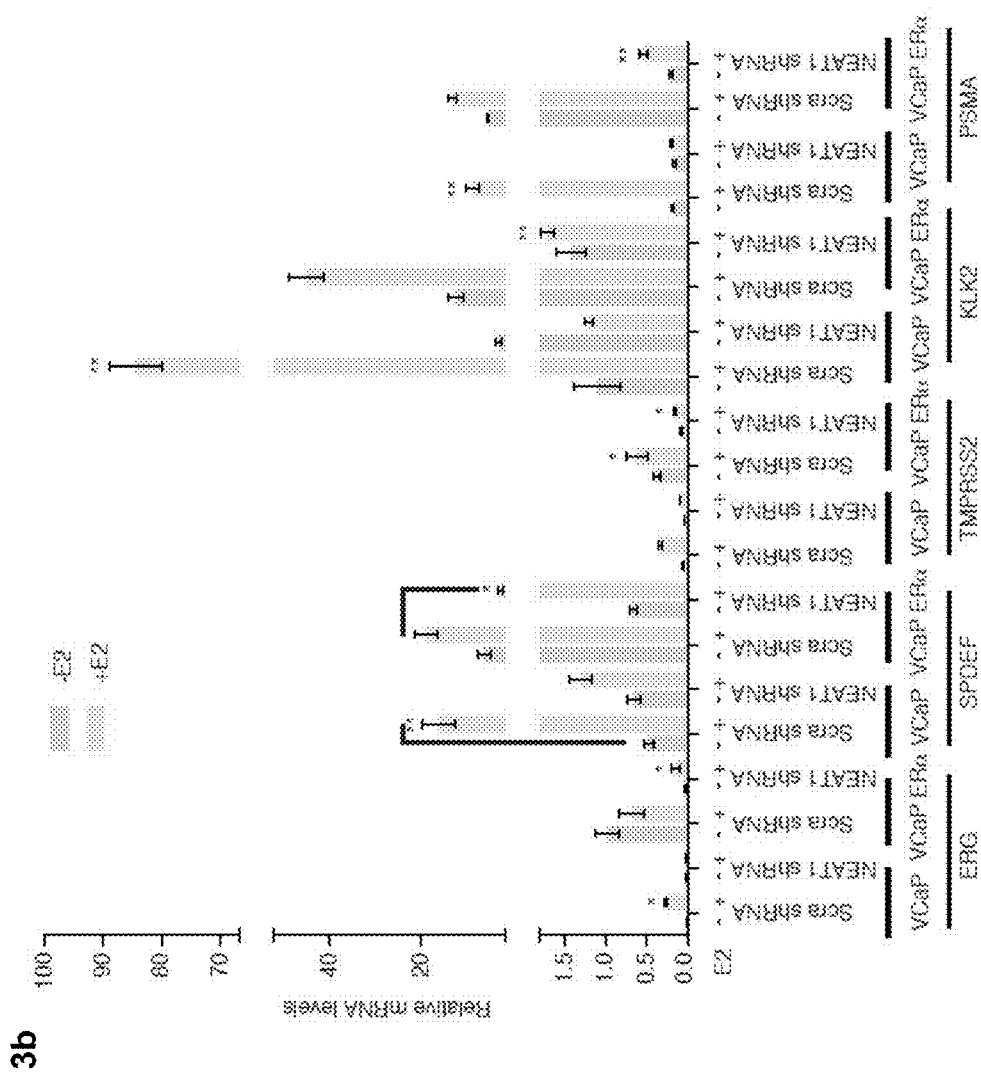

After determining an ERα signature, the inventors next investigated the potential role of NEAT1. Interestingly, knockout of NEAT1 compromised the expression of ERα target genes, suggesting that NEAT1 is not only a downstream target but also a mediator of ERα signaling in prostate cancer cells (FIG. 3b). To evaluate this further and to determine if a functional synergy between ERα and NEAT1 pathways exists in prostate cancer cells, the inventors performed RNA-seq of vector control and NEAT1-overexpressing VCaP cells to determine a NEAT1 signature. To achieve this, the inventors limited their analysis to genes that were upregulated four-fold in NEAT1-expressing cells. Interestingly NEAT1 signature showed a strong correlation with the ERα signature genes (q=1.90E-120). Analysis of the top 1000 genes of the NEAT1 signature revealed that this signature is upregulated in prostate cancer datasets when compared with other cancer datasets. Furthermore, NEAT1 signature was also upregulated in all prostate cancer datasets (comparing benign vs. PCa; odds ratio >2.0 and P<1×10$^{-6}$).

The inventors also queried Oncomine prostate datasets to identify genes whose mRNA levels correlate with those of NEAT1 (correlation coefficient >0.5). The inventors compared this gene list with the ERα signature genes from their analysis and identified 155 genes in common. These 155-gene were also found to be upregulated in all prostate cancer datasets compared with other cancer datasets (only normal vs. cancer datasets were considered; odds ratio >3.0 and P<1×10$^{-6}$).

Figure 4A:
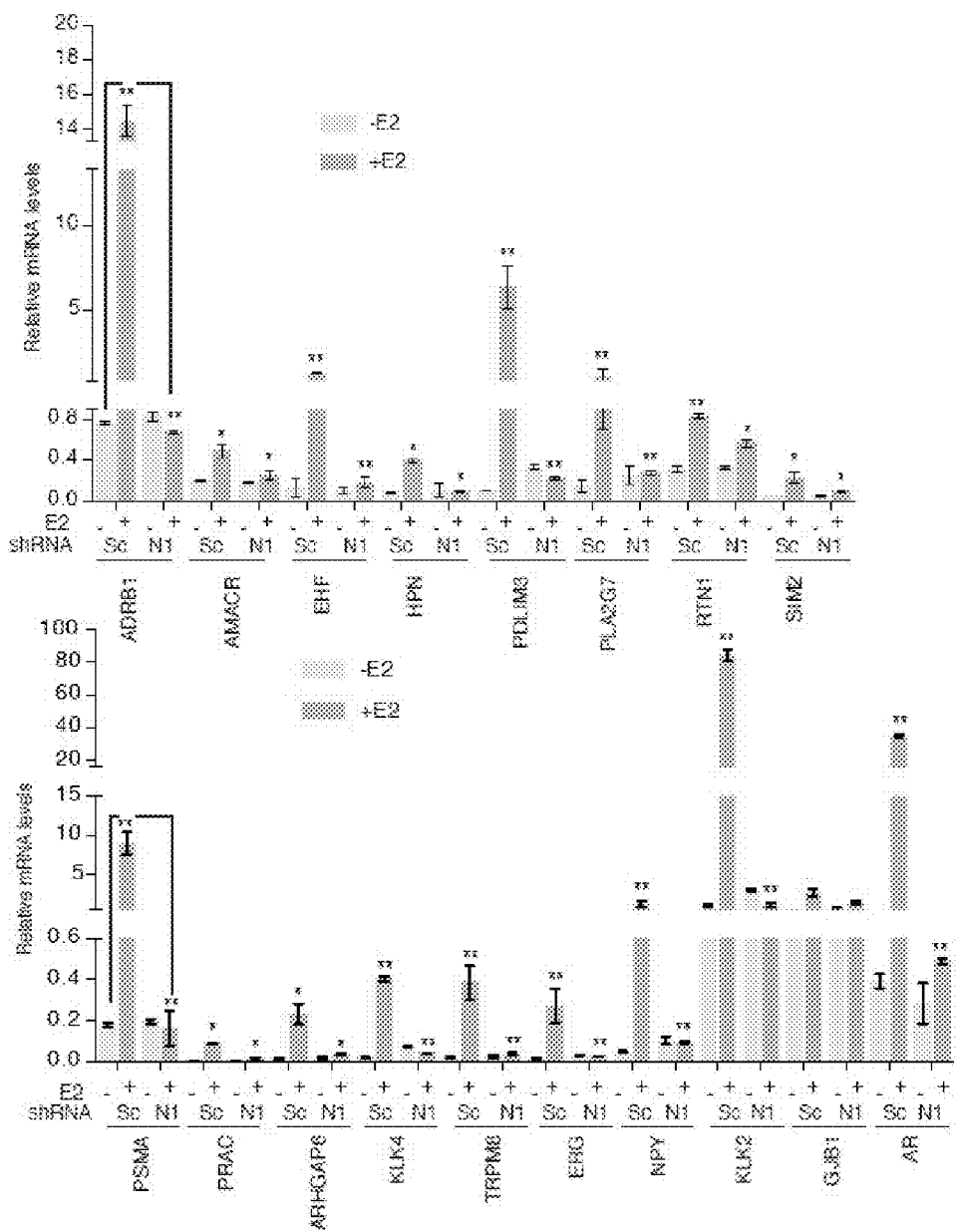
FIG. 4a-4b. NEAT1 ERα signature is upregulated in prostate cancer. (4a) Relative mRNA levels of genes, analyzed using qRT-PCR in parental VCaP cells transfected with scrambled (Sc) and NEAT1siRNA (N1), respectively, with and without E2 (10 nM) treatment. Results are expressed as the mean±s.d. calculated from three independent experiments. Error bars represent the range of data. Student's t-test was performed for comparisons (relative mRNA levels of target gene expression) between −E2 and +E2 conditions for scrambled siRNA and NEAT1 siRNA transfections. A representative example is shown for ADRB1 and PSMA target expression. *p<0.05 and **p<0.01 was considered statistically significant. (4b) Validation of expression of the top target NEAT1 ERα signature genes in a small matched patient cohort of 13 benign and 13 PCa, n=26. Results are expressed as the mean±s.d. of two independent experiments. Error bars represent the range of data.
Figure 4B:
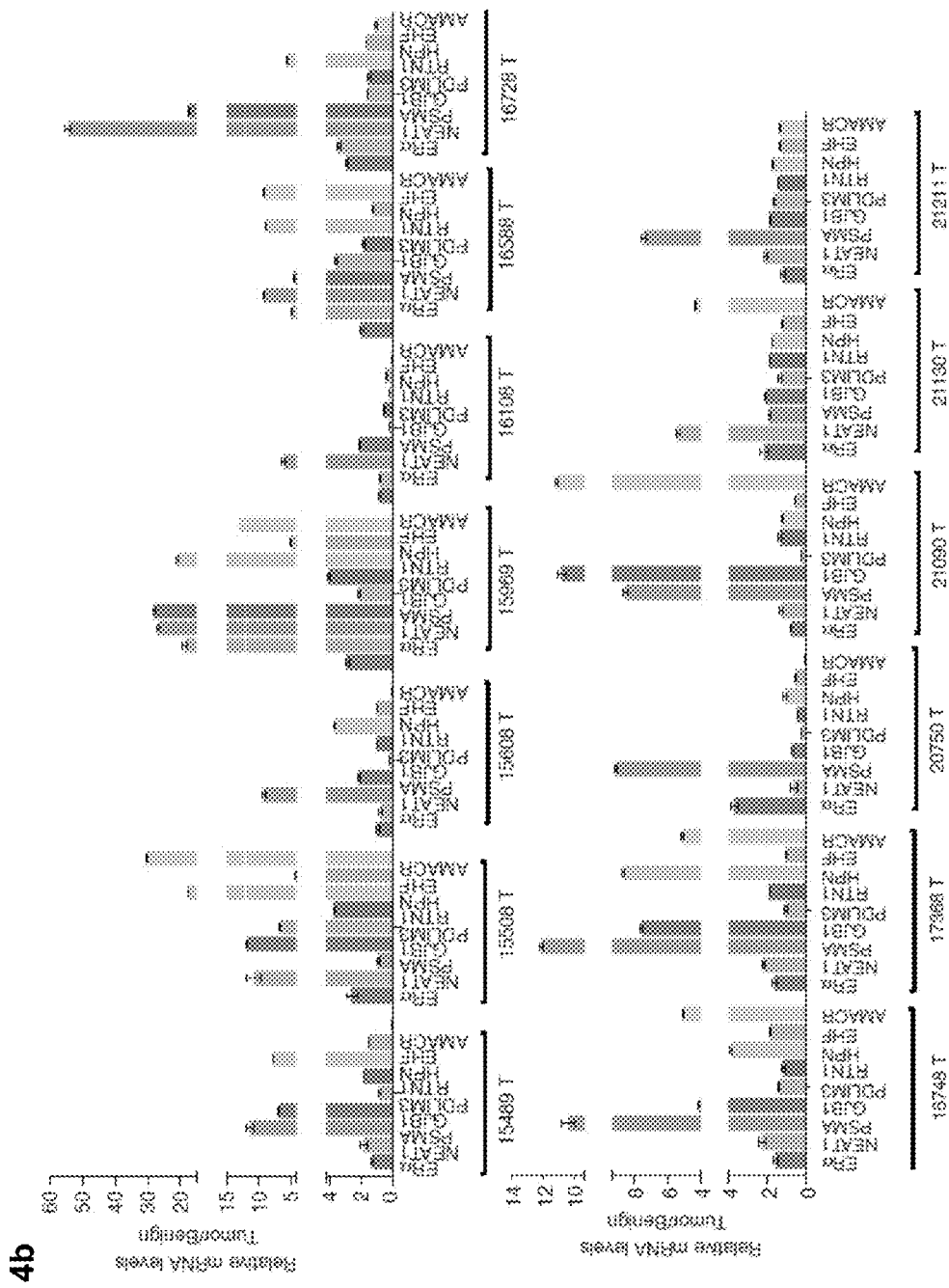

To determine if the genes identified by in silico analysis are indeed influenced by NEAT1, the inventors silenced NEAT1 in VCaP cells and determined transcript levels of potential target genes using qRT-PCR. The inventors selected the top 10 genes that were significantly correlated to NEAT1 expression across all prostate cancer concepts. As expected, mRNA levels of these selected target genes were indeed dependent on NEAT1, further confirming a definite role of NEAT1 in the transcriptional program (FIG. 4a). In addition to cell lines, the inventors also determined transcript levels of these ERα-NEAT1 signature-selected genes in a small patient cohort (n=26) of 13 matched benign and prostate adenocarcinoma, respectively. It was observed that relative mRNA levels of these NEAT1-ERα signature-selected genes revealed significant upregulation in prostate cancer (FIG. 4b). The inventors computed the log 2 fold change of expression levels using the 13 paired tumor/benign samples for NEAT1 and for these selected genes, then correlated the fold change values, and observed a moderate to strong correlation between NEAT1 and the associated genes in clinical samples. Among these seven genes, prostate-specific membrane antigen (PSMA) and alpha-methylacyl-CoA racemase (AMACR) are well-known diagnostic and, in the case of PSMA, prognostic markers of prostate cancer progression (Burger (2002); Gumulec (2012); Jiang (2013); Ross (2003); Xiao (2001)). Furthermore, knocking down ERβ did not alter expression of key signature genes in LnCaP, PC3, VCaP and NCI-H660 cells, suggesting a non-redundant regulatory role for ERα.

NEAT1 and Chromatin Regulation

Figures 5A, 5B, 5C:
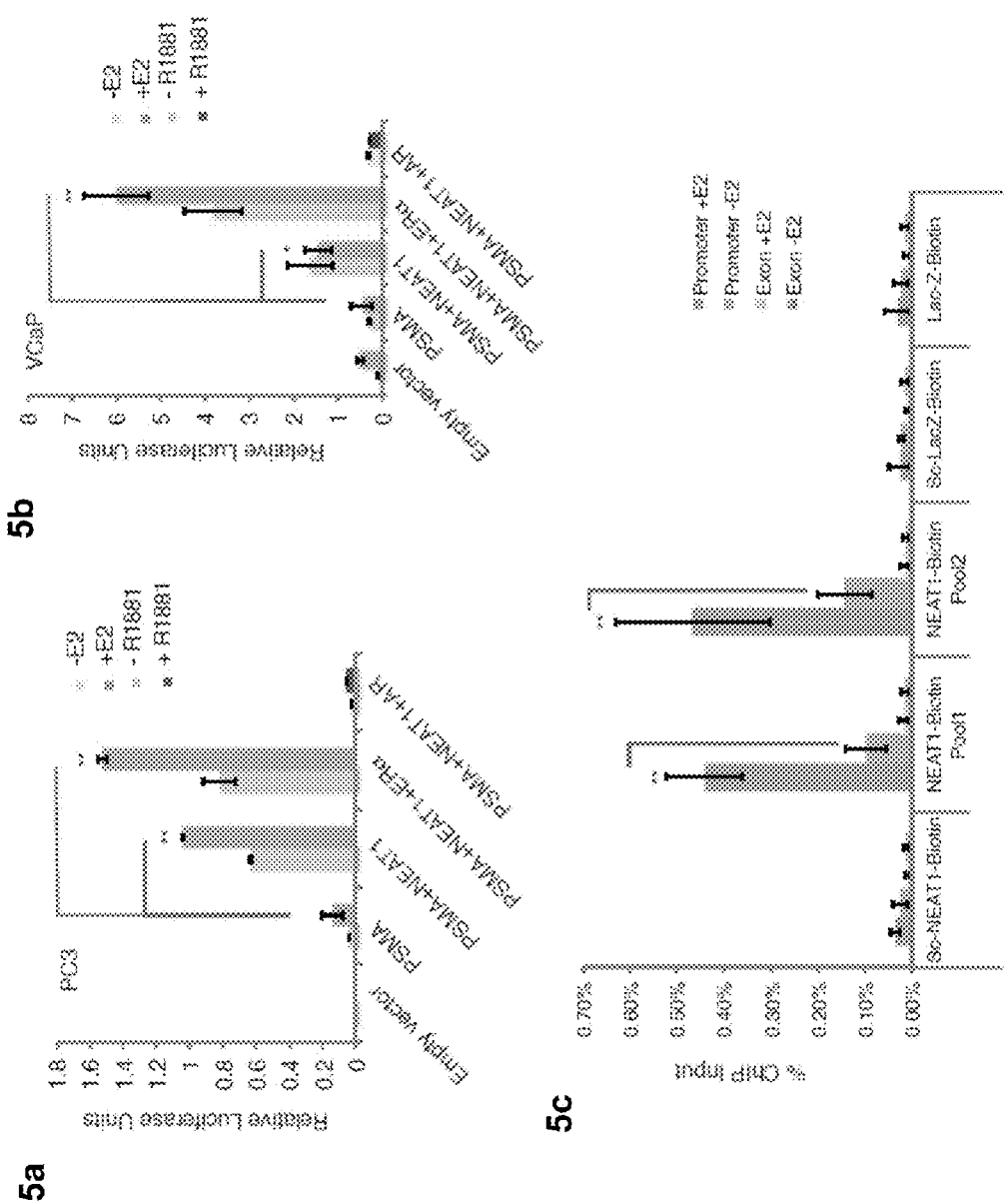
FIG. 5a-5d. NEAT1 is a transcriptional regulator. (5a& 5b) Promoter luciferase reporter assay shows that NEAT1 activates PSMA promoter in PC3 and VCaP cells. Cells were co transfected with empty vector or PSMA luc and Renilla-luc reporter genes alone or with NEAT1, NEAT1+ERα and NEAT1+AR. Luciferase activity was measured 48 h post treatment with E2 (10 nM) or R1881 (1M). Results are expressed as the mean±s.d. calculated from three independent experiments. Student's t-test was performed for comparisons (relative PSMA-luciferase activity) between −E2 and +E2 conditions for vector control, NEAT1 and NEAT1+ERα transfections in PC3 and VCaPcells. *p<0.05 and p<0.01 was considered statistically significant. (5c) Quantitative analysis of NEAT1 ChIRP in VCaP cells with or without E2 treatment (10 nM). Recruitment profiles of NEAT1 to PSMA are shown. Results are expressed as the means of percentage of input±s.d calculated from two independent experiments. Error bars represent the range of data. Results were reproducible between representative experiments. p<0.01 was considered statistically significant. (5d) Analysis of chromatin landscape at PSMA promoter was performed by ChIP using antibodies IgG, H3K4Me3, H3K9Me3, H3K27Me3, H3AcK9, and ERα in VCaP cells alone or transected with NEAT1, ERα, NEAT1 ERα, NEAT1 ERα NEAT1_1 siRNA, NEAT1 ERα NEAT1_2 siRNA with and without E2 treatment. qPCR was performed with specific primers for the PSMA promoter. Results are expressed as the means of percentage of input±s.d. calculated from two independent experiments. Error bars represent the range of data. Results were reproducible between representative experiments.
Figure 5D:

To study the potential role of NEAT1 in regulation of target genes in vivo, the inventors performed luciferase reporter assays using PSMA-luc as a candidate NEAT1 target. NEAT1 induced robust activation of the PSMA promoter in PC3 cells (FIG. 5a) and VCaP cells (FIG. 5b). These results prompted us to investigate if NEAT1 is recruited to chromatin of target genes. The inventors used the ChIRP approach to pull down endogenous NEAT1 from VCaP cells. Analysis of the ChIRP data revealed that NEAT1 is recruited to the PSMA promoter, but not the downstream exon 1 (FIG. 5c). In addition to PSMA, the inventors also tested NEAT1 recruitment to other target genes described in FIG. 3a and FIG. 4a and observed that in addition to PSMA, NEAT1 was also recruited to the promoter region of GJB1. This suggests that NEAT1 transcriptionally regulates a compendium of genes known to be involved in prostate cancer progression. The inventors hypothesized that NEAT1 might contribute to gene transcription by interacting with chromatin-modifying proteins and/or interacting with histones. The inventors next analyzed the chromatin landscape at the PSMA promoter and observed that NEAT1_1, and not NEAT1_2, facilitated gene transcription by promoting an active chromatin state (FIG. 5d). Overexpression of NEAT1_1 significantly increased active chromatin marks at the PSMA promoter (i.e., H3K4Me3 and H3AcK9). Of note, ERα was not significantly recruited to the PSMA promoter when expressed alone. Overexpression of NEAT1_1 resulted in subsequent recruitment of NEAT1_1 and ERα to the PSMA promoter. These studies indicate that while NEAT1_1 may function as a chaperone for ERα and other chromatin-modifying machinery to target promoters, binding of ERα and/or recruitment to NEAT1_1 targets is not necessary for transcriptional activation.

As the inventors data suggest that NEAT1 overexpression favors a chromatin landscape for active transcription, the inventors investigated whether NEAT1 could directly interact with nucleosomal histones. Nuclear lysates from VCaP cells were used in an immunoprecipitation experiment with streptavidin-beads coupled with either scrambled, antisense NEAT1, or antisense NR_024490 (another ERα lncRNA target) oligonucleotides. NEAT1 was found to specifically associate with histone H3 and the specificity of this binding is apparent when comparing Streptatividin-IP using scrambled biotinylated oligos and Streptavidin-IP using antisense-NEAT1 oligos and nuclear lysates from NEAT1 siRNA treated cells, respectively. As an additional negative control, the inventors used scrambled and specific antisense oligos for a different lncRNA, NR_024490, another ERα target. The results indicate that NEAT1 can associate with chromatin via specific interaction with histone H3. The inventors also determined association of NEAT1 with active histone H3 modifications, including H3AcK9 and H3K4Me3. Similar association patterns were seen for NEAT1 in NCI-H660 cells.

To complement this finding, the inventors performed RNA immunoprecipitation from VCaP ERα cells using anti-histone H3 and anti SNRNP70 (positive control) as the immunoprecipitating antibody. qRT-PCR showed robust binding of NEAT1 to histone H3. The positive control U1 snRNA showed high enrichment in the immunoprecipitate with SNRNP70. To further confirm the specificity of NEAT1 binding to histone H3, the inventors performed a streptavidin-biotin pull down assay in VCaP and VCaP ERα cells with and without E2. These data suggest that NEAT1 can directly interact with the histone H3 component of chromatin.

NEAT1 Promotes Prostate Tumorigenesis

Figures 6A, 6B, 6C:
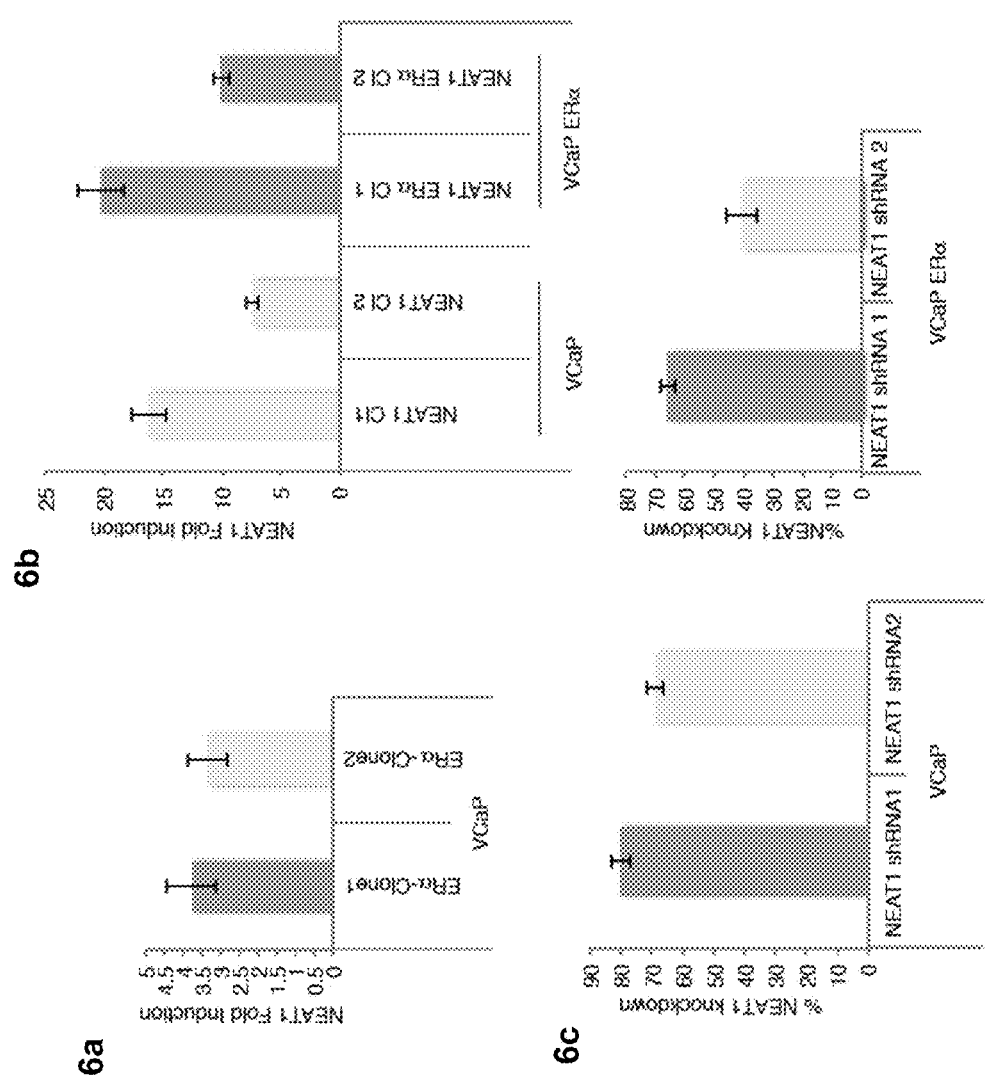
FIG. 6a-6l. NEAT1 is a driver of oncogenic cascade. (6a) NEAT1 fold induction in VCaP cells overexpressing ERα. (6b) NEAT1 fold induction in VCaP and VCaP ERα cells overexpressing NEAT1. (6c) % knockdown of NEAT1 in VCaP and VCaP ERα cells expressing scrambled siRNA and NEAT1 siRNA. Mean±s.d calculated from three independent experiments is shown. Results were reproducible between representative experiments. (6d) Cell proliferation assays were performed in VCaP vector control, NEAT1 overexpressing cells and also in si scrambled and NEAT1 knockout cells with or without E2 treatment (10 nM) at 24 h and 48 h time points. Results are expressed as the mean±s.d. calculated from three independent experiments. Student's t-test was performed for comparisons (relative cell proliferation) between E2 conditions for vector control, NEAT1 Cl-1 and NEAT1 Cl-2 and E2 conditions for si-scrambled, Neat1-siRNA1 and siRNA2 transfections. **p<0.01 was considered statistically significant. (6e) Quantitative bar chart for depicting percentage cell invaded at the completion of invasion assay performed in VCaP vector control, NEAT1 overexpressing cells and also in si scrambled and NEAT1 knockout cells with or without E2 treatment (10 nM). Results are expressed as the mean±s.d. of three independent experiments. *p<0.05 and p<0.01, Student's t-test. (6f Soft agar assays were performed with VCaP control and NEAT1 expressing cells. Quantitative bar-plot analysis of stained colonies at 21 days is shown. Results are expressed as the mean±s.d. of three independent experiments. *p<0.001, Student's t-test. (6g) Colony forming assay were performed in VCaP vector control, NEAT1 overexpressing cells with or without E2 treatment (10 nM). Right panel depicts the number of colonies at 21 days. Results are expressed as the mean±s.d. calculated from three independent experiments. *p<0.05 and **p<0.01, Student's t-test. (6h) Growth curve for the tumors monitored up to 45 days. Results are expressed as the mean±s.d. calculated from three independent experiments. *p<0.05, Student's t-test. (6i & 6j) VCaP and NCI-H660 vector control and NEAT1 overexpressing cells were injected s/c into the flank of male NOD-SCID mouse. Bioluminescence imaging monitored the tumor growth. Growth curve for the tumors monitored up to 45 days is shown, VCaP (6i) and NCI-H660 (6j). (6k) The average tumor weight is shown. Mean±s.d is shown, p<0.01, Student's t-test. (6l) Representative immunohistochemistry on the formalin fixed paraffin embedded tissues for ERα. The lower panel shows the H&E staining for the tumors and on the right we see qRT-PCR data for expression of NEAT1 in the xenografts. Data is presented as mean±s.d from a representative experiment performed in triplicate (n=3), p<0.01. (6m) The average weight of tumors from VCaP vector con and NEAT1 expressing group (top panel) and from NCI-H660 vector con and NEAT1 expressing group (bottom panel). Results are expressed as the means±s.d. of three independent experiments. Statistical analysis was performed using Student's t-test and **p≤0.01.
Figures 6D, 6E, 6F:
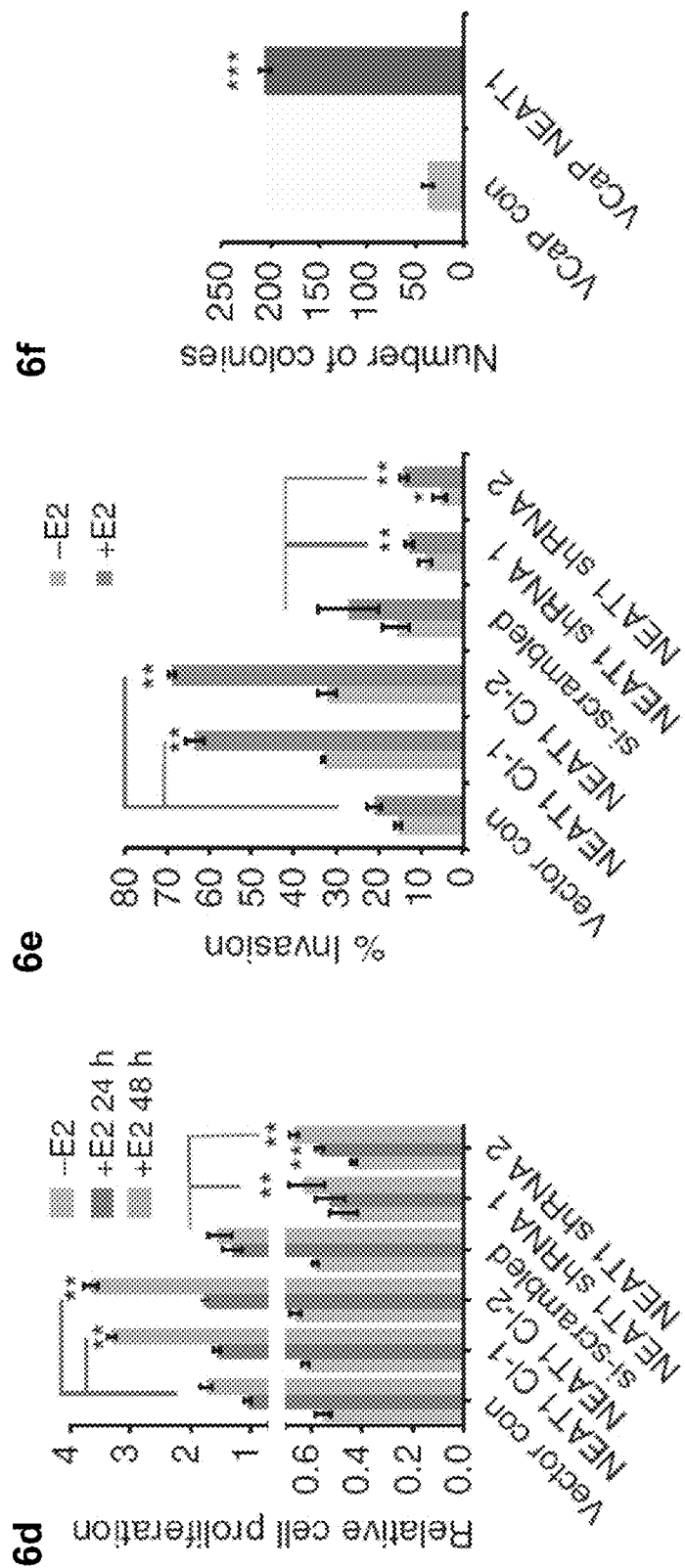

To better understand the physiological role of NEAT1 in context of ERα in prostate cancer, the inventors first determined levels of NEAT1 in VCaP cells overexpressing ERα (FIG. 6a). Further, the inventors generated stable VCaP and VCaP ERα cell lines that overexpress NEAT1 (FIG. 6b). The inventors also knocked down NEAT1 in VCaP and VCaP ERα-expressing cells by stably expressing NEAT1 siRNA targeting different regions of NEAT1 and non-targeting siRNA (Table 2 and FIG. 6c). While overexpression of NEAT1 significantly increased proliferation and cell invasion, knockdown of NEAT1 significantly decreased proliferation and the invasive properties of the cells (FIGS. 6d & 6e).

Figures 6G, 6H, 6I, 6J:
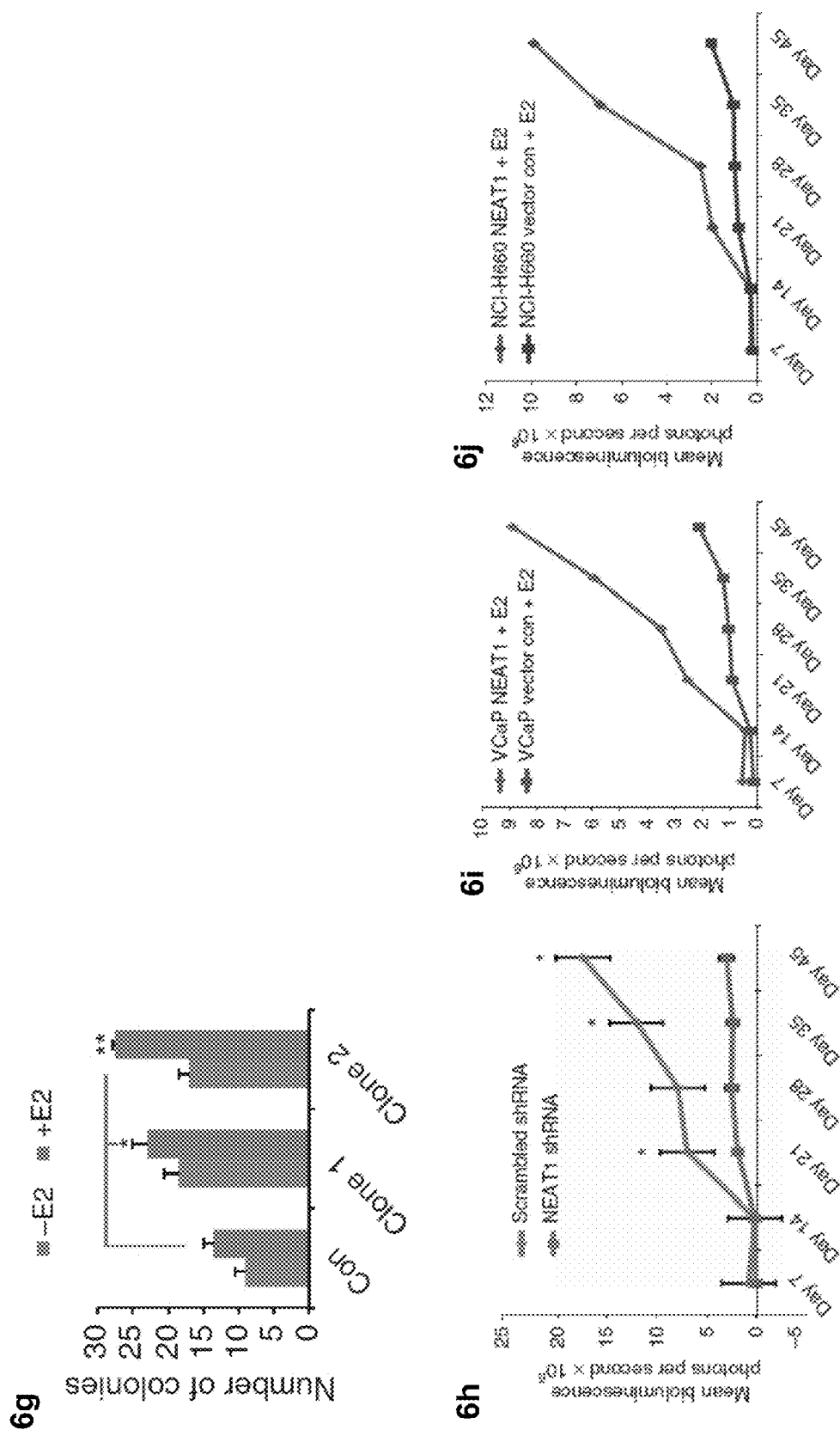

Soft agar assays were performed in both VCaP and VCaP NEAT1 cells. Colonies were monitored over a period of 21 days. Overexpression of NEAT1 resulted in a significantly higher number of viable colonies (FIG. 6f). Colony-forming assays performed in NEAT1 clones in VCaP cells with and without E2 demonstrated that E2 treatment in NEAT1-overexpressing cells significantly increased the number of colonies (FIG. 6g). These in vitro assays establish an oncogenic role for NEAT1.

Figures 6K, 6L, 6M:
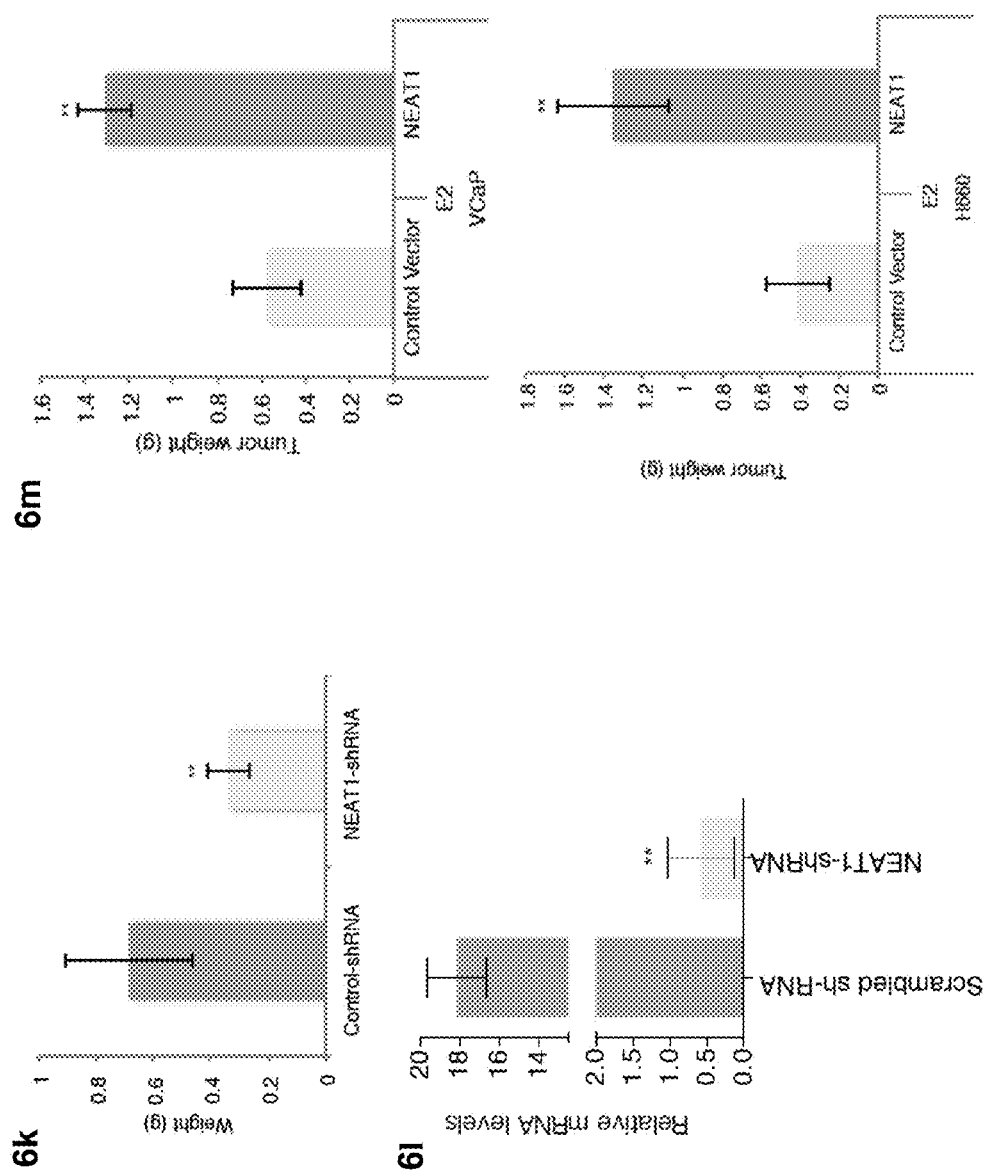

To further validate the oncogenic role of NEAT1, the inventors extended their studies to an in vivo model system. The inventors performed xenograft studies in NOD-SCID mice. The mice were treated with time-release estrogen pellets. They were divided into two groups: one group was implanted subcutaneously with VCaP ERα cells expressing control siRNA and luciferase reporter, and the other group with VCaP ERα cells expressing NEAT1 siRNA luciferase reporter. The tumor growth was monitored weekly for 45 days and was found to be significantly lower in the NEAT1 siRNA-expressing group compared with the control group (FIG. 6h). The tumors were excised and weighed and the NEAT1 siRNA group had significantly smaller tumors (FIG. 6k). The inventors confirmed the efficacy of the siRNA in vivo by measuring the NEAT1 and ERα levels in the tumors (FIG. 6l).

To further substantiate the hypothesis that NEAT1 plays a role in tumorigenesis, the inventors repeated the experiment in athymic nude mice using VCaP control and VCaP NEAT1-overexpressing cells as well as NCI-H660 and NCI-H660 NEAT1-overexpressing cells. In both these experiments, a significantly higher tumor growth was seen in the NEAT1-overexpressing cells (FIGS. 6i & 6j, FIG. 6m) further confirming its oncogenic potential. qRT-PCR analysis confirmed an increased expression of the NEAT1 signature genes in VCaP NEAT1 xenografts compared with control VCaP xenograft tissue.

NEAT1 is Associated with Therapeutic Resistance

Studies presented so far show that ERα establishes an oncogenic cascade and that NEAT1 functions as a downstream mediator of ERα signaling. The ERα-NEAT1 axis is functional both in AR-positive and -negative cell lines and drives prostate carcinogenesis. The inventors hypothesized that targeting NEAT1 using mechanisms that can constrain ERα might represent a novel therapeutic strategy in prostate tumors that are resistant to anti-androgen therapy. To test this hypothesis in vitro, the inventors evaluated the effect of anti-estrogens and anti-androgens on NEAT1 levels in prostate cancer cell lines. As shown in FIG. 7a & b, NEAT1 expression was constrained when cells were treated with the ERα antagonists ICI 182,720 (ICI) and 4-hydroxy tamoxifen (4OHT) in combination with E2. Intriguingly, treatment of ICI and 4OHT alone for longer periods can enhance NEAT1 expression (FIGS. 7a & b). The inventors observed similar results with AR antagonists enzalutamide and bicalutamide (FIGS. 7c & d). These results provide compelling evidence to evaluate NEAT1 levels in advanced CRPC cases. RNA-FISH analysis of benign and advanced prostate tumors, including CRPC and NEPC tumor tissue samples illustrated significantly upregulated NEAT1 levels in advanced prostate cancer (FIG. 7e), with enhanced focal staining throughout the tumor tissue. The inventors also screened 9 cases of benign prostate, 7 PCa, and 7 CRPC for NEAT1 and ERα expression by qPCR (FIG. 7f), and both NEAT1 and ERα levels were significantly higher in the CRPCs. The inventors determined the correlation between NEAT1 and ERα expression by estimating the Pearson's correlation coefficient R. The results indicate a strong positive correlation: R=0.86 (p-value=1.9e-07). Taken together, our results present a novel role for the non-coding transcriptome in cancer-favorable adaptations.

NEAT1 is Associated with Aggressive Prostate Cancer

Given the importance of NEAT1 in promoting tumorigenesis both in vitro and in vivo, the inventors sought to determine the relationship between NEAT1 levels and prostate cancer clinical outcomes in 594 patients from two radical prostatectomy cohorts with long-term clinical follow-up from the Mayo Clinic (Erho (2013); Karnes (2013)). Table 1 contains the patient characteristics of men who underwent radical prostatectomy at the Mayo Clinic Comprehensive Cancer Center between 1987 and 2001 for clinically localized prostate cancer.

The inventors assessed the prognostic potential of NEAT1 expression using several statistical measures and correlating it with biochemical recurrence (BCR) and metastasis (MET), prostate cancer-specific mortality (PCSM) and Gleason score (GS)>7. Biochemical recurrence was typically determined based on evaluating levels (e.g., protein levels in the blood or other body fluid) of biomarkers characteristic of prostate cancer (e.g., such as PSA). In order to evaluate endpoints of disease aggressiveness and progression based on NEAT1 expression, Kaplan-Meier (KM) analysis was performed for the BCR and MET endpoints. The resulting KM curves (FIGS. 8a & b) demonstrate that patients with higher NEAT1 expression have significantly worse outcomes for both BCR (p-value: 0.028) and MET events (p-value: 0.016).

Patient risk discrimination based on the expression profile of NEAT1 was assessed by area under the receiver operating characteristic curve (AUC) with 95% confidence intervals (CI) (FIG. 8c-8j). NEAT1 significantly segregates patients who exhibited BCR, MET, PCSM and GS>7.

To further compare NEAT1's prognostic ability to other clinicopathologic variables, univariable odds ratios were computed for the BCR, MET, PCSM, and GS>7 endpoints (FIG. 9a-d). NEAT1 was significantly prognostic for segregating high-risk from low-risk patients for each of the endpoints (p<0.05). Further multivariate analysis adjusting for adjuvant radiation and hormone treatment, in addition to the other clinicopathological variables assessed, also demonstrates that NEAT1 was significantly prognostic for BCR, MET, and GS>7, supporting NEAT1 as a prognostic biomarker for aggressive prostate cancer independent of common clinical and pathologic variables (FIG. 9e-9m). Overall, these results show that NEAT1 is significantly prognostic for several clinically relevant endpoints.

SUMMARY OF THE RESULTS

Analysis of global ERα recruitment in prostate cancer cells using a ChIP-seq approach revealed that ERα is preferentially recruited to intergenic regions of the prostate genome. Comparison of binding profiles with transcriptome sequencing data suggested that ERα drives expression of non-coding transcripts. From a large compendium of ERα-regulated non coding transcripts, NEAT1 was selected for a detailed biochemical and in vivo evaluation, based on an in silico approach that demonstrated a strong association of NEAT1 with prostate cancer progression. It has been shown here that ERα transcriptionally regulates NEAT1. NEAT1 is recruited to the promoter of several key target genes and induces an active chromatin state favorable for transcription. These studies indicate that ERα does not function as a molecular chaperone to guide NEAT1 to target chromatin; rather, it is believed that a complex proteome of chromatin-interacting proteins interacts with and guides NEAT1 to promoter targets. Interestingly, both ERα and NEAT1 signaling were refractory to AR inhibitors and the lack of AR or ERβ, thus indicating a functional specialization of the ERα-NEAT1 axis for prostate cancer progression. Furthermore, introduction of cells overexpressing NEAT1 could clearly induce prostate cancer progression in experimental animal models.

It has been shown here that NEAT1 regulates expression of prostate cancer genes by altering the epigenetic landscape at target gene promoters to favor transcription. A closer examination of NEAT1 revealed a previously uncharacterized role in recognition of modified histones. NEAT1 expression independently was sufficient to activate prostate cancer genes in an AR independent manner. Further, the results confirmed an oncogenic role for NEAT1 in an experimental animal model of prostate cancer and in cell culture models.

The identification of an ERα-NEAT1 axis herein illustrates a mechanism whereby prostate cancer cells may develop therapeutic resistance through positive selection of an alternate nuclear receptor signaling pathway in the absence of AR or during androgen ablation therapy. From a clinical perspective, the results herein indicate for the first time that NEAT1 is significantly prognostic for several clinically relevant endpoints. In prostatectomy specimens from two large cohorts, high NEAT1 expression was associated with a significant increase in both biochemical and metastatic recurrence rates compared to those with low NEAT1 expression.

In summary, the studies herein provide important insights into a unique mechanism of ERα regulation in prostate cancer and identifies NEAT1 as a novel prognostic marker and potential therapeutic target in this disease. While the studies have identified a previously unexplored function of ERα in regulating lncRNAs, it is also the first of its kind to demonstrate transcriptional regulation of lncRNAs by an alternative steroid receptor in prostate cancer. It is believed that NEAT1 is directly involved in modulation of the phenotype of a leading disease. Combinatorial targeting of NEAT1 and AR may represent a unique therapeutic regimen within a subset of patients with advanced prostate cancer.

TABLE 1

Patient characteristics for the pooled Mayo nested case-control and Mayo case-cohort datasets

|  | % |
|---|---|
| BCR | 68 |
| MET | 41 |
| PCSM | 25 |
| GS > 7 | 50 |
| pT3+ | 68 |
| LNI | 18 |
| SMS | 62 |
| SVI | 42 |
| ECE | 53 |
| pPSA > 20 | 29 |
| AdjHTx | 33 |
| AdjRTx | 12 |

Biochemical recurrence (BCR), metastatic recurrence (MET), prostate cancer specific mortality (PCSM), Gleason score (GS) > 7, pathological tumor stage 3 or greater (pT3+), Lymph Node Invasion (LNI), Surgical Margin Status (SMS) positive, Seminal Vesicle Invasion (SVI), Extra Capsular Extension (ECE), preoperative PSA (pPSA), adjuvant hormone therapy, and adjuvant radiation therapy are shown.

TABLE 2

Sequences of siRNAs

| Target | Seq. |
|---|---|
| siNEAT1 Sense | UGGUAAUGGUGGAGGAAGAUU (SEQ ID NO: 3) |
| siNEAT1 Sense | GUGAGAAGUUGCUUAGAAAUU (SEQ ID NO: 4) |
| siNEAT1 Sense | GGAGGAGUCAGGAGGAAUAUU (SEQ ID NO: 5) |
| siNEAT1_2 Sense | CCAAAUAGGCUUACAGAUAUU (SEQ ID NO: 6) |
| siNEAT1_2 Sense | AGAGAGAAGUUGUGGAGAAUU (SEQ ID NO: 7) |
| Sense | GCCUUUACUACAUGUGUGA (SEQ ID NO: 43) |
| Antisense | UCACACAUGUAGUAAAGGC (SEQ ID NO: 44) |
| Sense | CUUAGAACUUUAAGUGCAA (SEQ ID NO: 45) |
| Antisense | UUGCACUUAAAGUUCUAAG (SEQ ID NO: 46) | piLenti-NEAT1 siRNA-GFP 4 siRNAs targeting NEAT1:
NEAT1-1140:
Sense         TCATGGACCGTGGTTTGTTACTATAGTGT (SEQ ID NO: 8)
Antisense     3' AGTACCTGGCACCAAACAATGATATCACA 5' (SEQ ID NO: 47)

NEAT1-1732:
Sense         GTTCTTAGCCTGATGAAATAACTTGGGGC (SEQ ID NO: 9)
Antisense     3' CAAGAATCGGACTACTTTATTGAACCCCG 5' (SEQ ID NO: 48)

NEAT1-2352
Sense         GTGAGAAGTTGCTTAGAAACTTTCC (SEQ ID NO: 10)
Antisense     3' CACTCTTCAACGAATCTTTGAAAGG 5' (SEQ ID NO: 49)

NEAT1-3260
Sense         CTGGTATGTTGCTCTGTATGGTAAG (SEQ ID NO: 11)
Antisense     3' GACCATACAACGAGACATACCATTC 5' (SEQ ID NO: 50)

iLenti-si-scrambled CAACCCGCTCCAAGGAATCG (SEQ ID NO: 12)

TABLE 3

Primer sequences used in the Examples section

| Gene | Sequence (5'→3') | |
|---|---|---|
| NEAT1_2 F: | 5'-TTTGTGCTTGGAACCTTGCT-3' | (SEQ ID NO: 13) |
| NEAT1_2 R: | 5'-TCAACGCCCCAAGTTATTTC-3' | (SEQ ID NO: 14) |
| NEAT1v2 F: | 5'-TCTCCATTTCCCCATCTGAG-3' | (SEQ ID NO: 15) |
| NEAT1v2 R: | 5'-CAGCCACAGAAAAGGGAGAG-3' | (SEQ ID NO: 16) |

Primers used in ChIP Assay

| | | |
|---|---|---|
| NEAT1_P_2 F: | 5'-GGCAGTGACCCTGACAAGTT-3' | (SEQ ID NO: 17) |
| NEAT1_P_2 R: | 5'-TCTGAAGGAGCCTTTTCTGC-3' | (SEQ ID NO: 18) |
| NEAT1_P_3 F: | 5'-CCATCTGACCTTGGCACTTT-3' | (SEQ ID NO: 19) |
| NEAT1_P_3 R: | 5'-CAACCCACCTTGGTCTGACT-3' | (SEQ ID NO: 20) |
| NEAT1_P_4 F: | 5'-GGGAACTCCCTTCCTCAGTC-3' | (SEQ ID NO: 21) |
| NEAT1_P_4 R: | 5'-CAGCCTCCTGACCACAACTC-3' | (SEQ ID NO: 22) |
| NEAT1_P_1 F: | 5'-AATTTTCCAGATGTCCTGCC-3' | (SEQ ID NO: 23) |
| NEAT1_P_1 R: | 5'-AACAGTGCTTTTTGGGATCG-3' | (SEQ ID NO: 24) |
| ER_P_NT-NEAT1_1 F: | 5'-TCATTGGTCATGGCTTAGCA-3' | (SEQ ID NO: 25) |
| ER_P_NT-NEAT1_1 R: | 5'-AGCCATTTTGTCTCCTGCAC-3' | (SEQ ID NO: 26) |
| ER_P_NT-NEAT1_2 F: | 5'-ACTATTTCAACCGCCACGAG-3' | (SEQ ID NO: 27) |
| ER_P_NT-NEAT1_2 R: | 5'-TGCCTGAGGGCTCTAGTCAT-3' | (SEQ ID NO: 28) |

TABLE 4

Biotin TEG antisense probes

| Sequence Name | Sequence (5'-3') | |
|---|---|---|
| NEAT1_scr1 | gagaacatcgaattagcgtc | (SEQ ID NO: 29) |
| NEAT1_scr2 | gactatcagacgcctaagat | (SEQ ID NO: 30) |
| NEAT1_scr3 | ggtacgtaacgaggaagcga | (SEQ ID NO: 31) |
| NEAT1_185 | tgcggatattttccatgcag | (SEQ ID NO: 32) |
| NEAT1_488 | agcccttggtctggaaaaaa | (SEQ ID NO: 33) |
| NEAT1_800 | aagcgttggtcaatgttgtc | (SEQ ID NO: 34) |
| NEAT1_1161 | tcgccatgaggaacactata | (SEQ ID NO: 35) |
| NEAT1_1516 | tgcagcatctgaaaaccttt | (SEQ ID NO: 36) |
| NEAT1_1829 | cacaacacaatgacaccctt | (SEQ ID NO: 37) |
| NEAT1_2195 | actgtatctctaaccaaccc | (SEQ ID NO: 38) |
| NEAT1_2555 | ccaggaggaagctggtaaag | (SEQ ID NO: 39) |
| NEAT1_2939 | gatgtgtttctaaggcacga | (SEQ ID NO: 40) |
| NEAT1_3325 | ccattggtattactttacca | (SEQ ID NO: 41) |
| NEAT1_3691 | ttatttgtgctgtaaagggg | (SEQ ID NO: 42) |

REFERENCES

Amaral et al., Nucleic Acids Res 39: D146-151 (2011)
Arredouani et al., Clin Cancer Res 15: 5794-5802 (2009)
Barbieri et al., Nature genetics 44: 685-689 (2012)
Barwick et al., Br J Cancer 102: 570-576 (2010)
Benjamini et al., Journal of the Royal Statistical Society. Series B (Methodological) 57: 289-300 (1995)
Best et al., Clin Cancer Res 11: 6823-6834 (2005)
Blute et al., J Urol 165: 119-125 (2001)
Bond et al., J Cell Biol 186: 637-644 (2009)
Burger et al., Int J Cancer 100: 228-237 (2002)
Cerami et al., Cancer Discov 2: 401-404 (2012)
Chu et al., Journal of visualized experiments: JoVE 61: E3912, 1-6 (2012)
Clemson et al., Mol Cell 33: 717-726 (2009)
de Bono et al., N Engl J Med 364: 1995-2005 (2011)
Erho et al., PLoS One 8: e66855 (2013)
Fredman et al., Science Translational Medicine 7(275): 275ra20: 1-9 (2015)
Gao et al., Sci Signal 6: p11 (2013)
Giannopoulou et al., BMC bioinformatics 12: 277 (2011)
Glinsky et al., J Clin Invest 113: 913-923 (2004)
Grasso et al., Nature 487: 239-243 (2012)
Gumulec et al., Neoplasma 59: 191-201 (2012)
Guttman et al., Nature 458: 223-227 (2009)
Heinlein et al., Endocr Rev 25: 276-308 (2004)
Holzbeierlein et al., Am J Pathol 164: 217-227 (2004)
Hong et al., Clin Cancer Res 17(20): 6582-6591 (2011)
Jiang et al., PLoS One 8: e74386 (2013)
Karnes et al., J Urol 190(6): 2047-2053 (2013)
Lapointe et al., Proc Natl Acad Sci USA 101: 811-816 (2004)
LaTulippe et al., Cancer Res 62: 4499-4506 (2002)
Liu et al., Cancer Res 66: 4011-4019 (2006)
Liu et al., Chem Med Chem 4: 1302-1310 (2009)
Luo et al., Cancer Res 61: 4683-4688 (2001)

Magee et al., Cancer Res 61: 5692-5696 (2001)
Nakagawa et al., J Cell Biol 193: 31-39 (2011)
Rao et al., Advanced Drug Delivery Reviews 61: 746-759 (2009)
Rhodes et al., Neoplasia 6: 1-6 (2004)
Rhodes et al., Neoplasia 9: 166-180 (2007)
Ricke et al., FASEB J 22: 1512-1520 (2008)
Ross et al., Clin Cancer Res 9: 6357-6362 (2003)
Scher et al., N Engl J Med 367: 1187-1197 (2012)
Singh et al., Cancer Cell 1: 203-209 (2002)
Tamura et al., Cancer Res 67: 5117-5125 (2007)
Taylor et al., Cancer Cell 18: 11-22 (2010)
Tomlins et al., Nat Genet 39: 41-51 (2007)
Valencia et al., ACS Nano 7: 10671-10680 (2013)
Vanaja et al., Cancer Res 63: 3877-3882 (2003)
Varambally et al., Cancer Cell 8: 393-406 (2005)
Wallace et al., Cancer Res 68: 927-936 (2008)
Welsh et al., Cancer Res 61: 5974-5978 (2001)
Xiao et al., Cancer Res 61: 6029-6033 (2001)
Xu et al., Proc Natl Acad Sci USA 110(46): 18638-18643 (2013)
Yu et al., Cancer cell 17: 443-454 (2010)
Yu et al., J Clin Oncol 22: 2790-2799 (2004)

What is claimed is:

1. A method of determining the presence or risk of developing or advancing prostate cancer in a subject, comprising
providing a predetermined cut off value, wherein the cut off value is selected from the group consisting of NEAT1 long isoform Biochemical recurrence (BCR) endpoint, NEAT1 long isoform Metastatic recurrence (MET) endpoint, NEAT 1 short isoform BCR endpoint, and NEAT 1 short isoform MET endpoint,
detecting the level of NEAT1 in a biological sample from the subject wherein the biological sample contains prostate cells,
comparing the level of said NEAT1 relative to the predetermined cut off value, and
determining the presence or risk of developing or advancing prostate cancer in the subject based on an elevated level of NEAT1 in the sample as compared to the cut off value.

2. The method of claim 1, wherein said subject has prostate cancer, and an elevated level of NEAT1 as compared to control is indicative of a risk of the cancer progressing into an advanced stage.

3. The method of claim 1, wherein said subject does not have prostate cancer, and an elevated level of NEAT1 as compared to control is indicative of a risk of developing prostate cancer in the subject.

4. The method of claim 1, wherein an elevated level of NEAT1 as compared to control is indicative of the presence of prostate cancer in the subject.

5. The method of claim 1, wherein said sample is selected from the group consisting of prostate tissue, urine, semen, prostatic secretions and prostate cells.

6. The method of claim 1, wherein said detecting comprising performing an assay selected from Northern blot, RNA ISH, RT-PCR, or RNA Seq.

7. The method of claim 6, wherein said assay utilizes a nucleic acid primer or probe that hybridizes to a 5' portion of NEAT1 molecule.

8. The method of claim 6, wherein said assay is RT-PCR which utilizes a pair of primers, both of which hybridize to a 5' portion of NEAT1 molecule.

9. A method, comprising
detecting the level of NEAT1 in a biological sample from a subject wherein the biological sample contains prostate cells,
comparing the level of said NEAT1 relative to a predetermined cut off value, and
determining the presence or risk of developing or advancing prostate cancer in the subject based on an elevated level of NEAT1 in the sample as compared to the predetermined cut off value, and
administering to the subject an interfering RNA molecule targeting NEAT1 if the level of NEAT1 in the sample is elevated as compared to the predetermined cut off value.

10. The method of claim 9, wherein said subject has prostate cancer, and an elevated level of NEAT1 as compared to control is indicative of a risk of the cancer progressing into an advanced stage.

11. The method of claim 9, wherein said subject does not have prostate cancer, and an elevated level of NEAT1 as compared to control is indicative of a risk of developing prostate cancer in the subject.

12. The method of claim 9, wherein an elevated level of NEAT1 as compared to control is indicative of the presence of prostate cancer in the subject.

13. The method of claim 9, wherein said sample is selected from the group consisting of prostate tissue, urine, semen, prostatic secretions and prostate cells.

14. The method of claim 9, wherein said detecting comprising performing an assay selected from Northern blot, RNA ISH, RT-PCR, or RNA Seq.

15. The method of claim 14, wherein said assay utilizes a nucleic acid primer or probe that hybridizes to a 5' portion of NEAT1 molecule.

16. The method of claim 14, wherein said assay is RT-PCR which utilizes a pair of primers, both of which hybridize to a 5' portion of NEAT1 molecule.

17. The method of claim 9, wherein the interfering RNA molecule is an siRNA.

18. The method of claim 9, wherein the interfering RNA molecule is an shRNA.

19. The method of claim 17, wherein the siRNA is conjugated with nanoparticles.

20. The method of claim 17, wherein the siRNA is conjugated with PAMAM dendrimers.

21. The method of claim 9, wherein the subject exhibits resistance to therapy targeting androgen-receptor mediated functions.

22. The method of claim 9, wherein the patient has an advanced stage prostate cancer.

23. The method of claim 9, wherein the interfering RNA is administered to said patient in combination with a therapy targeting androgen-receptor mediated functions.

24. The method of claim 9, wherein the cut off value is selected from the group consisting of NEAT1 long isoform Biochemical recurrence (BCR) endpoint, NEAT1 long isoform Metastatic recurrence (MET) endpoint, NEAT 1 short isoform BCR endpoint, and NEAT 1 short isoform MET endpoint.

* * * * *